Figure 3:
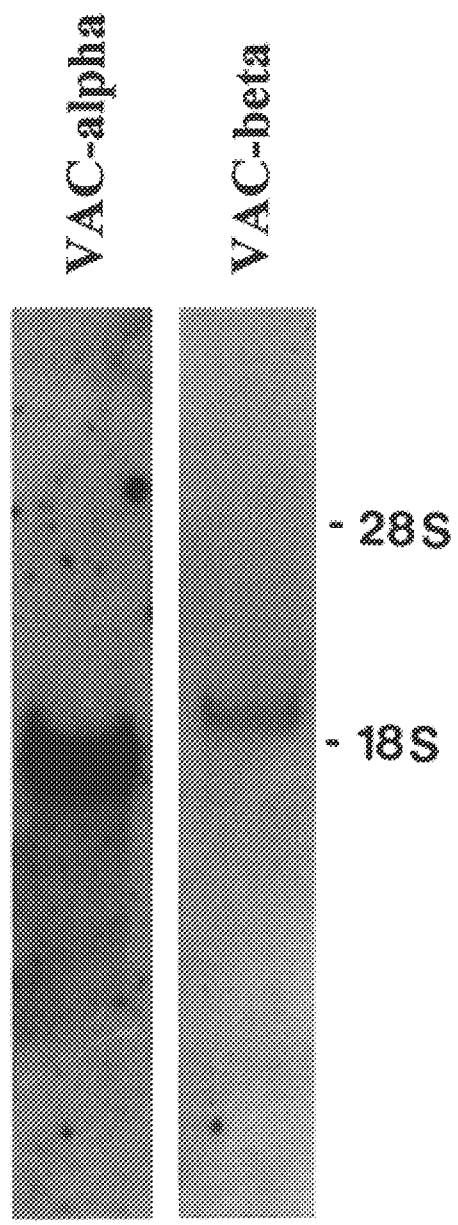

United States Patent [19]

Hauptmann et al.

[11] Patent Number: 5,837,842
[45] Date of Patent: Nov. 17, 1998

[54] VASCULAR ANTICOAGULANT PROTEINS DNA WHICH CODES THEM, PROCESSER FOR PREPARING THEM AND THEIR USE

[75] Inventors: Rudolf Hauptmann, Ebreichsdorf; Ingrid Maurer-Fogy, Vienna; Gerhard Bodo, Vienna; Peter Swetly, Vienna; Christian Stratowa, Vienna; Edgar Falkner, Kritzendorf; Gunther Adolf, Vienna, all of Austria; Christiaan Maria Peter Reutelingsperger, Maastricht, Netherlands

[73] Assignee: Boehringer Ingelheim International GmbH, Ingelheim am Rhein, Germany

[21] Appl. No.: 376,050

[22] Filed: Jan. 23, 1995

Related U.S. Application Data

[62] Division of Ser. No. 230,875, Apr. 20, 1994, abandoned, which is a continuation of Ser. No. 868,337, Apr. 7, 1992, abandoned, which is a division of Ser. No. 294,602, Jan. 30, 1989, abandoned.

[30] Foreign Application Priority Data

| Mar. 28, 1987 | [DE] | Germany | 37 10 364.4 |
| Mar. 28, 1987 | [DE] | Germany | 37 10 309.1 |
| Mar. 28, 1987 | [DE] | Germany | 37 10 430.6 |
| Nov. 4, 1987 | [DE] | Germany | 37 37 367.6 |
| Mar. 26, 1988 | [WO] | WIPO | PCT/EP88/00266 |

[51] Int. Cl.$^6$ .................................................. C07H 21/04
[52] U.S. Cl. ............................................ 536/23.5; 536/23.1
[58] Field of Search .................................. 436/69.1, 69.6, 436/172.3, 320.1; 530/380, 381; 514/2, 12; 536/23.5

[56] References Cited

U.S. PATENT DOCUMENTS

| 4,732,891 | 3/1988 | Maki | 514/12 |
| 4,736,018 | 4/1988 | Reutelingsperger | 530/381 |
| 4,937,324 | 6/1990 | Fujikawa | 530/397 |
| 5,066,787 | 11/1991 | Reutelingsperger | 530/380 |
| 5,066,788 | 11/1991 | Reutelingsperger | 530/381 |
| 5,179,081 | 1/1993 | Iwasaki et al. | 514/12 |

OTHER PUBLICATIONS

Reutelingsperger, C.P.M. et al., *Eur. J. Biochem.* 151:625–629 (1985).
Sevier et al. Clinical Chemistry vol. 27 No. 11. 1981 1797.
Iwasaki et al. J. Biochem 102, No. 5, 1261 1987.

*Primary Examiner*—Rebecca E. Prouty
*Assistant Examiner*—Enrique D. Longton
*Attorney, Agent, or Firm*—Sterne, Kessler, Goldstein & Fox P.L.L.C.

[57] ABSTRACT

This invention relates to biologically active proteins, the DNA molecules coding for them, processes for preparing them and their use.

4 Claims, 65 Drawing Sheets

Tryptic peptides

| | |
|---|---|
| P5 | H A L K |
| P7 | G E T S G D Y K |
| P11/I | W G T D E E K |
| P11/II | T P E E L R |
| P12 | G A G T D D H T L I R |
| P14 | Q E I S A A F K |
| P15 | T L F G R |
| P16/I | L Y D A Y E L K |
| P16/II | W?L Y D A Y E L K |
| P17 | V L T E I I A S R |
| P18 | G T V T D F P G F D E R |
| P20/I | Q V Y E E E Y G S S L E D D V V G D T S G Y Y Q R |
| P20/II | L I V A L M K |
| P21/I | S E I D L F N I R K |
| P23/I | F I T I F G T R |
| P24 | K N F A T S L Y S M I K |
| P25 | S?G T D E E K F I T I F G T |
| P27 | D L L D D L K S E L T G K F E K |
| P29/I | G L G T D E E S I L T L L T S R |
| P29/II | M L V V L L Q A N R D P D A G I D E A Q V X Q X A Q A L F Q A |
| P30/I | X I P A Y L A E T L Y Y A M K |
| P30/II | E T X G N L E Q L L L A V V K |

BrCN-Peptides

| | |
|---|---|
| BrCN 1 | K G A G T D D H T L I R V |
| BrCN 4 | I K G D T S G D Y K K A |
| BrCN 15 | K P S R L Y D A Y E L K H A L K G A G T N E K V L T E I I |
| BrCN 22 | K G L G T D E E S I L T L L T S X X N A Q |

FIG.0.1

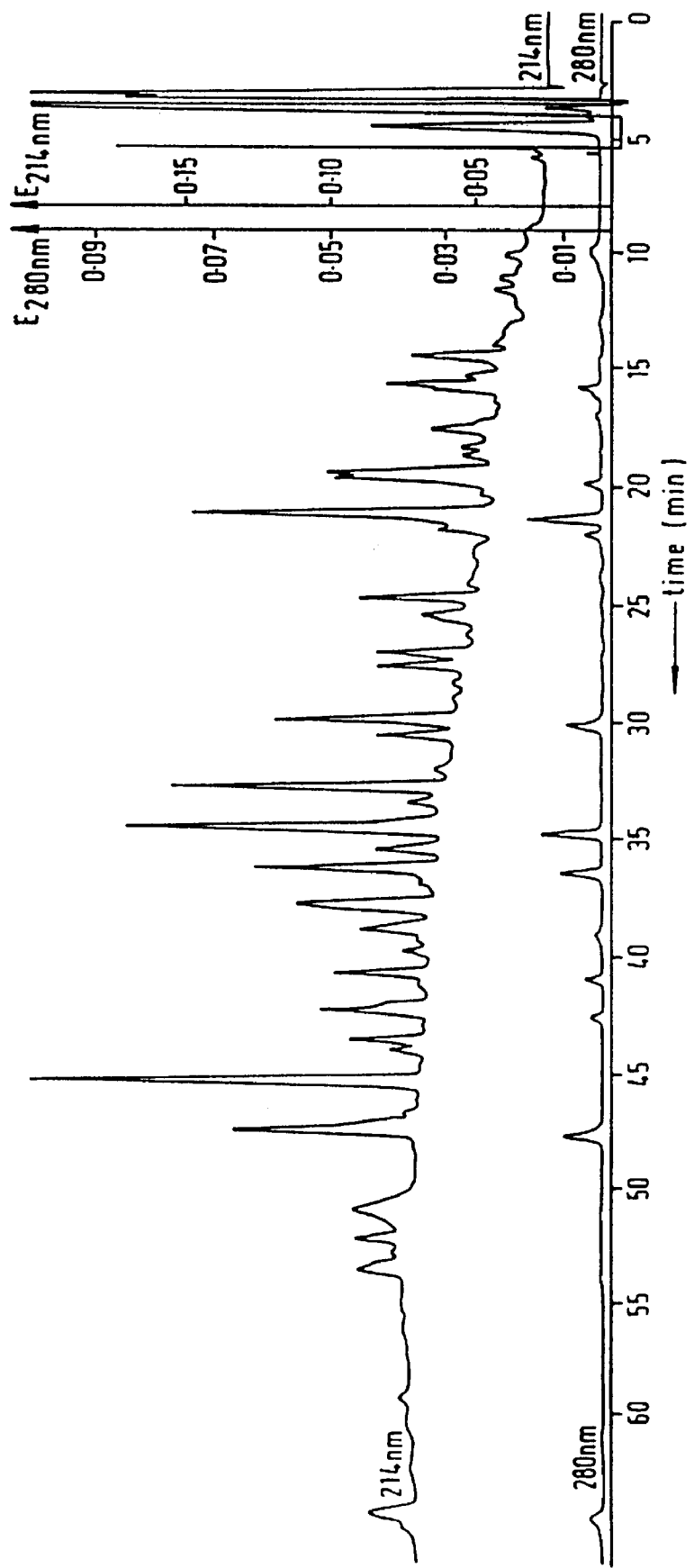
FIG. 0.2

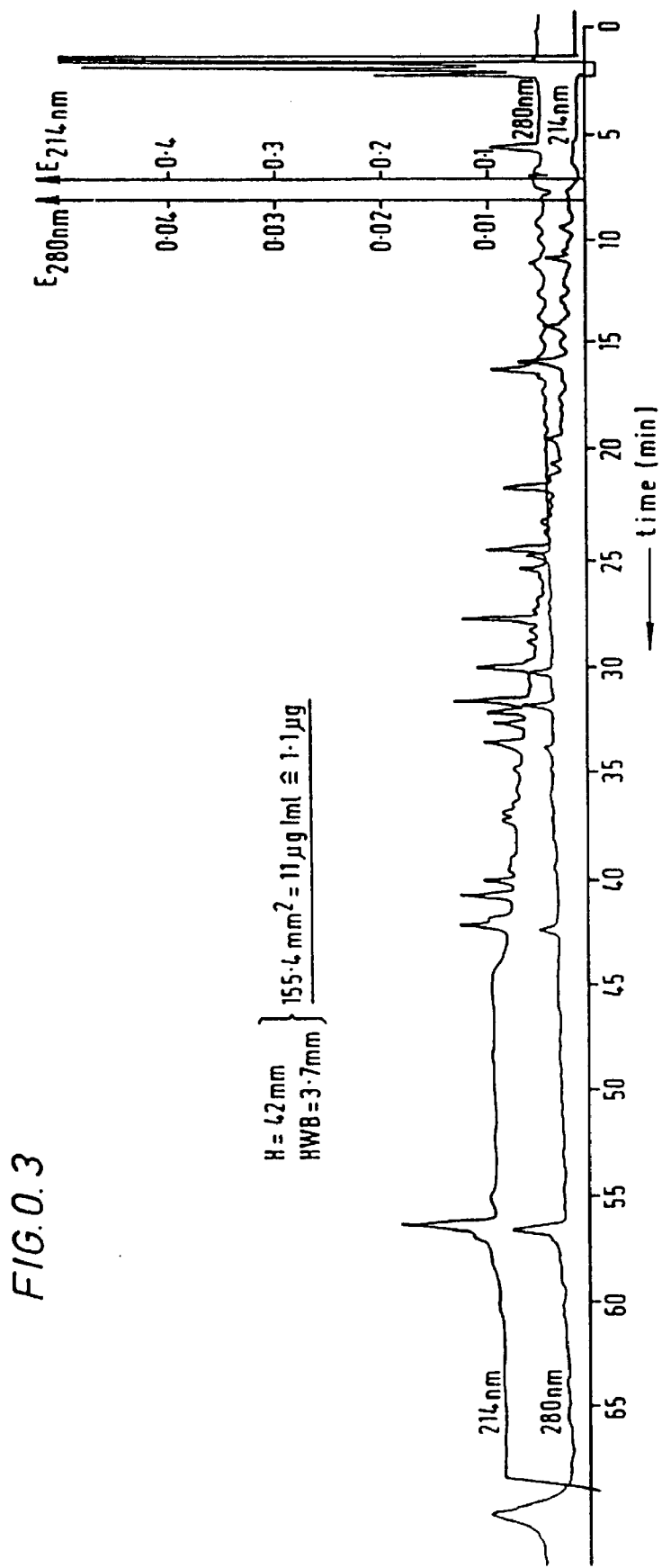
FIG. 0.3

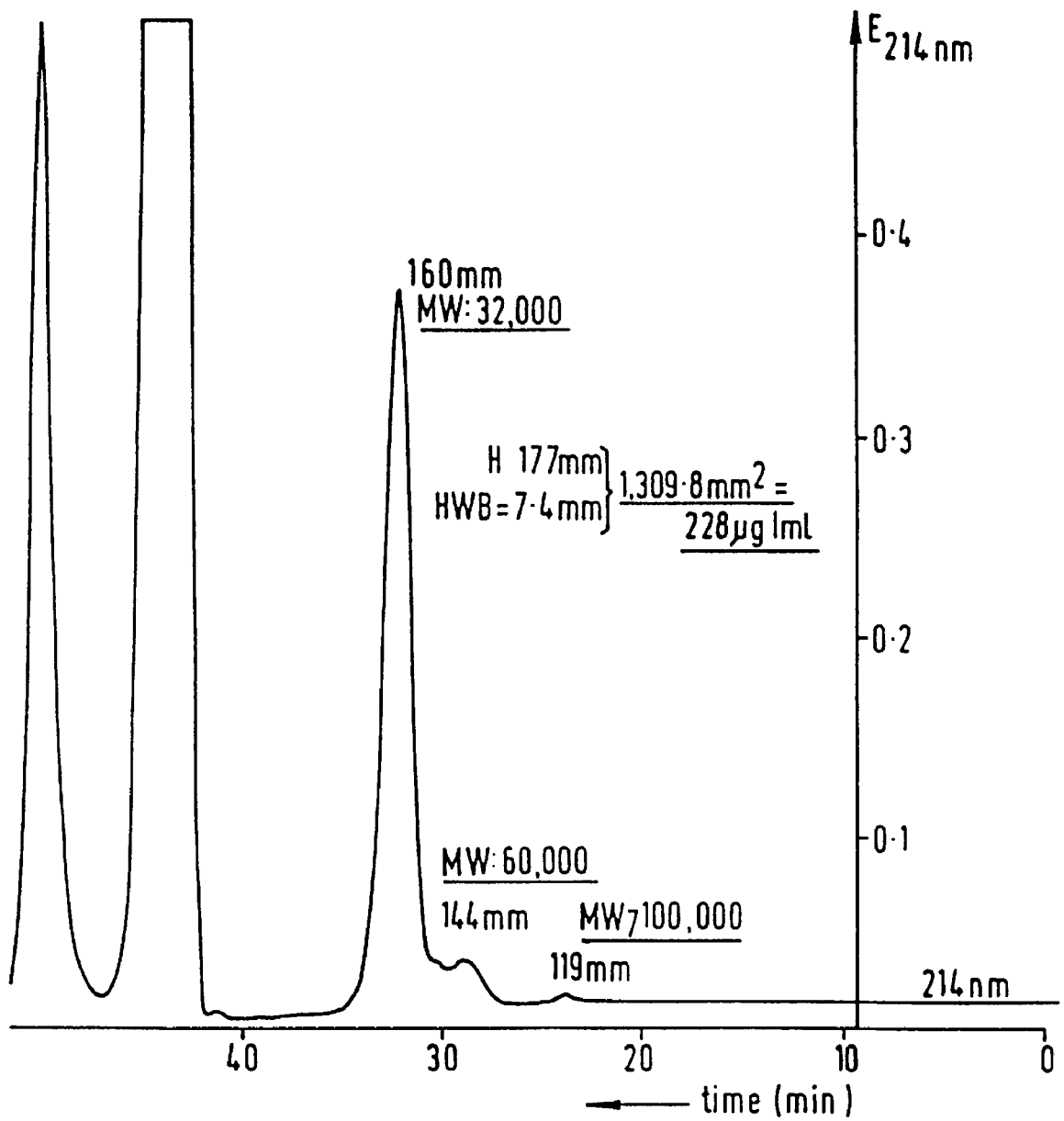
FIG. O. 4/1

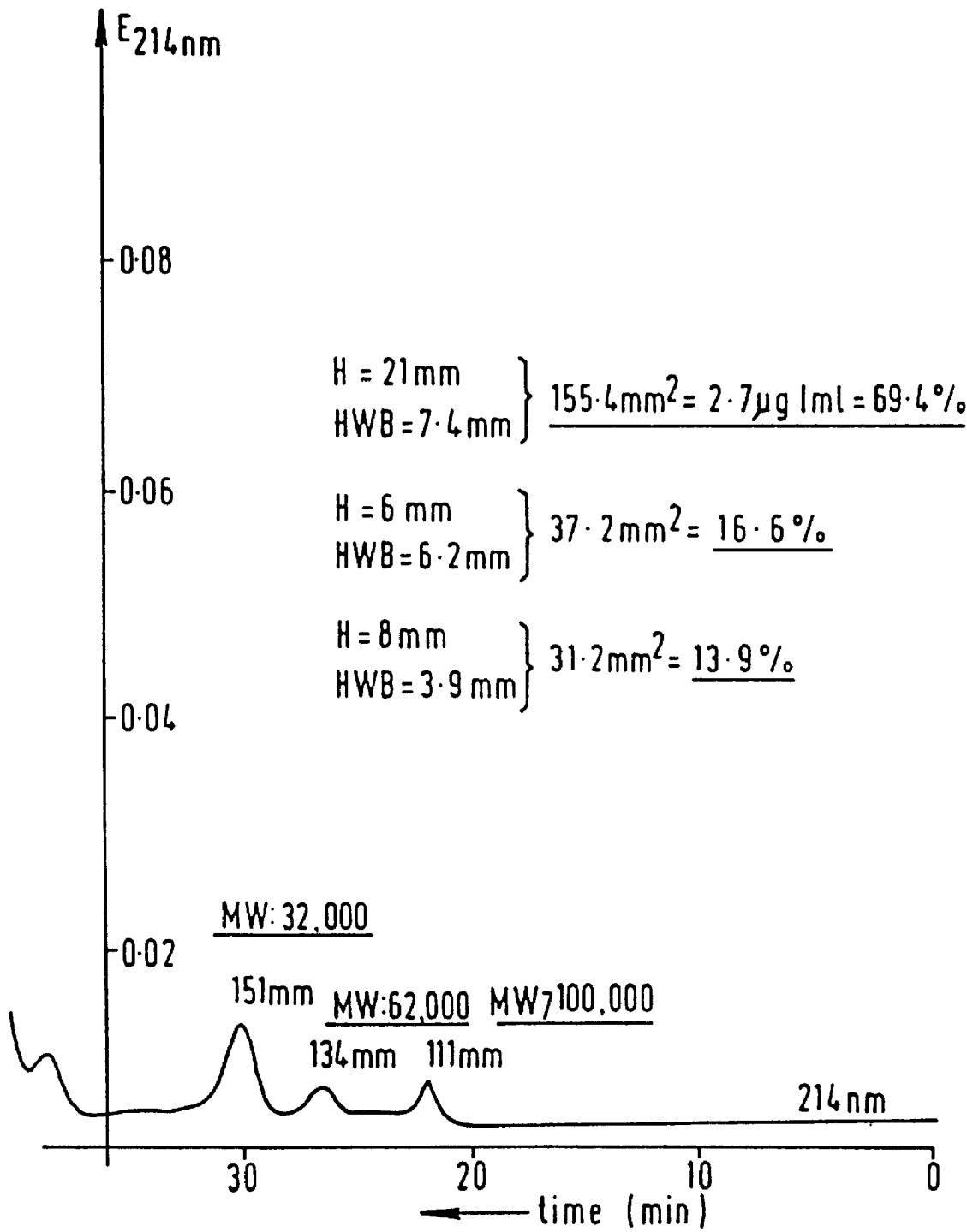
FIG. 0. 4/2

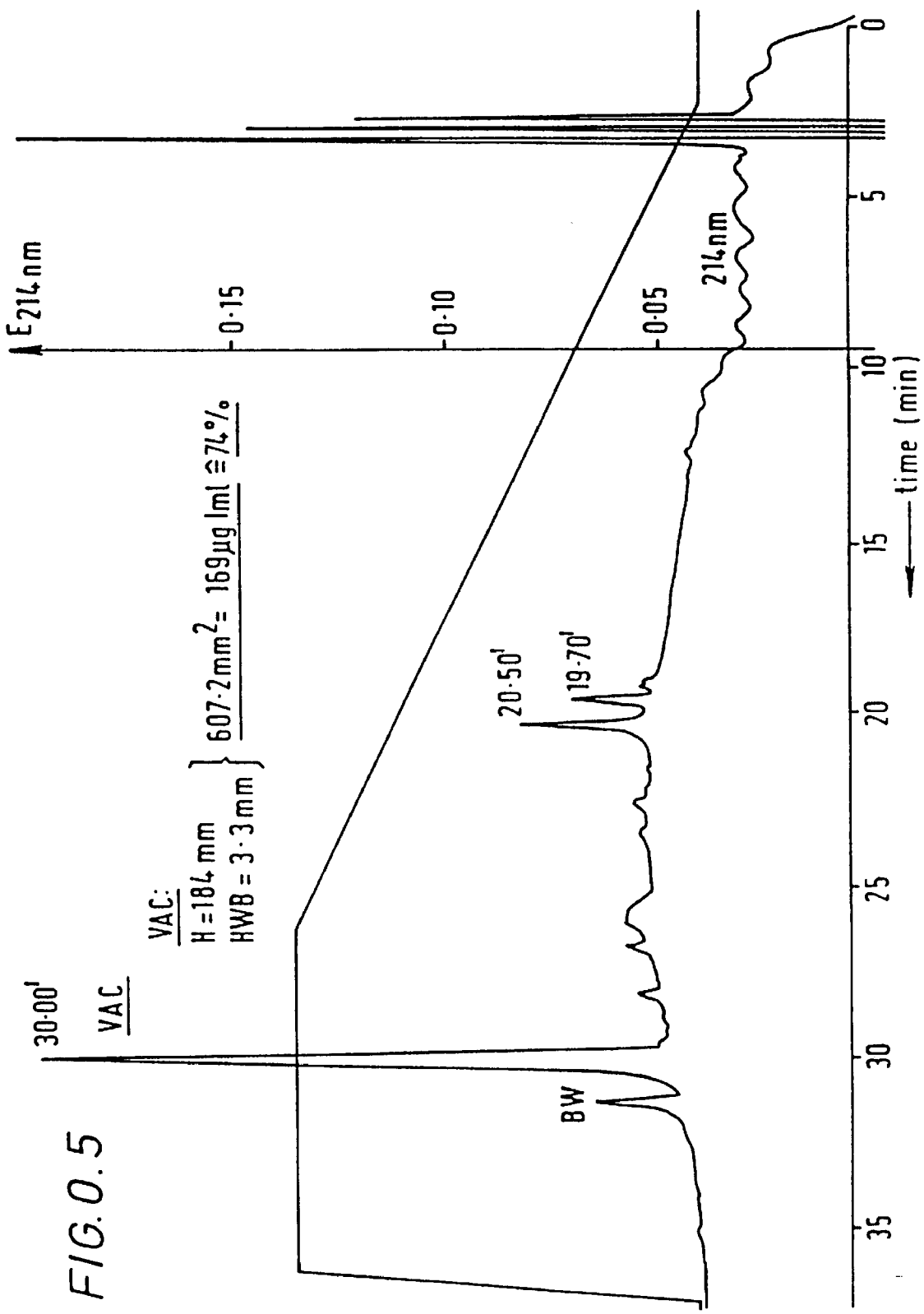
FIG. 0.5

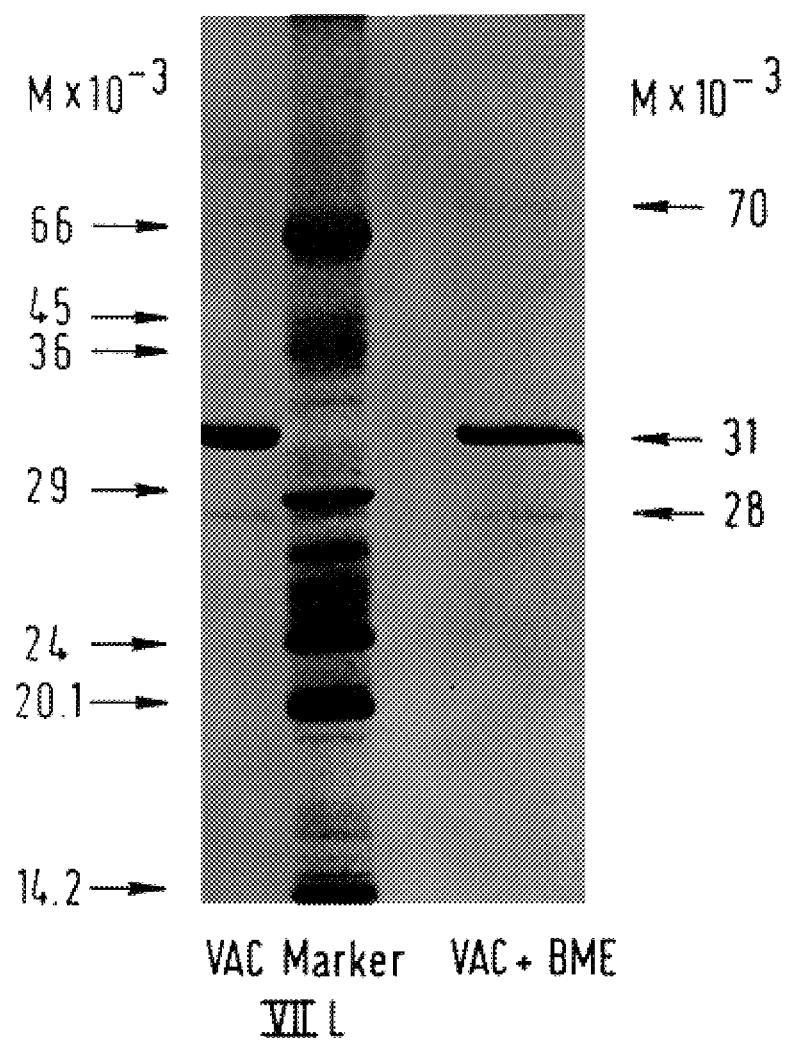
FIG. 0.6

Tryptic peptide P16/II

```
            W?  L   Y   D   A   Y   E   L   K
5'   ...UGGCUNUAUGAUGCNUAUGAA...          3'              mRNA
              C   C       C   G
         UUA
           G

3'       ACCGAAATACTACGAATACT              5'
             G   G   G   G   G                            EBI - 387
             C       C
             T       T

3'       ACCAACATACTACGAATACT              5'
           T   G   G   G   G                              EBI - 388
                   C
                   T
```

Staph-A Peptide P20/I/6
       (Subfragment of the tryptic peptide P20/I)

```
            D   D   V   V   G   D   T   S   G   Y   Y   R
5'   ...GAUGAUGUNGUNGGNGAUACN...          3'              mRNA
            C   C           C
3'       CTACTACAACAACCACTATG              5'
           G   G   G   G   G   G                          EBI - 386
               C   C   C
               T   T   T
```

FIG. 1

Tryptic peptide P30/I

```
X   I   P   A   Y   L   A   E   T   L   Y   Y   A   M   K
      5'         ...GAAACNCUNUACUACGCNAUGAAA...           3'      mRNA
                      G         U   U       G
                            UUA
                             G

3'         CTCTGIIAIATIATICGITACTT                  5'      EBI - 118
      3'         CTTTGIIAIATIATICGITACTT                  5'      EBI - 119
```

FIG.2

VAC-alpha cDNA

```
                    CCTGCTTCACCTTCCCCTGACCTGAGTAGTCGCT
 1              5                  10                 15
Met Ala Gln Val Leu Arg Gly Thr Val Thr Asp Phe Pro Gly Phe
ATG GCA CAG GTT CTC AGA GGC ACT GTG ACT GAC TTC CCT GGA TTT      45

20                  25                 30
Asp Glu Arg Ala Asp Ala Glu Thr Leu Arg Lys Ala Met Lys Gly
GAT GAG CGG GCT GAT GCA GAA ACT CTT CGG AAG GCT ATG AAA GGC      90

35                  40                 45
Leu Gly Thr Asp Glu Glu Ser Ile Leu Thr Leu Leu Thr Ser Arg
TTG GGC ACA GAT GAG GAG AGC ATC CTG ACT CTG TTG ACA TCC CGA     135

50                  55                 60
Ser Asn Ala Gln Arg Gln Glu Ile Ser Ala Ala Phe Lys Thr Leu
AGT AAT GCT CAG CGC CAG GAA ATC TCT GCA GCT TTT AAG ACT CTG     180

65                  70                 75
Phe Gly Arg Asp Leu Leu Asp Asp Leu Lys Ser Glu Leu Thr Gly
TTT GGC AGG GAT CTT CTG GAT GAC CTG AAA TCA GAA CTA ACT GGA     225

80                  85                 90
Lys Phe Glu Lys Leu Ile Val Ala Leu Met Lys Pro Ser Arg Leu
AAA TTT GAA AAA TTA ATT GTG GCT CTG ATG AAA CCC TCT CGG CTT     270

95                 100                105
Tyr Asp Ala Tyr Glu Leu Lys His Ala Leu Lys Gly Ala Gly Thr
TAT GAT GCT TAT GAA CTG AAA CAT GCC TTG AAG GGA GCT GGA ACA     315

110                 115                120
Asn Glu Lys Val Leu Thr Glu Ile Ile Ala Ser Arg Thr Pro Glu
AAT GAA AAA GTA CTG ACA GAA ATT ATT GCT TCA AGG ACA CCT GAA     360

125                 130                135
Glu Leu Arg Ala Ile Lys Gln Val Tyr Glu Glu Glu Tyr Gly Ser
GAA CTG AGA GCC ATC AAA CAA GTT TAT GAA GAA GAA TAT GGC TCA     405

140                 145                150
Ser Leu Glu Asp Asp Val Val Gly Asp Thr Ser Gly Tyr Tyr Gln
AGC CTG GAA GAT GAC GTG GTG GGG GAC ACT TCA GGG TAC TAC CAG     450
```

FIG.4A

```
                    155                     160                     165
Arg Met Leu Val Val Leu Leu Gln Ala Asn Arg Asp Pro Asp Ala
CGG ATG TTG GTG GTT CTC CTT CAG GCT AAC AGA GAC CCT GAT GCT         495

170                     175                     180
Gly Ile Asp Glu Ala Gln Val Glu Gln Asp Ala Gln Ala Leu Phe
GGA ATT GAT GAA GCT CAA GTT GAA CAA GAT GCT CAG GCT TTA TTT         540

185                     190                     195
Gln Ala Gly Glu Leu Lys Trp Gly Thr Asp Glu Glu Lys Phe Ile
CAG GCT GGA GAA CTT AAA TGG GGA ACA GAT GAA GAA AAG TTT ATC         585

200                     205                     210
Thr Ile Phe Gly Thr Arg Ser Val Ser His Leu Arg Lys Val Phe
ACC ATC TTT GGA ACA CGA AGT GTG TCT CAT TTG AGA AAG GTG TTT         630

215                     220                     225
Asp Lys Tyr Met Thr Ile Ser Gly Phe Gln Ile Glu Glu Thr Ile
GAC AAG TAC ATG ACT ATA TCA GGA TTT CAA ATT GAG GAA ACC ATT         675

230                     235                     240
Asp Arg Glu Thr Ser Gly Asn Leu Glu Gln Leu Leu Leu Ala Val
GAC CGC GAG ACT TCT GGC AAT TTA GAG CAA CTA CTC CTT GCT GTT         720

245                     250                     255
Val Lys Ser Ile Arg Ser Ile Pro Ala Tyr Leu Ala Glu Thr Leu
GTG AAA TCT ATT CGA AGT ATA CCT GCC TAC CTT GCA GAG ACC CTC         765

260                     265                     270
Tyr Tyr Ala Met Lys Gly Ala Gly Thr Asp Asp His Thr Leu Ile
TAT TAT GCT ATG AAG GGA GCT GGG ACA GAT GAT CAT ACC CTC ATC         810

275                     280                     285
Arg Val Met Val Ser Arg Ser Glu Ile Asp Leu Phe Asn Ile Arg
AGA GTC ATG GTT TCC AGG AGT GAG ATT GAT CTG TTT AAC ATC AGG         855

290                     295                     300
Lys Glu Phe Arg Lys Asn Phe Ala Thr Ser Leu Tyr Ser Met Ile
AAG GAG TTT AGG AAG AAT TTT GCC ACC TCT CTT TAT TCC ATG ATT         900

305                     310                     315
Lys Gly Asp Thr Ser Gly Asp Tyr Lys Lys Ala Leu Leu Leu Leu
AAG GGA GAT ACA TCT GGG GAC TAT AAG AAA GCT CTT CTG CTG CTC         945

320
Cys Gly Glu Asp Asp  *
TGT GGA GAA GAT GAC TAA CGTGTCACGGGGAAGAGCTCCCTGCTGTGTGCCTG         998
```

FIG.4B

```
CACCACCCCACTGCCTTCCTTCAGCACCTTTAGCTGCATTTGTATGCCAGTGCTTAACA    1057

CATTGCCTTATTCATACTAGCATGCTCATGACCAACACATACACGTCATAGAAGAAAAT    1116

AGTGGTGCTTCTTTCTGATCTCTAGTGGAGATCTCTTTGACTGCTGTAGTACTAAAGTG    1175

TACTTAATGTTACTAAGTTTAATGCCTGGCCATTTTCCATTTATATATATTTTTTAAGA    1234

GGCTAGAGTGCTTTTAGCCTTTTTTAAAAACTCCATTTATATTACATTTGTAACCATGA    1293

TACTTTAATCAGAAGCTTAGCCTTGAAATTGTGAACTCTTGGAAATGTTATTAGTGAAG    1352

TTCGCAACTAAACTAAACCTGTAAAATTATGATGATTGTATTCAAAAGATTAATGAAAA    1411

ATAAACATTTCTGTCCCCCTG-polyA                                   1437
```

FIG.4C

Sequenced VAC-peptides:comparison with sequence

```
                                                      BrCN 22
                                                      K G L G T D
             P18                                      P29/I
             G T V T D F P G F D E R                  G L G T D
M A Q V L R G T V T D F P G F D E R A D A E T L R K A M K G L G T D
            10                    20                    30

E E S I L T L L T S X X N A Q
                            P14           P15           P27
E E S I L T L L T S R       Q E I S A A F K T L F G R D L L
E E S I L T L L T S R S N A Q R Q E I S A A F K T L F G R D L L
        40                    50                    60

BrCN 15
                                    K P S R L Y D A Y E L K H
                                            P16/II
                                            W?L Y D A Y E L K
                  P20/II                    P16/I              P5
D D L K S E L T G K F E K L I V A L M K     L Y D A Y E L K H
D D L K S E L T G K F E K L I V A L M K P S R L Y D A Y E L K H
    70                    80                    90

A L K G A G T N E K V L T E I I
                      P17                   P11/II              P20/I
A L K                 V L T E I I A S R T P E E L R     Q V Y E
A L K G A G T N E K V L T E I I A S R T P E E L R A I K Q V Y E
100                   110                   120                   130

P29/II
E E Y G S S L E D D V V G D T S G Y Y Q R M L V V L L Q A N R D
E E Y G S S L E D D V V G D T S G Y Y Q R M L V V L L Q A N R D
                140                   150                   160

P11/I
                                        W G T D E E K   P23/I
                                        P25                       F
P D A G I D E A Q V X Q X A Q A L F Q A       S?G T D E E K F
P D A G I D E A Q V E Q D A Q A L F Q A G E L K W G T D E E K F
          170                   180                   190

I T I F G T R
I T I F G T
I T I F G T R S V S H L R K V F D K Y M T I S G F Q I E E T I D
      200                   210                   220
```

FIG.5A

```
   P30/II                              P30/I
   E T X G N L E Q L L L A V V K       E I P A Y L A E T L Y Y A
   R E T S G N L E Q L L L A V V K S I R S I P A Y L A E T L Y Y A
     230                 240                 250

BrCN 1
   K G A G T D D H T L I R V
     P12                             P21/I                     P24
   M K G A G T D D H T L I R         S E I D L F N I R K       K
   M K G A G T D D H T L I R V M V S R S E I D L F N I R K E F R K
   260                 270                 280                 290

BrCN 4
            I K G D T S G D Y K K A
              P7
   N F A T S L Y S M I K G E T S G D Y K
   N F A T S L Y S M I K G D T S G D Y K K A L L L L C G E D D *
           300                 310                 320
```

FIG.5B

VAC-alpha: Quadruplication of a 67 amino acid long sequence

```
                                          MAQVLRGTVTDFPGFDERA
DAETLRKAMKG-LGTDEESILTLLTSRSNAQRQEISAAFKTLFGRDLLDDLKSELTGKFEKLIVALMK        PSRLY
DAYELKHALKG-AGTNEKVLTEIIASRTPEELRAIKQVYEEEYGSSLEDDVVGDTSGYYQRMLVVLLQ        ANRDPDAGIDEAQVI
DAQALFQAGELKWGTDEEKFITIFGTRSVSHLRKVFDKYMTISGFQIEETIDRETSGNLEQLLAVVK         SIRSIPAY
LAETLYYAMKG-AGTDDHTLIRVMVSRSEIDLFNIRKEFRKNFATSLYSMIKGDTSGDYKKALLLLCG        EDD*

KG-hGTDExxLIpILApR                               oooooo

DAetL      AmKG       aGIDEe liti  SRS      Lr I   y t  fG sLeddikgeTSG yekllvaL k
                                                   d                    l "Consensus":    x  :  50% of amino acids identical
                X  :  75% of amino acids identical
                X  : 100% of amino acids identical "oooooo" :  Hydrophobic region
```

FIG.6

VAC-beta cDNA

```
                AGGCCTGCTCACTCCTCAGCTGCAGGAGCCAGACGTGTGGAGTCCCA
GCAGAGGCCAACCTGTGTCTCTTCATCTCCGTGAGAAAGGTGCCCCCGAAGTGAAAGAG
```

```
 1                   5                   10                  15
Met Ala Trp Trp Lys Ala Trp Ile Glu Gln Glu Gly Val Thr Val
ATG GCC TGG TGG AAA GCC TGG ATT GAA CAG GAG GGT GTC ACA GTG           45

20                  25                  30
Lys Ser Ser Ser His Phe Asn Pro Asp Pro Asp Ala Glu Thr Leu
AAG AGC AGC TCC CAC TTC AAC CCA GAC CCT GAT GCA GAG ACC CTC          90

35                  40                  45
Tyr Lys Ala Met Lys Gly Ile Gly Thr Asn Glu Gln Ala Ile Ile
TAC AAA GCC ATG AAG GGG ATC GGG ACC AAC GAG CAG GCT ATC ATC         135

50                  55                  60
Asp Val Leu Thr Lys Arg Ser Asn Thr Gln Arg Gln Gln Ile Ala
GAT GTG CTC ACC AAG AGA AGC AAC ACG CAG CGG CAG CAG ATC GCC         180

65                  70                  75
Lys Ser Phe Lys Ala Gln Phe Gly Lys Asp Leu Thr Glu Thr Leu
AAG TCC TTC AAG GCT CAG TTC GGC AAG GAC CTC ACT GAG ACC TTG         225

80                  85                  90
Lys Ser Glu Leu Ser Gly Lys Phe Glu Arg Leu Ile Val Ala Leu
AAG TCT GAG CTC AGT GGC AAG TTT GAG AGG CTC ATT GTG GCC CTT         270

95                  100                 105
Met Tyr Pro Pro Tyr Arg Tyr Glu Ala Lys Glu Leu His Asp Ala
ATG TAT CCG CCA TAC AGA TAC GAA GCC AAG GAG CTG CAT GAC GCC         315

110                 115                 120
Met Lys Gly Leu Gly Thr Lys Glu Gly Val Ile Ile Glu Ile Leu
ATG AAG GGC TTA GGA ACC AAG GAG GGT GTC ATC ATT GAG ATC CTG         360

125                 130                 135
Ala Ser Arg Thr Lys Asn Gln Leu Arg Glu Ile Met Lys Ala Tyr
GCC TCT CGG ACC AAG AAC CAG CTG CGG GAG ATA ATG AAG GCG TAT         405

140                 145                 150
Glu Glu Asp Tyr Gly Ser Ser Leu Glu Glu Asp Ile Gln Ala Asp
GAG GAA GAC TAT GGG TCC AGC CTG GAG GAG GAC ATC CAA GCA GAC         450
```

FIG.7A

```
                         155                    160                     165
     Thr Ser Gly Tyr Leu Glu Arg Ile Leu Val Cys Leu Leu Gln Gly
     ACA AGT GGC TAC CTG GAG AGG ATC CTG GTG TGC CTC CTG CAG GGC          495

170                    175                     180
     Ser Arg Asp Asp Val Ser Ser Phe Val Asp Pro Ala Leu Ala Leu
     AGC AGG GAT GAT GTG AGC AGC TTT GTG GAC CCG GCA CTG GCC CTC          540

185                    190                     195
     Gln Asp Ala Gln Asp Leu Tyr Ala Ala Gly Glu Lys Ile Arg Gly
     CAA GAC GCA CAG GAT CTG TAT GCG GCA GGC GAG AAG ATT CGT GGG          585

200                    205                     210
     Thr Asp Glu Met Lys Phe Ile Thr Ile Leu Cys Thr Arg Ser Ala
     ACT GAT GAG ATG AAA TTC ATC ACC ATC CTG TGC ACG CGC AGT GCC          630

215                    220                     225
     Thr His Leu Leu Arg Val Phe Glu Glu Tyr Glu Lys Ile Ala Asn
     ACT CAC CTG CTG AGA GTG TTT GAA GAG TAT GAG AAA ATT GCC AAC          675

230                    235                     240
     Lys Ser Ile Glu Asp Ser Ile Lys Ser Glu Thr His Gly Ser Leu
     AAG AGC ATT GAG GAC AGC ATC AAG AGT GAG ACC CAT GGC TCA CTG          720

245                    250                     255
     Glu Glu Ala Met Leu Thr Val Val Lys Cys Thr Gln Asn Leu His
     GAG GAG GCC ATG CTC ACT GTG GTG AAA TGC ACC CAA AAC CTC CAC          765

260                    265                     270
     Ser Tyr Phe Ala Glu Arg Leu Tyr Tyr Ala Met Lys Gly Ala Gly
     AGC TAC TTT GCA GAG AGA CTC TAC TAT GCC ATG AAG GGA GCA GGG          810

275                    280                     285
     Thr Arg Asp Gly Thr Leu Ile Arg Asn Ile Val Ser Arg Ser Glu
     ACG CGT GAT GGG ACC CTG ATA AGA AAC ATC GTT TCA AGG AGC GAG          855

290                    295                     300
     Ile Asp Leu Asn Leu Ile Lys Cys His Phe Lys Lys Met Tyr Gly
     ATT GAC TTA AAT CTT ATC AAA TGT CAC TTC AAG AAG ATG TAC GGC          900

305                    310                     315
     Lys Thr Leu Ser Ser Met Ile Met Glu Asp Thr Ser Gly Asp Tyr
     AAG ACC CTC AGC AGC ATG ATC ATG GAA GAC ACC AGC GGC GAC TAC          945

320                    325
     Lys Asn Ala Leu Leu Ser Leu Val Gly Ser Asp Pro  *
     AAG AAC GCC CTG CTG AGC CTG GTG GGC AGC GAC CCC TGA GGCACAG          991
```

FIG.7B

| | |
|---|---|
| AAGAACAAGAGCAAAGACCATGAAGCCAGAGTCTCCAGGACTCCTCACTCAACCTCGGC | 1050 |
| CATGGACGCAGGTTGGGTGTGAGGGGGGTCCCAGCCTTTCGGTCTTCTATTTCCCTATT | 1109 |
| TCCAGTGCTTTCCAGCCGGGTTTCTGACCCAGAGGTGGAACCGGCCTGGACTCCTCTTC | 1168 |
| CCAACTTCCTCCAGGTCATTTCCCAGTGTGAGCACAATGCCAACCTTAGTGTTTCTCCA | 1227 |
| GCCAGACAGATGCCTCAGCATGAAGGGCTTGGGGACTTGTGGATCATTCCTTCCTCCCT | 1286 |
| GCAGGAGCTTCCCAAGCTGGTCACAGAGTCTCCTGGGCACAGGTTATACAGACCCCAGC | 1345 |
| CCCATTCCCATCTACTGAAACAGGGTCTCCACAAGAGGGGCCAGGGAATATGGGTTTTT | 1404 |
| AACAAGCGTCTTACAAAACACTTCTCTATCATGCAGCCGGAGAGCTGGCTGGGAGCCCT | 1463 |
| TTTGTTTTAGAACACACATCCTTCAGCAGCTGAGAAATGAACACGAATCCATCCCAACC | 1522 |
| GAGATGCCATTAACATTCATCTAAAAATGTTAGGCTCTAAATGGACGAAAAATTCTCTC | 1581 |
| GCCATCTTAATAACAAAATAAACTACAAATTCCTGACCCAAGGACACTGTGTTATAAGA | 1640 |
| GGCGTGGGCTCCCCTGGTGGCTGACCAGGTCAGCTGCCCTGGCCTTGCACCCCTCTGCA | 1699 |
| TGCAGCACAGAAGGGTGTGACCATGCCCTCAGCACCACTCTTGTCCCCACTGAACGGCA | 1758 |
| ACTGAGACTGGGTACCTGGAGATTCTGAAGTGCCTTTGCTGTGGTTTTCAAAATAATAA | 1817 |
| AGATTTGTATTCAACTC-polyA | 1834 |

FIG.7C

VAC-beta: Quadruplication of a 67 amino acid long sequence

```
                                      MAWWKAWIEQEGVTVKSSSHFNPDP

DAETLYKAMKG-IGTNEQAIIDVLTKRSNTQRQQIAKSFKAQFGKDLTETLKSELSGKFERLIVALMY   PPYRY

EAKELHDAMKG-LGTKEGVIIEILASRTKNQLREIMKAYEEDYGSSLEEDIQADTSGYLERILVCLLQ  GSRDDVSSFVDPALALQ

DAQDLYAAGEKIRGTDEMKFITILCTRSATHLLRVFEEYEKIANKSIEDSIKSETHGSLEEAMLTVVK  CTQNLHSY

FAERLYYAMKG-AGTRDGTLIRNIVSRSEIDLNLIKCHFKKMYGKTLSSMIMEDTSGDYKNALLSLVG  SDP*

KG-hGTDExxLipILApR                                         oooooo dAe LY AMKG GI Eg ii iL sRS tqL I k ykk yGKsLee IkseTSG lEralv Lvk
                                  fe                    d       l
```

"Consensus":    x : 50% of amino acids identical
                  X : 75% of amino acids identical
                  <u>X</u> : 100% of amino acids identical "oooooo" : Hydrophobic region

FIG. 8

AMINO ACID COMPOSITION

| | VAC-alpha | | VAC-beta | |
|---|---|---|---|---|
| Ala | 26 | (8,1%) | 25 | (7,7%) |
| Cys | 1 | (0,3%) | 4 | (1,2%) |
| Asp | 25 | (7,8%) | 20 | (6,1%) |
| Asn | 6 | (1,9%) | 9 | (2,8%) |
| Glu | 29 | (9,1%) | 29 | (8,9%) |
| Gln | 12 | (3,8%) | 12 | (3,7%) |
| Phe | 13 | (4,1%) | 9 | (2,8%) |
| Gly | 22 | (6,9%) | 20 | (6,1%) |
| His | 3 | (0,9%) | 6 | (1,8%) |
| Ile | 18 | (5,6%) | 23 | (7,0%) |
| Lys | 22 | (6,9%) | 27 | (8,3%) |
| Leu | 38 | (11,9%) | 33 | (10,1%) |
| Met | 8 | (2,5%) | 11 | (3,4%) |
| Pro | 5 | (1,6%) | 6 | (1,8%) |
| Arg | 19 | (5,9%) | 15 | (4,6%) |
| Ser | 21 | (6,6%) | 27 | (8,3%) |
| Thr | 23 | (7,2%) | 21 | (6,4%) |
| Val | 16 | (5,0%) | 13 | (4,0%) |
| Trp | 1 | (0,3%) | 3 | (0,9%) |
| Tyr | 12 | (3,8%) | 14 | (4,3%) |
| | MW = 35896 | | MW = 36837 | |
| CHARGED: | 98 | (30,6%) | 97 | (29,6%) |

*FIG. 9*

Comparison of VAC-alpha and VAC-beta

```
alpha                                                   MAQVLRGTVTDFPGFDERA
beta                                          MAWWKAWIEQEGV..KSSSH.NPDP alpha DAETLRKAMKGLGTDEESILTLLTSRSNAQRQEISAAFKTLFGRDLLDDLKSELTGKFEKLIVALMK    PSRLY
beta  .....y.....I..N.QA.IDV..K...T...Q.AKS..AQ..K..TET.....S....R......Y    .PYR.

alpha DAYELKHALKGAGTNEKVLTEIIASRTPEELRAIKQVYEEEYGSSLEDDVVGDTSGYYQRMLVVLLQ    ANRDPDAG-IDEAQVEQ
beta  E.K..HD.M..L..K.G.II..L....KNQ..E.MKA...D......E.IQA.....LE.I..C...    GS..DVSSFV.P.LAL.

alpha DAQALFQAGELKWGTDEEKFITIFGTRSVSHLRKVFDKYMTISGFQIEETIDRETSGNLEQLLLAVVK   SIRSIPAY
beta  ...D.YA...KIR....M.....LC...AT..LR..EE.EK.ANKS..DS.KS..H.S..EAM.T...   CTQNLHS.

alpha LAETLYYAMKGAGTDDHTLIRVMVSRSEIDLFNIRKEFRKNFATSLYSMIKGDTSGDYKKALLLLCG    EDD*
beta  F..R..........R.G....NI........NL.KCH.K.MYGKT.S...ME.......N...S.V.    S.P*
```

FIG.11

Comparison of VAC-alpha and beta cDNA

```
VA          ATGGCACAGGTTCTCAGAGGCACTGTGACTGACTTCCCTGGA           42
VB  ATGGCCTGGTGGAAAGCCTG.ATTG.ACAGGAGG.T.T...A....AGAG.AG.T.CCAC  60

VA  TTTGATGAGCGGGCTGATGCAGAAACTCTTCGGAAAGGCTATGAAAGGCTTGGGCACAGAT  102
VB  ..CA.CCCAGACC..........G..C...CTAC..A..C.....G..GA.C..G..CA.C  120

VA  GAGGAGAGCATCCTGACTCTGTTGACATCCCGAAGTAATGCTCAGCGCCAGGAAATCTCT  162
VB  ...C..GCT...A.CGA.G..C.C..CAAGA....C..CA.G.....G...C.G...G.C  180

VA  GCAGCTTTTAAGACTCTGTTTGGCAGGGATCTTCTGGATGACCTGAAATCAGAACTAACT  222
VB  AAGT.C..C...G...A...C....A...C..CACT..G.C.T....G..T..G..C.G.  240

VA  GGAAAATTTGAAAAATTAATTGTGGCTCTGATGAAACCCTCTCGGCTTTATGATGCTTAT  282
VB  ..C..G.....G.GGC.C........C..T...T.T..GC.ATACAGA..C..A..CA.G  300

VA  GAACTGAAACATGCCTTGAAGGGAGCTGGAACAAATGAAAAAGTACTGACAGAAATTATT  342
VB  ..G...C.TG.C...A......CTTA.....C..G..GGGT..CA.C.TT..G..CC.G  360

VA  GCTTCAAGGACACCTGAAGAACTGAGAGCCATCAAACAAGTTTATGAAGAAGAATATGGC  402
VB  ..C..TC....CAAGA.CC.G...C.G.AG..A.TGA.G.CG.....G.....C.....G  420

VA  TCAAGCCTGGAAGATGACGTGGTGGGGGACACTTCAGGGTACTACCAGCGGATGTTGGTG  462
VB  ..C........G..G...A.CCAA.CA.....AAGT..C...CTGG..A....CC.....  480

VA  GTTCTCCTTCAGGCTAACAGAGACCCTGATGCTGGAATTGATGAAGCTCAAGTTGAACAA  522
VB  TGC.....G....GC.G...G..TGA..TGAGCA.CT...TG..CCCGGC.C.G.CC.TC  540

VA  GATGCTCAGGCTTTATTTCAGGCTGGAGAACTTAAATGGGGGACAGATGAAGAAAAGTTT  582
VB  C.A.ACGCACAGGATC.GT.T..G.C..GCGAG..GATTC.TGGGAC...T..G.T.AAA  600

VA  ATCACCATCTTTGGAACACGAAGTGTGTCTCATTTGAG...AAAGGTGTTTGACAAGTAC  639
VB  T...T..C.A.CCTGTGCACGC.CAGTG.CAC.CACCTGCTG.GA........AG....T  660
```

FIG.12A

```
VA  ATGACTATATCAGGATTTCAAATTGAGGAAACCATTGACCGCGAGACTTCTGGCAATTTA    699
VB  GA..AA..TG.CAACAAGAGC........C.G...CA.GA.T.....CCA....TCAC.G    720

VA  GAGCAACTACTCCTTGCTGTTGTGAAATCTATTCGAAGTATACCTGCCTACCTTGCAGAG    759
VB  ...G.GGCCA.G..CA....G.......GC.CC.A..ACC.C.ACAG....T........    780

VA  ACCCTCTATTATGCTATGAAGGGAGCTGGGACAGATGATCATACCCTCATCAGAGTCATG    819
VB  .GA.....C....CC...........A.....GCG....GGG.....G..A...AA...C    840

VA  GTTTCCAGGAGTGAGATTGATCTGTTTAACATCAGGAAGGAGTTTAGGAAGAATTTTGCC    879
VB  .....A.....C........CT.AAA.CTT....AATGTC.C..C.A.....TG.AC.G.    900

VA  ACCTCTCTTTATTCCATGATTAAGGGAGATACATCTGGGGACTATAAGAAAGCTCTTCTG    939
VB  .AGA.C..CAGCAG......C.T..A...C..CAGC..C.....C.....C..C..G...    960

VA  CTGCTCTGTGGAGAAGATGAC                                           960
VB  AGC..GGTG..CAGC..CCC.                                           981
```

FIG. 12B

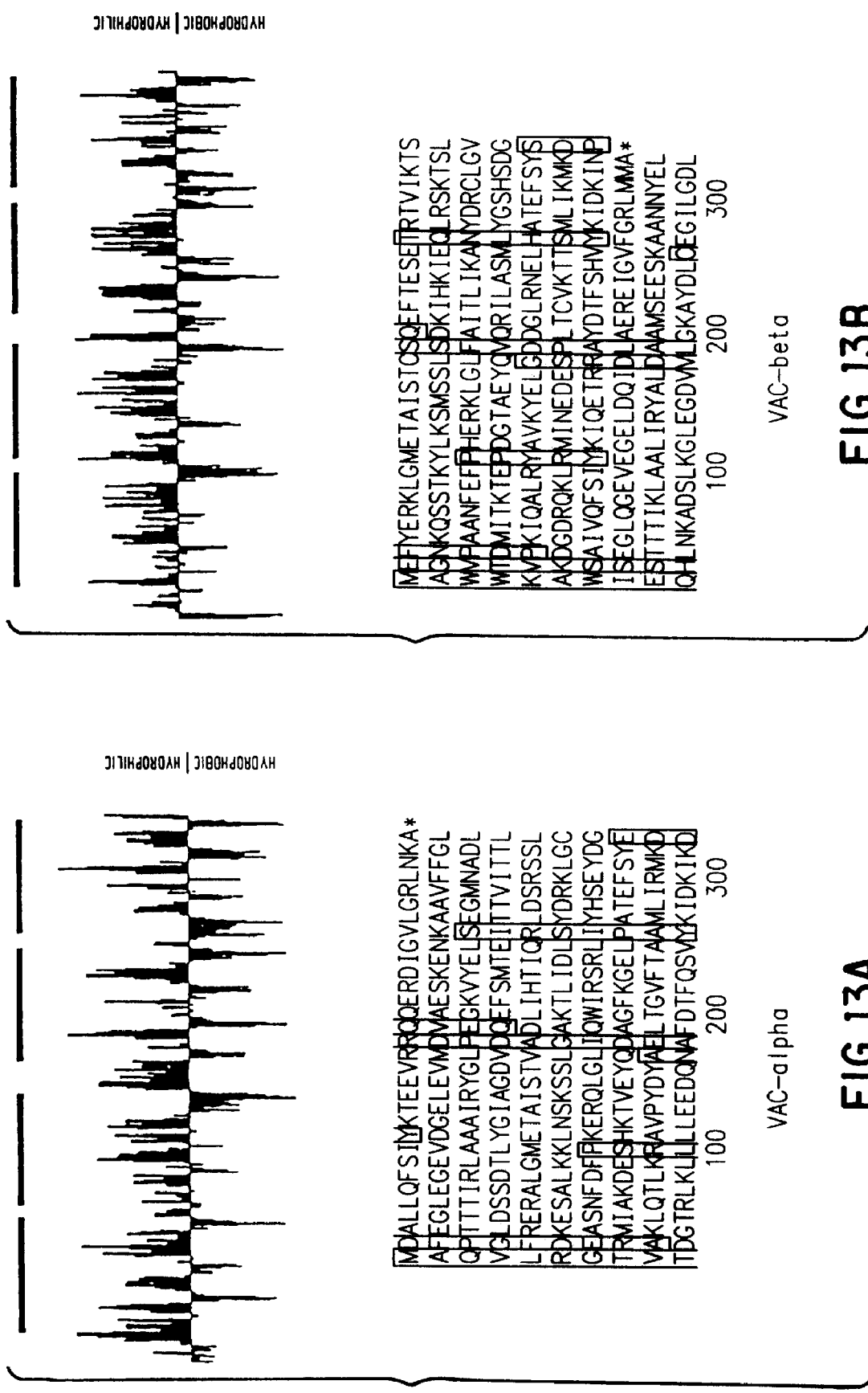
FIG. 13B VAC-beta
FIG. 13A VAC-alpha

```
Comparison VAC/VAC-beta/Lipocortin I/Lipocortin II

VA                                                 MAQVLRGTVTDFPGFDERA
VB                                       MAWWKAWIEQEGVTVKSSSHFNPDP
LCI                        MAMVSEFLKQAWFIENEEQEYVQTVKSSKGGPGSAVSPYPTFNPSS
LCII                          MSTVHEILCKLSLEGDHSTPPSAYGSVKPYTNFDAER

VA    DAETLRKAMKGLGTDEESILTLLTSRSNAQRQEISAAFKTLFGRDLLDDLKSERTGKFEKLIVALMK       PSRLY
VB    DAETLYKAMKGIGTNEQAIIDVLTKRSNTQRQQIAKSFKAQFGKDLTETLKSELSGKFERLIVALMY       PPYRY
LCI   DVAALHKAIMVKGVDEATIIDILTKRNNAQRQQIKAAYLQETGKPLDETLKKALTGHLEEVLALLK         TPAQF
LCII  DALNIETAVKTKGVDEVTIVNILTNRSNVQRQDIAFAYQRRTKKELPSALKSALSGHLETVILGLLK        TPAQY

VA    DAYELKHALKGAGTNEKVLTEIIASRTPEELRAIKQVYEEEYGSSLEDDVVGDTSGYYQRMLVVLLQ        ANRDPDAG-IDEAQVEQ
VB    EAKELHDAMKGLGTKEGVIIEILASRTKNQLREIMKAYEEDYGSSLEEDIQADTSGYLERILVCLLQ        GSRDDVSSFVDPALALQ
LCI   DADELRAAMKGLGTDEDTLIEILASRTNKEIRDINRVYREELKRDLAKDITSDTSGDFRNALLSLAK        GDRSEDFGVNED-LADS
LCII  DASELKASMKGLGTDEDSLIEIICSRTNQELQEINRVYKEMYKTDLEKDIISDTSGDFRKLMVALAK        GRRAEDGSVIDYELIDQ

VA    DAQALFQAGELKWGTDEEKFITIFGTRSVSHLRKVFDKYMTISGFQIEETIDRETSGNLEQLLAVVK        SIRSIPAY
VB    DAQDLYAAGEKIRGTDEMKFITILCTRSATHLLRVFEEYEKIANKSIEDSIKSETHGSLEEAMLTVVK       CTQNLHSY
LCI   DARALYEAGERRKGTDVNVFNTILTTRSYPQLRRVFQKYTKYSKHDMNKVLDLELKGDIEKCLTAIVK       CATSKPAF
LCII  DARELYDAGVKRKGTDVPKWISIMTERSVCHLQKVFERYKSYSPYDMLESIKKEVKGDLENAFLNLVQ       CIQNKPLY

VA    LAETLYYAMKGAGTDDHTLIRVMVSRSEIDLFNIRKEFRKNFATSLYSMIKGDTSGDYKKALLLLCG        EDD*
VB    FAERLYYAMKGAGTRDGTLIRNIVSRSEIDLNLIKCHFKKMYGKTLSSMIMEDTSGDYKNALLSLVG        SDP*
LCI   FAEKLHQAMKGVGTRHKALIRIMVSRSEIDMNDIKAFYQKMYGISLCQAILDETKGDYEKILVALCG        GN*
LCII  FADRLYDSMKGKGTRDKVLIRIMVSRSEVDMLKIRSEFKRKYGKSLYYIQQDTKGDYQKALLYLCG         GDD*

VA   :  human  VAC-alpha
VB   :  human  VAC-beta
LCI  :  human  Lipocortin I
LCII :  human  Lipocortin II
```

FIG. 14

Sequence of the alkaline phosphatase gene component in plasmid pRH284T

```
         10        20        30        40        50        60
AATTGGAGATTATCGTCACTGCAATGCTTCGCAATATGGCGCAAAATGACCAACAGCGGT
  CCTCTAATAGCAGTGACGTTACGAAGCGTTATACCGCGTTTTACTGGTTGTCGCCA 70        80        90       100       110       120
TGATTGATCAGGTAGAGGGGGCGCTGTACGAGGTAAAGCCCGATGCCAGCATTCCTGACG
ACTAACTAGTCCATCTCCCCCGCGACATGCTCCATTTCGGGCTACGGTCGTAAGGACTGC 130       140       150       160       170       180
ACGATACGGAGCTGCTGCGCGATTACGTAAAGAAGTTATTGAAGCATCCTCGTCAGTAAA
TGCTATGCCTCGACGACGCGCTAATGCATTTCTTCAATAACTTCGTAGGAGCAGTCATTT 190       200       210       220       230       240
AAGTTAATCTTTTCAACAGCTGTCATAAAGTTGTCACGGCCGAGACTTATAGTCGCTTTG
TTCAATTAGAAAAGTTGTCGACAGTATTTCAACAGTGCCGGCTCTGAATATCAGCGAAAC 250       260       270       280       290       300
TTTTTATTTTTTAATGTATTTGCTCGAGAGGTTGAGGTGATTTTATGAGCTCGAATTCAT
AAAAATAAAAAATTACATAAACGAGCTCTCCAACTCCACTAAAATACTCGAGCTTAAGTA
                      XhoI       RBS        SacI EcoRI C 310       320       330       340       350
CGATAAGCTTGGATCCGTCGACCGCGCCCGGCAGTGAATTTTCGCTGCCGGGTGGTTTTT
GCTATTCGAACCTAGGCAGCTGGCGCGGGCCGTCACTTAAAAGCGACGGCCCACCAAAAA
laI HindIIIBamHi SalI 360       370
TTGCTGC
AACGACGAGCT
```

FIG. 15

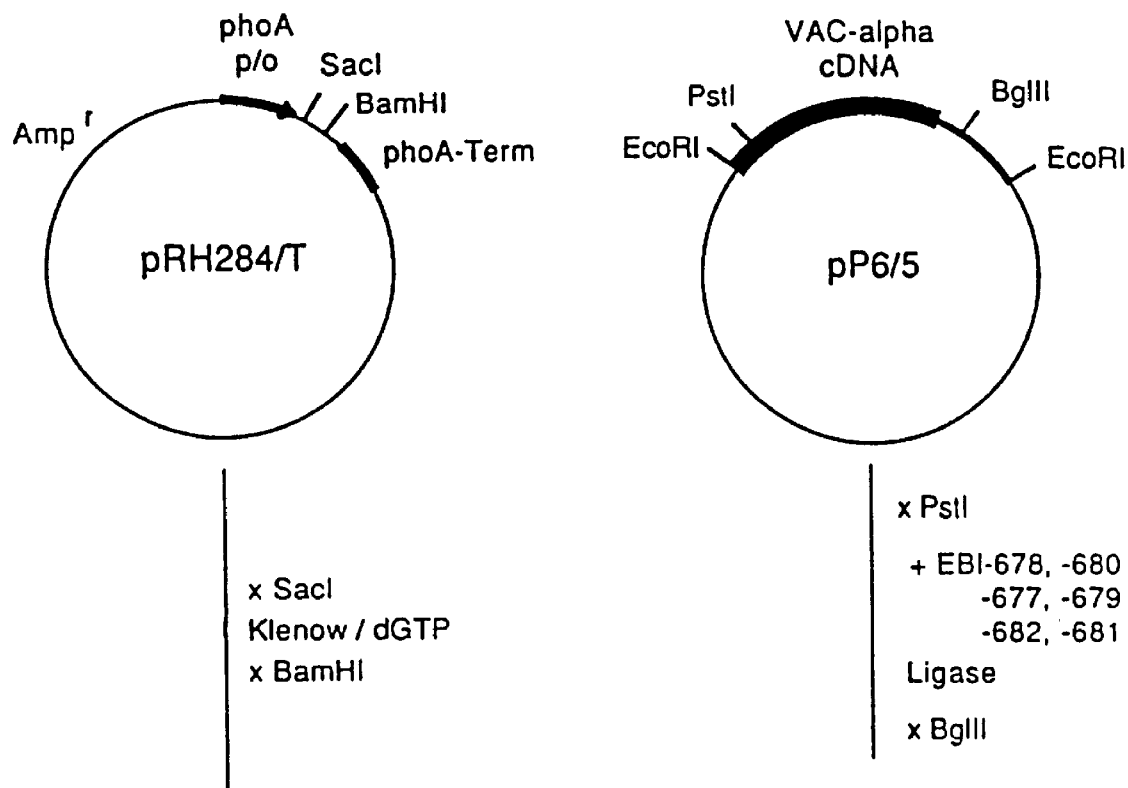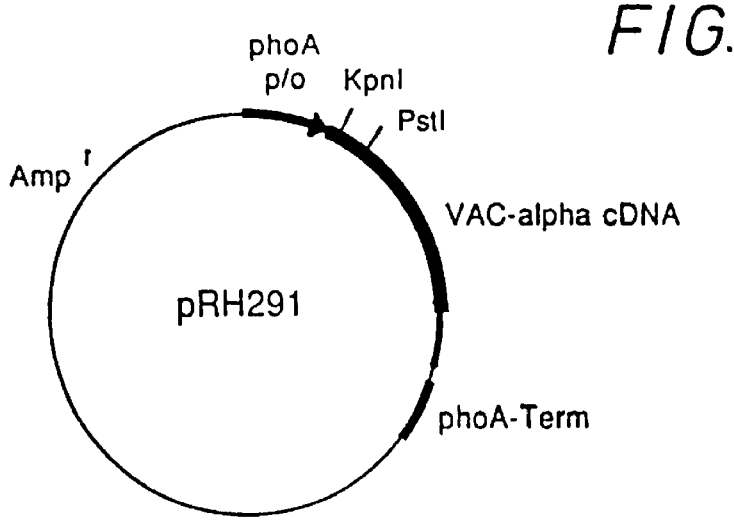
FIG. 18.

Coomassie staining

Figure 39:
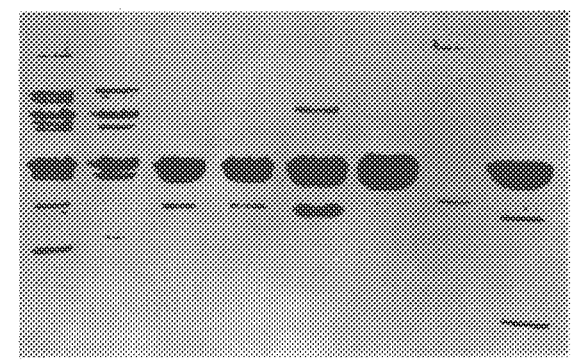

4. VAC β in process sample     FIG. 39.

15 % SDS-PAGE
+ DTT

DEAE-FF POOL:
- 10 μg DEAE load
- 4 μg DEAE DL
- 10 μg DEAE Fr. 40-59

POOL CONCENTRATE:
- 10 μg S200 load

VAC-β SEPHACRYL POOL:
- 10 μg S200 Fr. 31+32
- 10 μg S200 Fr. 33-37

LMW - Marker

- 10 μg VACβ-3(10)(12/87)

01-FEB-88          BECKMAN AMINO ACID ANALYSIS

```
      SAMPLE              : 3 vacb
      RUN NUMBER          : 22
      PROTEIN             : VAC 'beta'
      CHROMATOGRAM OF     : 21.04.88  3:17:36
      INJECTION VOLUME    : 50 µl
      STANDARD VALUE      : AVERAGES OF RUN 22
```

| NAME | ACTUAL [in nMol] | NOMINAL | REL. ACTUAL [I] | REL. ACTUAL [II] | REL. NOMINAL |
|---|---|---|---|---|---|
| ASP | 14.07 | 29 | 29.59 | 6.35 | 7.25 |
| THR | 11.15 | 21 | 23.45 | 5.03 | 5.25 |
| SER | 12.34 | 27 | 25.96 | 5.57 | 6.75 |
| GLU | 19.97 | 41 | 41.99 | 9.01 | 10.25 |
| PRO | 5.38 | 6 | 11.31 | 2.43 | 1.50 |
| GLY | 11.94 | 20 | 25.12 | 5.39 | 5.00 |
| ALA | 12.19 | 25 | 25.63 | 5.50 | 6.25 |
| CYS | 2.22 | 4 | 4.66 | 1.00 | 1.00 |
| VAL | 5.86 | 13 | 12.32 | 2.64 | 3.25 |
| MET | 4.61 | 10 | 9.69 | 2.08 | 2.50 |
| ILE | 9.79 | 23 | 20.58 | 4.41 | 5.75 |
| LEU | 15.69 | 33 | 33.00 | 7.08 | 8.25 |
| TYR | 6.55 | 14 | 13.77 | 2.95 | 3.50 |
| PHE | 4.40 | 9 | 9.25 | 1.98 | 2.25 |
| HIS | 2.75 | 6 | 5.79 | 1.24 | 1.50 |
| LYS | 12.56 | 27 | 26.42 | 5.66 | 6.75 |
| NH3 | 18.43 | 0 | 38.77 | 8.31 | 0.00 |
| ARG | 7.23 | 15 | 15.20 | 3.26 | 3.75 |

| NAME | NOMINAL | CORR ACTUAL | ROUNDED ACTUAL | DEVIATION | % DEVIATION |
|---|---|---|---|---|---|
| ASP | 29 | 29.23 | 29 | + 0.225 | 0.777 |
| THR | 21 | 23.16 | 23 | + 2.159 | 10.283 |
| SER | 27 | 25.64 | 26 | − 1.361 | 5.042 |
| GLU | 41 | 41.48 | 41 | + 0.478 | 1.167 |
| PRO | 6 | 11.17 | 11 | + 5.174 | 86.238 |
| GLY | 20 | 24.81 | 25 | + 4.806 | 24.032 |
| ALA | 25 | 25.31 | 25 | + 0.315 | 1.260 |
| CYS | 4 | 4.61 | 5 | + 0.606 | 15.150 |
| VAL | 13 | 12.17 | 12 | − 0.828 | 6.366 |
| MET | 10 | 9.57 | 10 | − 0.426 | 4.256 |
| ILE | 23 | 20.33 | 20 | − 2.674 | 11.626 |
| LEU | 33 | 32.59 | 33 | − 0.406 | 1.229 |
| TYR | 14 | 13.60 | 14 | − 0.401 | 2.862 |
| PHE | 9 | 9.13 | 9 | + 0.132 | 1.472 |
| HIS | 6 | 5.72 | 6 | − 0.285 | 4.748 |
| LYS | 27 | 26.09 | 26 | − 0.908 | 3.363 |
| NH3 | 0 | 38.29 | 0 | 0.000 | 0.000 |
| ARG | 15 | 15.01 | 15 | + 0.014 | 0.093 |

```
      AS - NOM. VALUE              : = 323
      AS - ACTUAL VALUE            : = 330
      TOTAL DEVIATION              : = 21.20 AS  /  6.56%
      AVERAGE AMOUNT PROTEIN       : = 0.510 nanoMol
      ALA/LEU - PROTEIN AMOUNT     : = 0.482 nanoMol
```

| | | | |
|---|---|---|---|
| Acquisition method | ninrept | Quantitation method | ninrept |
| Units | None | System number | 2 |
| Channel | 1 | Vial | -1 |
| Injection | -1 | Total injections | -1 |
| Run time | 60.00 min | Sample rate | 2 per sec |
| Injection volume | -1 μL | Sample amount | 1.00 |
| Internal standard amt | 1.00 | Scale factor | 1.00 |
| Mode | Analysis | Response factors | Replace |
| Version | REV4.0 | Channel to calibrate | 1 |
| Description | | | |

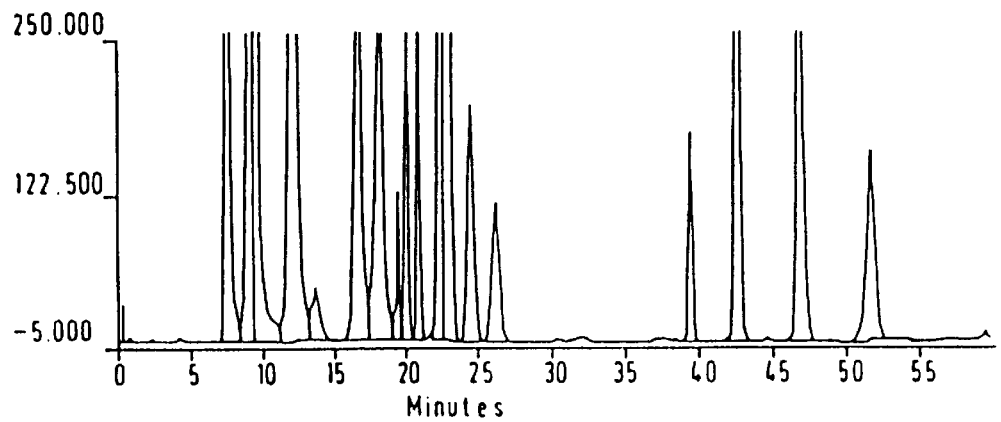

| Peak Name | Ret time | Area | Height | Type | Amount | RF |
|---|---|---|---|---|---|---|
| ASP | 7.67 | 12949108 | 589326 | ** | 10.797 | 1.1993e+06 |
| THR | 9.13 | 9054415 | 359489 | ** | 7.982 | 1.1344e+06 |
| SER | 9.67 | 13162093 | 508590 | ** | 9.327 | 1.4112e+06 |
| GLU | 12.20 | 21594486 | 581113 | ** | 15.972 | 1.3520e+06 |
| PRO | 13.73 | 1915875 | 42433 | ** | 4.469 | 4.7872e+05 |
| GLY | 16.80 | 12516849 | 365363 | ** | 9.017 | 1.3882e+06 |
| ALA | 18.27 | 11691803 | 288180 | ** | 9.471 | 1.2345e+06 |
| CYS | 19.60 | 1605991 | 124559 | ** | 0.864 | 1.8584e+06 |
| VAL | 20.13 | 5326578 | 424585 | ** | 4.445 | 1.1982e+06 |
| MET | 20.93 | 4866785 | 296576 | ** | 3.498 | 1.3911e+06 |
| ILE | 22.47 | 9170982 | 414630 | ** | 7.277 | 1.2603e+06 |
| LEU | 23.07 | 16274567 | 687357 | ** | 11.841 | 1.3744e+06 |
| TYR | 24.60 | 6190710 | 195610 | BB | 4.916 | 1.2593e+06 |
| PHE | 26.33 | 4001320 | 114100 | BB | 3.306 | 1.2105e+06 |
| HIS | 39.53 | 3146100 | 178088 | BB | 2.111 | 1.4904e+06 |
| LYS | 42.73 | 16208683 | 645200 | BB | 9.546 | 1.6980e+06 |
| NH3 | 46.93 | 13233695 | 414891 | BB | 10.856 | 1.2190e+06 |
| ARG | 51.87 | 6455633 | 155589 | BB | 5.202 | 1.2409e+06 |

Sample: 3.VACβ * S2ØØ * FR 54-5P

| SEQUENCER PROGRAM: 3PAPTH | Degradation steps: 1→3P | PTH-AS-HPLC up to degradation step No.3P | PTH-AS detectable up to degradation step No.3P |
|---|---|---|---|

36µg [N/nmol] SAMPLE DISSOLVED IN 75µl Ø.1%TFA ; 3×25µl AM APPLIED TO SEQUENCER

SEQUENCE:

```
                1      2      3      4      5      6      7      8      9      10
AS: 1-10  I.  X_ALA^1)-TRP - TRP - LYS -X_ALA^1)-TRP -ILE -(GLU)^2)-GLN -(GLU)^2)-
AS:11-20  I.  GLY  - VAL - THR - VAL - LYS - SER -SER -SER - HIS^3)-(PHE)-
AS:21-3Ø  I.  ASN  - PRO -(ASP)^4)-PRO -(ASP) -X_ALA^1)-X_GLU -THR - LEU - TYR-
AS:31-4Ø  I.  LYS -X_ALA^1)-MET -(LYS)-GLY - ILE - GLY -(THR)-ASN-
```

1) PTH-ALA detection perturbed by DMPTU (up to 12 000 000 IV(ASB)≙nmol PTH-AS
2) Retention times shifted from 1·95' to 2·45'             [SEQUENCER DEFECT!]
3) ——————— " ——————— 5·5Ø' to 4·8Ø'
4) ——————— " ——————— 1·66' to 1·87'

Estimation of Quantities

| Component | Amino acid from | to | Quantity (nmol) | Proportion (%) |
|---|---|---|---|---|
| I | 1 | (3P) | ~Ø.45 | / |
| II | | | | |
| III | | | | |
| IV | | | | |
| V | | | | |
| VI | | | | |
| VII | | | | |
| VIII | | | | |

Total quantity: ~Ø.45nmol
(Calculated from ILE 7-8, 80% R.Y.)

Compare with: 124Ø

FIG. 44.

VAC β Standard comparison
12.5% SDS PAGE
Coomassie staining

<u>ISOELECTRIC FOCUSSING (PAGIF)</u> pH-Range: 3.5 – 9.5
Manuf of plates : LKB-PAG plate
Electrode Solutions: Anode 1M Phosphoric acid
    Cathode 1M Sodium hydroxide
Running time: Prefocussing 500 Vh
    Focussing 3000 Vh — IEF-Marker
— 22μg VAC β-4
— 11μg VAC β-4
— 18μg VAC β-4 + DTT
— 9μg VAC β-4 + DTT
— IEF-Marker VAC β-4 : 1. Main band pI 5.35
    2. Main band pI 5.45 + DTT

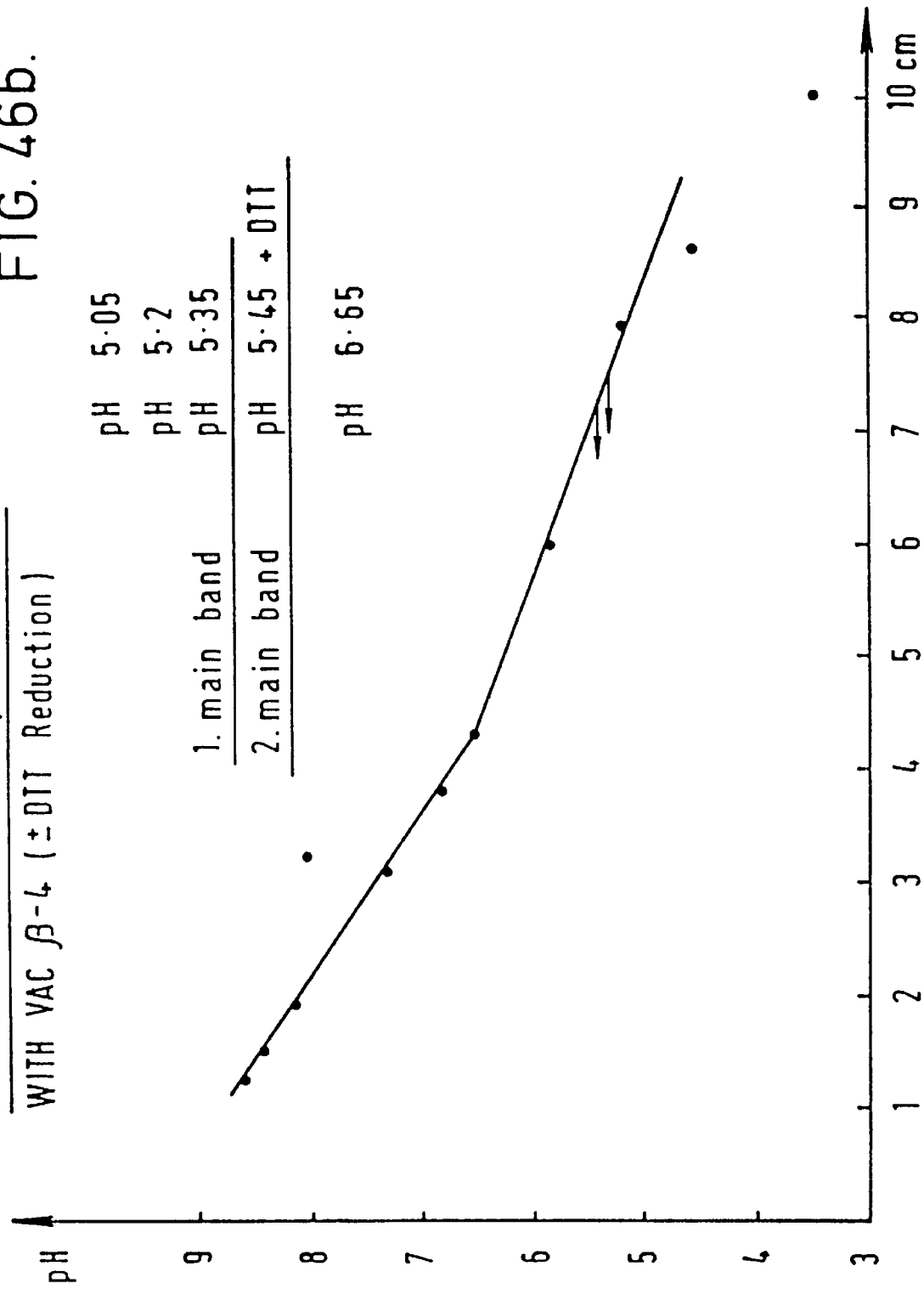

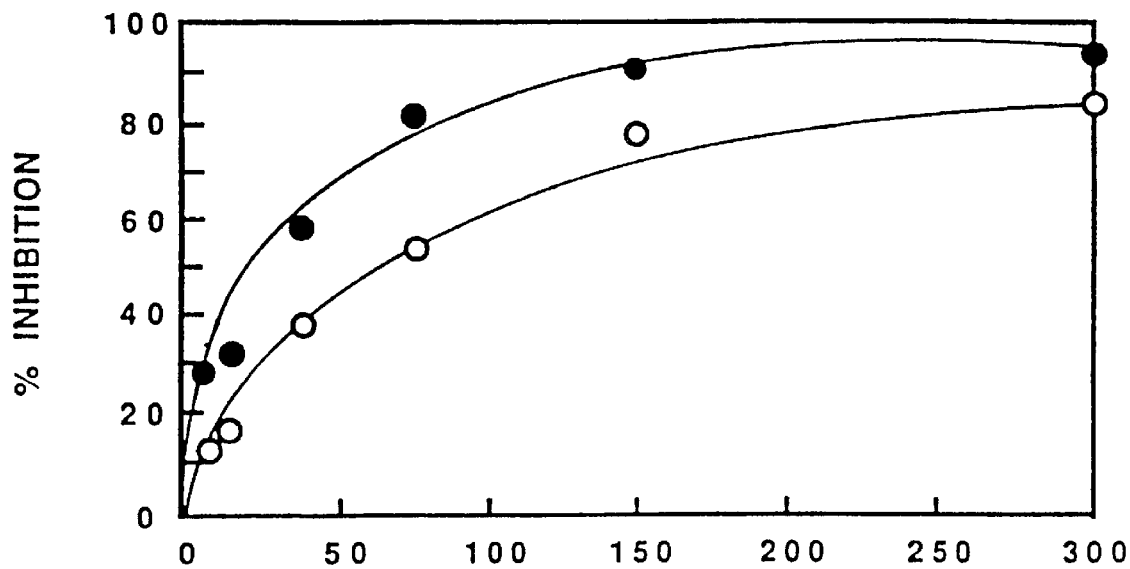
FIG. 48.   VACα (nM)
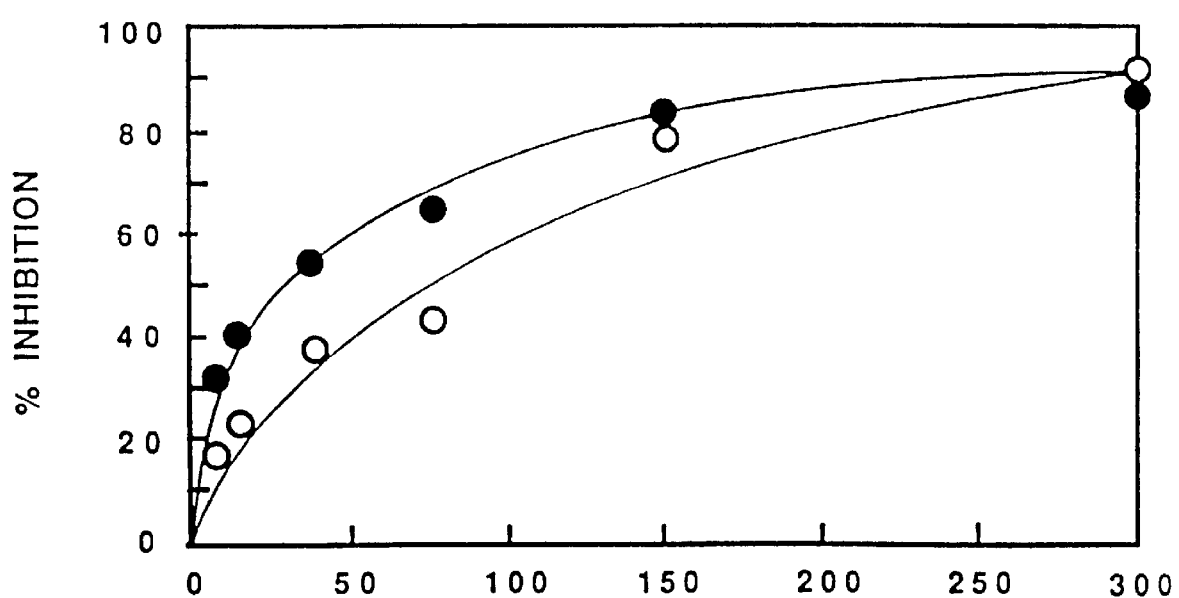
FIG. 49.   VACβ (nM)

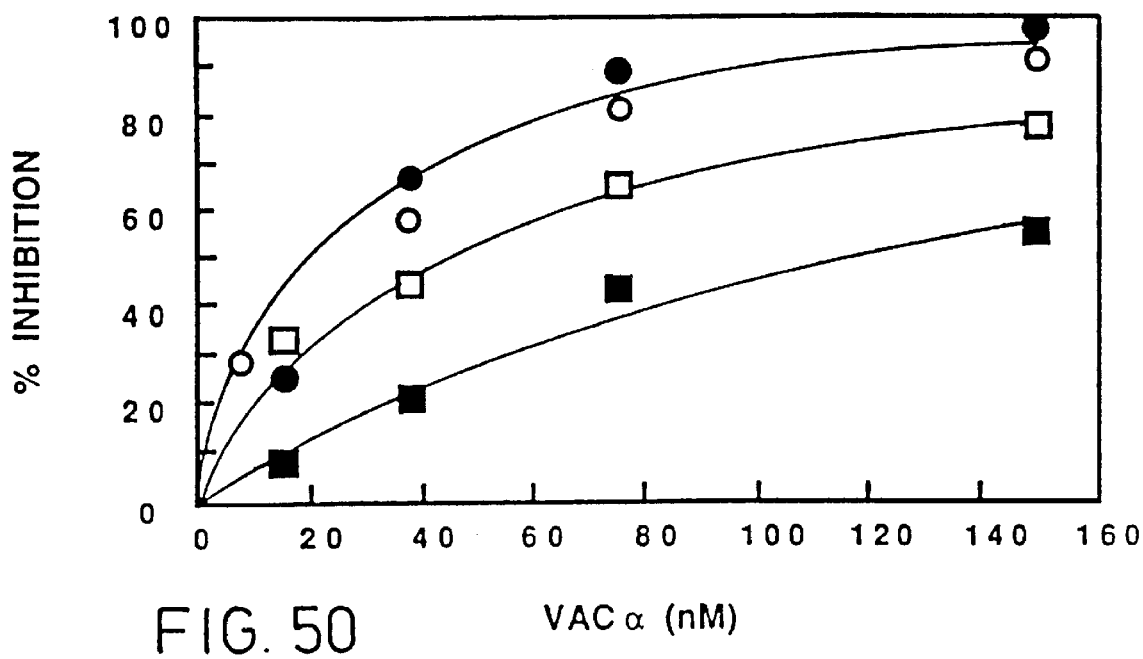
FIG. 50  VACα (nM)
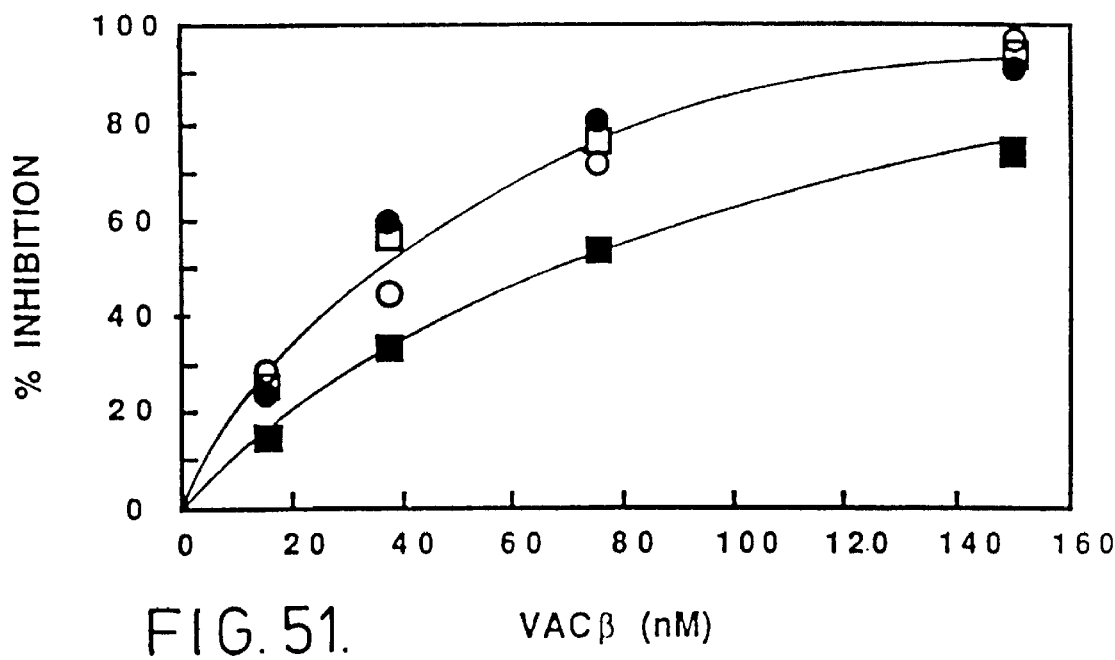
FIG. 51.  VACβ (nM)

VASCULAR ANTICOAGULANT PROTEINS DNA WHICH CODES THEM, PROCESSER FOR PREPARING THEM AND THEIR USE

This application is a divisional of application Ser. No. 08/230,875, filed Apr. 20, 1994, which is a continuation of application Ser. No. 07/868,337, filed Apr. 7, 1992, which is a division of application Ser. No. 07/294,602, filed Jan. 30, 1989, all now abandoned.

BACKGROUND OF THE INVENTION

1. Field of the Invention

The present invention relates to biologically active proteins, the DNA molecules coding for them, processes for preparing them and their use.

2. Brief Description of the Background Art

In the majority of mammals there are proteins which have coagulation-inhibiting properties. These proteins can be divided up into three groups, these divisions being based on the different mechanisms of activity.

1. Proteins which form a complex with the coagulation factor and thereby render the coagulation factor ineffective. These include the proteins:
  a) Antithrombin-III (Thromb.Res.5, 439–452 (1974))
  b) $\alpha_1$-protease inhibitor (Ann. Rev. Biochem. 52, 655–709 (1983))
  c) $\alpha_2$-macroglobulin (Ann. Rev. Biochem. 52, 655–709 (1983))
  d) $C_1$-inhibitor (Biochemistry 20, 2738–2743 (1981))
  e) Protease nexin (J. Biol. Chem. 258, 10439–10444, (1983)).

2. Proteins which proteolytically cut a coagulation factor and thereby deactivate the coagulation factor. The only protein of this kind which has hitherto been described is Protein C (J. Biol. Chem. 251, 355–363, (1976)).

3. Proteins which screen and/or hydrolyze the negatively charged phospholipids, so that the phospholipid-dependent reactions of the blood coagulation mechanism are inhibited. Hitherto, only phospholipases isolated from various types of snake venom have been described (Eur. J. Biochem. 112, 25–32 (1980)).

The coagulation system, which proceeds step by step, has been intensively investigated in recent years. It is understood to be a self-intensifying multi-stage system of various, interlinked proteolytic reactions in which an enzyme converts a zymogen into the active form (cf. Jackson C. M., Nemerson Y., Ann. Rev. Biochem. 49, 765–811, (1980)). The speed of this reaction is decisively increased by the presence of phospholipids and other cofactors such as factor $V_a$ and factor $VIII_a$. In vivo, the procoagulation reactions are regulated by various inhibition mechanisms which prevent an explosively thrombotic trauma after slight activation of the coagulation cascade.

The anticoagulation mechanisms can be divided up as follows (Rosenberg, R. D., Rosenberg, J. S., J. Clin. Invest. 74, 1–6 (1984)):

1. The serine-protease factor $X_a$ and thrombin are deactivated as a result of their binding to antithrombin III or to the antithrombin/heparin complex. Both the prothrombin activation and also the formation of fibrin can be inhibited in this way. In addition to antithrombin III there are various other plasma protease inhibitors such as for example $\alpha_2$-macroglobulin and antitrypsin, the activity of which is dependent on time.

2. The discovery of protein C led to the discovery of another anticoagulation mechanism. Once protein C has been activated, it acts as an anticoagulant by selective proteolysis of the protein cofactors factor $V_a$ and $VIII_a$, by which prothrombinase and the enzyme which converts factor X are deactivated.

3. Plasmin cleaves monomeric fibrin 1, a product of the effect of thrombin on fibrinogen, thereby preventing the formation of an insoluble fibrin (Nossel, H. L., Nature, 291, 165–167 (1981)).

Of the above-mentioned native proteins involved in the coagulation process, at present only antithrombin III is in clinical use. However, the use of this protein has been found to have the serious disadvantage of increasing the tendency to bleeding.

All the substances hitherto used as anticoagulants, whether of native or synthetic nature, render the coagulation factors inactive in some way and thereby lead to side effects which may have a disadvantageous effect on the coagulation process.

Surprisingly, in addition to these proteins, it has now been possible to isolate other substances native to the body which have the desired coagulation-inhibiting properties under particular conditions but do not increase the risk of bleeding. When considerable bleeding occurs, these proteins lose their coagulation-inhibiting properties and thus do not interfere with the coagulation processes necessary to survival in such cases. Since they were first isolated from strongly vascularized tissue, they were known as "vascular anticoagulating proteins", VAC.

The proteins isolated from strongly vascularized tissues such as umbilical cord vessels and placenta have molecular weights of about $70 \times 10^3$, about $60 \times 10^3$, about $34 \times 10^3$ and about $32 \times 10^3$, while the substances with molecular weights of 34 and $32 \times 10^3$, respectively, consist of a single polypeptide chain. The exact biochemical characterisation of these proteins and their isolation and purification can be found in EP-A-0181465 of 21st May 1986.

Proteins with VAC activity are natural blood coagulation inhibitors which intervene in the blood coagulation cascade at two points.

In the first instance, they have an inhibiting effect on the activation of factor X to Xa, catalyzed by factors IXa and VIIIa, and in the second instance they prevent the cleavage of prothrombin to form thrombin, which is mediated by factors Xa and Va. Something which is common to both activation steps is the fact that they require calcium ions and phospholipids. Obviously, VAC proteins may also interact with phospholipids and by this binding action block the activation steps of the coagulation factors.

Their properties make these proteins interesting and pharmacologically extremely valuable active substances. However, in order to have sufficient quantities of them available in highly purified form it is necessary to produce them by methods other than the purification of protein from natural tissue. The genetic engineering method would appear to be the solution.

SUMMARY OF THE INVENTION

The aim of the present invention was therefore to produce proteins with a VAC activity by genetic engineering.

BRIEF DESCRIPTION OF THE PREFERRED EMBODIMENTS

This aim was achieved by ascertaining the amino acid sequence of parts of the proteins with VAC activity which are isolated from strongly vascularized tissue and highly purified (EPA 0 181 465), preparing synthetic DNA probes using these sequences and investigating cDNA libraries therewith. After isolation of cDNA hybridizing with the probes, sequence determination and suitable manipulation, this cDNA was expressed in suitable host systems, for example in bacteria, yeast or mammalian cells.

One of the purified proteins was enzymatically cleaved with trypsin. The peptides formed were separated and selected fragments were sequenced. However, the sequence of the N-terminus defied direct analysis since the first amino acid is obviously blocked.

The sequence information is given in FIG. 0.1.

A suitable DNA probe can be produced basically by three methods. If a fairly long section of the protein, roughly 30 or more amino acids long, is known, it is possible to establish a fairly probable sequence for the corresponding mRNA section, taking into account the codons preferably used in mammals. A probe of this kind is, in the worst instance, about 66% homologous with the actual sequence. This is the reason why the probe has to be relatively long so as to be able to hybridize under non-stringent conditions.

The second possibility is to synthesize all the conceivable variations of oligonucleotides for a short peptide section, roughly six to seven amino acids long. If such complex mixtures are used in the investigation of cDNA libraries, a relatively large number of "false" positive-reacting clones may be isolated. Furthermore, the hybridization signal may be very weak, since the single oligonucleotide which fits perfectly will make up only a small part of the total mixture.

The third method admittedly does not get around the variability of an oligonucleotide probe but, by the choice of a special nucleoside triphosphate (ITP) it does ensure that all the molecules of the probe can bind to the cDNA sought (or also to "false" cDNA). Thus, oligonucleotides 23 bases long corresponding to the tryptic peptide [P30/I] have been synthesized using inosine triphosphate.

As already mentioned, VAC proteins may be isolated from strongly vascularized tissue. The ideal tissues are umbilical cord vessels or placenta. Therefore, and since it is known that almost all genes are expressed in the placenta, by contrast with other special tissues, the above-mentioned DNA probes were used to investigate a placental cDNA library which had been prepared from placental tissue in a manner known per se, to search for cDNA molecules which code for VAC proteins.

In order to search the cDNA library for cDNA which codes for VAC protein, two oligonucleotides were synthesized corresponding to the sequences of tryptic peptide P16/II and one oligonucleotide was synthesized for the sequences of Staph A peptide P20/I/6 (FIG. 1). These oligonucleotides are each mixtures of all the variants which take into account every coding possibility of the corresponding mRNA. EBI-386 has 512 variations with a chain length of 20 nucleotides and fits the Staph-A peptide P20/I/6. In order to keep the variation lower in the oligonucleotide for the tryptic peptide P16/II, two oligonucleotides (20-mers) were synthesized: EBI-387: 128 variations and EBI-388: 64 variations.

Furthermore, two oligonucleotides were synthesized corresponding to the tryptic VAC peptide P30/I, using desoxyinosine as the base in "wobble" positions (FIG. 2): EBI-118 and EBI-119. This substitution has been described by E. Ohtsuka et al., J. Biol. Chem. 260/5 (1985), pp. 2605–2608, and Y. Takahashi et al., Proc. Nat. Acad. Sci. (1985) pp.1931–1935. Inosine base-pairs well with cytosine, but hardly interferes with the formation of the double helix when other nucleotides are offered as partners.

After each of these oligonucleotides had been radioactively labelled in known manner, extracts from phage plates were hybridized therewith by known methods.

Hybridization with EBI-386, 387 and 388 produced the phages lambda-P11/3, lambda-P6/5 and lambda-P6/6. Hybridization with EBI-118 and 119 resulted in the phages lambda-Nr15, lambda-Nr19 and lambda-Nr22.

The DNAs isolated from the phages were cut with EcoRI and the fragments produced were isolated.

The cDNA inserts of the clones lambda-P11/3, lambda-P6/5 and lambda-P6/6 had sizes of approximately 1300 to 1400 bp. The sequence analysis showed that all three clones were derived from one and the same mRNA. However, the 5' end of the mRNA was missing in the cDNAs. The inserts of the phages lambda-Nr15, lambda-Nr19 and lambda-Nr22 had lengths of approximately 1600, 1100 and 1000 bp. Sequence analysis indicated an approximately complete cDNA.

The cDNAs of the two phage groups lambda-P11/3, lambda-P6/5 and lambda-P6/6 and lambda-Nr15, lambda-Nr19 and lambda-Nr22 are derived from two different mRNAs, as was shown by the sequence analysis. The EcoRI inserts of the three clones lambda-P11/3, lambda-P6/5 and lambda-P6/6 were isolated and ligated into the EcoRI-cut Bluescribe M13$^+$ vector (Vector Cloning Systems, 3770 Tansy Street, San Diego, Calif. 92121, USA). The resulting clones were designated pP6/5, pP6/6 and pP11/3.

The EcoRI inserts of the three clones lambda-Nr15, lambda-Nr19 and lambda-Nr22 were isolated and ligated into the EcoRI-cut Bluescribe M13$^+$ vector. The resulting clones were designated pRH201, pRH202 and pRH203.

In order to obtain other cDNA clones, the human placental lambda-gt10 library was investigated once more, this time with the radioactively labelled EcoRI insert of pP11/3, as the probe.

In all, 69 positively-reacting clones were obtained (lambda-VAC1 to lambda-VAC69).

12 of these clones were prepared on a small scale as described above, the cDNA inserts were freed with EcoRI and isolated. It was found that the insert of the clone lambda-VAC10 contains the entire reading frame coding for VAC protein. In order to characterize the cDNAs which code for VAC-alpha and VAC-beta, a Northern blot experiment, sequence analyses and a genomic Southern blot analysis were carried out.

The results are shown in FIG. 3. The cDNA of the clone pP11/3, hybridizes to an mRNA approximately 1700 bases long ("VAC-alpha"), the cDNA of the clone pRH203 hybridizes to an mRNA approximately 2200 bases long ("VAC-beta").

Since, firstly, the quantity of radioactivity used and the amount of mRNA applied per trace were about the same and secondly the hybridization of a genome blot in the same solution yielded bands of the same intensity with both cDNAs (see below) it can be concluded that the shorter mRNA (VAC-alpha) is represented in larger quantities than the longer (VAC-beta) mRNA in placenta.

For sequence analysis of the VAC-alpha cDNA, the cDNA of clones pP6/5, pP6/6 and pP11/3, was totally sequenced and that of the clones lambda-VAC1 to 12 was partially sequenced. The results are shown in FIG. 4. In all, 1465 bases were sequenced. The cDNA shows a long open reading frame which can code for 320 amino acids. If the DNA sequence is translated into an amino acid sequence, all the sequenced peptides of the tryptic fragments can be accommodated in this sequence (FIG. 5). Therefore, this cDNA is the one whose corresponding mRNA codes for VAC protein. Since the sequences of the second isolated cDNA code for a similar protein but one which is different from VAC, the name VAC-alpha is introduced here.

The first ATG codon (bases 35–37) is preceded in the same reading frame by a stop codon. The bases 30 to 38 satisfy the Kozak rule fairly well (M. Kozak, Nature 308 (1984), pp. 241–246), which gives the consensus sequence near the translation start codon as CC(A/G)CCAUGG; the corresponding sequence here is TCGCTATGG. The 3' non-translated region is 471 bases long. 15 bases before the start of the poly-A section is the polyadenylation sequence AATAAA (N. J. Proudfoot et al., Nature 263 (1976), pp. 211–214). If the poly-A section of the mRNA is believed to have a chain length of 150 to 200 bases, the total length of the mRNA based on the cDNA sequence is 1600–1650 bases. Since a higher value was determined in the Northern blot experiment, the 5' non-translated region is not completely contained in any cDNA.

Unlike all other cDNA clones, the cDNA of clone pP6/5 has C instead of A at position 100. As a result, the triplet 98–100 (22nd codon) would change from GAA to GAC and would code for Asp instead of Glu. This deviation may have a number of causes: a) the reverse transcriptase has incorporated a wrong nucleotide, b) these are the transcripts of two allelic genes which differ at this point or c) there are two non-allelic genes which differ at this position.

The long open reading frame codes for a protein with 320 amino acids, from which the Met-1 is probably cleaved, and the following alanine is blocked at the amino group, possibly by acylation. The calculated molecular weight is 35,896 D and is higher than the value according to SDS-PAGE. Certainly, the proportion of charged amino acids (Asp, Glu, Lys, Arg, His) at 30.6% (98/320) is well above average compared with the average value of 25.1%. This would explain the different migration characteristics of the protein in the SDS-PAGE. Within the strongly charged amino acids, the acidic amino acids (Asp and Glu) are predominant, being 54 in number, compared with the basic amino acids (Lys and Arg), of which there are 41. This explains the acidic isoelectric point of the VAC-alpha protein (pI=4.4 to 4.8). VAC-alpha contains only one triplet coding for cysteine (amino acid position 316); there is no typical N-glycosylation site (Asn-XXX-Ser/Thr).

Structural analysis of the amino acid sequence (modified according to Pustell, J et al., Nucleic Acids Res. 10 (1982) pp 4765–4782) yields a four-fold repetition of a 67 amino acid long sequence (FIG. 6), hereinafter referred to as "repeats". Within this sequence, 7 amino acids (10.4%) are preserved in all four repeats, 15 amino acids (22.4%) occur in three of the four repeats, and at 28 positions (41.8%) two repeats each contain the same amino acid.

A comparison with published data (M. J. Geisow, FEBS Letters 203 (1986), pp. 99–103; M. J. Geisow et al., TIBS 11 (1986), pp. 420–423) surprisingly showed that VAC-alpha thus belongs to a fairly large group of Ca$^{++}$ dependent phospholipid binding proteins. A consensus sequence is described (Lys-Gly-fob-Gly-Thr-Asp-Glu-var-var-Leu-Ile-fil-Ile-Leu-Ala-fob-Arg; fob=hydrophobic, fil=hydrophilic, var=variable), which could be involved in the Ca$^{++}$ binding (M. J. Geisow et al., Nature 320 (1986), pp. 636–638). This 17 amino acid-long consensus sequence occurs in each of the four repeated 67 amino acid long subsequences of the proteins according to the invention (FIG. 6).

The 6 amino acid long section at the end of each repeat which consists almost exclusively of hydrophobic amino acids is also noticeable ("oooooo" in FIG. 6).

Sequence analysis of the clones Nr15, Nr19 and Nr22 showed 1940 bp for the VAC-beta cDNA, which merges into a poly-A section (FIG. 7). 16 bases before the poly-A section is the polyadenylation signal AATAAA. Certainly, this consensus sequence occurs at the nucleotide position 1704–1709. The reason why this sequence is not used as a polyadenylation signal is not known. The sequence additionally required at the 3' end of the AATAAA sequence, YGTGTTYY (Gill A. et al., Nature 312 (1984), pp. 473–474) does not occur until a relatively long way away (TGTGTTAT, positions 1735–1742); it is possible that this is the explanation for non-acceptance of this first polyadenylation sequence.

The cDNA contains a long open reading frame which extends from the beginning of the cDNA to position 1087. It would contain a coding potential for 362 amino acids. For reasons of analogy with VAC-alpha and owing to the fact that a 34,000 D protein also occurs during purification of VAC (see E.P.A. 181.465) the first methionine codon (ATG, position 107–109) was taken as the start of translation. The Kozak rule is not satisfied so well here as in VAC-alpha (AAGAGATGG at position 102–110). The resulting protein (VAC-beta) is 327 amino acids long. It has 4 cysteine groups (amino acid positions 161, 206, 250 and 293) and a potential N-glycosylation site (Asn-Lys-Ser, amino acid position 225–227). The calculated molecular weight is 36,837 (FIG. 9). In VAC-beta, as well, there are a larger than average number of charged groups: 97/327 (29.6%), while the acid amino acids (Asp+Glu: 49) predominate over the basic amino acids (Lys+Arg 42): an explanation for the lower molecular weight determined according to SDS-PAGE.

VAC-beta also shows an internal repetition of a 67 amino acid long sequence (FIG. 8). Within this sequence 7 amino acids (10.4%) are kept in all four repeats, 17 amino acids (25.4%) occur in three of the four repeats, and at 25 positions (37.7%) two repeats each contain the same amino acid. VAC-beta also shows a high similarity with the 17 amino acid long consensus sequence. The remarks made concerning VAC-alpha apply similarly to VAC-beta. By controlled mutations in this region attempts could be made to alter the biological activity of the proteins. Mutations according to the invention envisage, for example, total or partial replacement of the regions coding for the 17 amino acids of the conserved region.

When comparing the proteins it is found that the most noticeable difference between the proteins is at the N-terminal peptides. Modifications according to the invention therefore envisage exchanging these N-terminal peptides. These modified proteins can be prepared by producing the DNA molecules which code for N-terminal peptides, for example by oligonucleotide synthesis in a manner known per se, and ligating them with the "residual DNA" which codes for the remaining repeats and the linker sections. Expression vectors provided with this DNA can be expressed in a known manner in suitable host organisms; the expressed protein can be isolated and purified.

Figure 10:
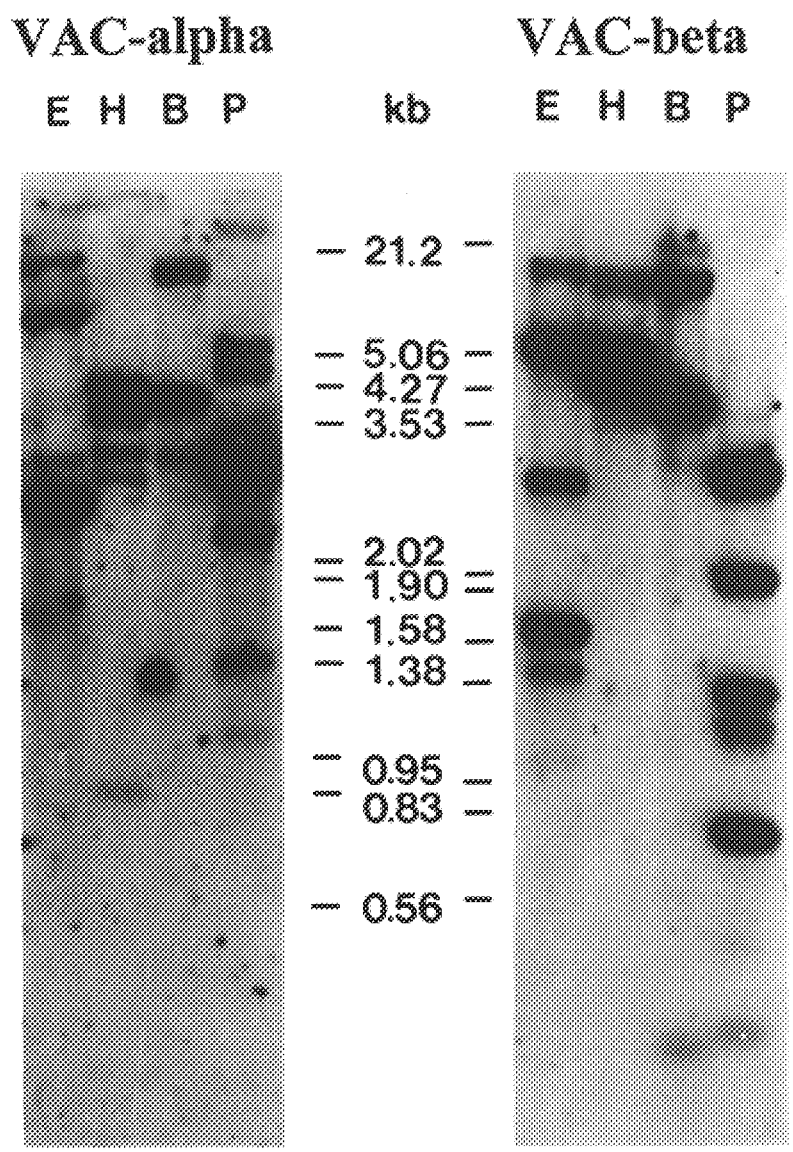

The analysis of chromosomal DNA from human placenta according to Southern shows a complex picture. The DNA was cut with EcoRI, HindIII, BamHI and PstI. The DNA transferred to nitrocellulose was hybridized both with a VAC-alpha DNA (pP11/3,) and also with a VAC-beta DNA (pRH203). Although the washing of the filters was carried out under stringent conditions, a relatively large number of bands were obtained on each digestion (FIG. 10). Comparison of the two blots shows that the cross reaction of VAC-alpha and VAC-beta DNA under these conditions can be more than likely ruled out. The multiplicity of the bands can be explained either by the existence of similar genes to the VAC-alpha or VAC-beta gene or else it is a gene which is interrupted by many and/or long introns.

FIG. 11 shows a comparison of the amino acid sequences of VAC-alpha with VAC-beta. The repeated structures can be arranged identically in both proteins. The connecting peptides are also of the same length, with the exception of those between the second and third repeats. A gap has to be inserted in this connecting peptide in VAC-alpha in order to permit optimum matching of the two sequences. The N-terminal peptide of the two proteins is of different lengths, 19 amino acids in the case of VAC-alpha and 25 amino acids in VAC-beta. This peptide also has the lowest homology. The two proteins are identical at 176 of 320 amino acid positions, corresponding to a level of homology of 55.0%.

At this point a comparison of the nucleotide sequences of VAC-alpha and VAC-beta cDNAs will be included. If two genes and their products are compared with each other, the DNA (=RNA) plane shows a greater homology than the amino acid plane, which is explained by the fact that in the nucleic acid a change in a base triplet is sufficient to code a new amino acid.

FIG. 12 shows a comparison of the coding regions of VAC-alpha and VAC-beta cDNA. Surprisingly, the DNAs show a degree of homology of only 54.2%, i.e. somewhat less than the two proteins.

FIG. 13 shows the hydrophilicity profiles of the two proteins. The algorithm of Hopp and Wood was used (T. P. Hopp et al., Proc. Natl. Acad. Sci. 78 (1981) pp. 3824–3823). The four repeat areas are indicated by the bars and the connecting peptides are framed in the sequence shown below. Surprisingly, the connecting peptide between the second and third repeats is particularly hydrophilic. This peptide contains, both in VAC-alpha and in VAC-beta, an arginine at identical positions. It would therefore be possible for this arginine to be a preferred point of attack for a protease with trypsin-like specificity. The molecule would then have to break into two halves of approximately equal size. It would be conceivable for a "half molecule" of this kind to develop a biological activity, for example an anticoagulant activity. Apart from the controlled digestion of the protein, for example with a protease of trypsin-like specificity, these half molecules or half molecules with slight modifications may be prepared by numerous methods. Thus, it is possible to insert the DNA molecules coding for these half molecules, which can be prepared by methods known in the art, in suitable expression vectors in such a way that this DNA is regulated by the expression control sequences and, by cultivating a host organism transformed with these vectors, to express, isolate and purify the half molecules.

Half molecules with slight modifications may be obtained, for example, by inserting cleavage sites which impart to the protein as a whole the specificity required for certain proteases. Thus, for example, a protein with a cleavage site with factor Xa-like specificity can be produced by inserting an oligonucleotide which codes for the recognition tetrapeptide of the factor Xa protease in the section which codes for the linker sequence between the second and third repeat structures. In this way, a complete protein is initially obtained which possibly has modified properties, for example altered stability against proteolytic attack, but on the other hand contains a highly specific cleavage site for the factor Xa protease, as a result of which two half molecules can be deliberately prepared and used for therapeutic purposes.

By controlled mutation of the DNA coding for proteins with VAC activity, it is also possible to prepare proteins which have greater resistance to proteolytic attack. Thus, replacement of the arginine common to VAC-alpha and VAC-beta between the second and third repeat structures by histidine, for example, results in improved stability of the proteins. The controlled replacement of the other arginines and lysines by histidine, possibly by replacement of the corresponding codons, also leads to proteins which are difficult for trypsin to hydrolyze. These controlled mutations leave the biological, for example anticoagulant properties of the proteins/polypeptides essentially unchanged, but do result in changes, for example improvements in the stability of the proteins, i.e. they change the half-life of the proteins.

In many cases, for example for the expression of proteins, it is advantageous to precede the mature, desired protein/polypeptide by a signal sequence or by a protein sequence native to the host organism, so that a fusion protein is produced as an expression product. The signal sequence coding for a signal peptide may be of microbial origin or may come from mammalian cells; preferably, the signal peptide is homologous to the host organism. In order to be able to convert these products into the desired mature protein, a specific cleavage site is required between the signal/fusion part and the mature protein. For this purpose, an oligonucleotide which codes for the recognition tetrapeptide of the factor Xa protease, for example, may be inserted at this site as described above. As a result, the expressed fusion protein can be cleaved in controlled manner with the factor Xa protease. The mature protein is obtained.

If the codons responsible for methionine, apart from the one at amino acid position 1, are deliberately replaced by codons which code for leucine, isoleucine or valine, any immature or fusion protein which may be obtained can be converted into the mature protein by BrCN cleavage. If it should prove that proteins modified in this way have the same or possibly better biological properties, this would be a possible way of increasing the yield and possibly a method of preparing proteins with better properties than the natural VAC proteins.

Another deliberate mutation is the controlled replacement of one, possibly more cysteines by serine or valine, by exchanging the corresponding codons. If this exchange does not have a harmful effect on the biological activity, this method could bring about an improvement in the isolation and/or yield of the proteins. An improvement in the properties of the proteins cannot be ruled out either. A further mutation is the combination of different complete or partial sequences of the DNAs coding for the proteins according to the invention, thereby obtaining hybrid proteins with vascular anticoagulant properties. All the proteins which can be obtained by these or similar mutations, the DNAs coding for them, the preparation and use thereof are also objects of the present invention.

FIG. 13 also clearly shows that neither VAC-alpha nor VAC-beta has a long hydrophobic area which would permit either secretion through or depositing of proteins in a membrane. It can therefore be assumed that VAC-alpha and VAC-beta are intracellular proteins.

Wallner et al. (Nature 320 (1986), pp. 77–81) report the structure of human lipocortin I, Saris et al. (Cell 46 (1986), pp. 201–212) and Huang et al. (Cell 46 (1986), pp. 191–199) report the structure of murine or human calpactin I, which is also known as lipocortin II. These proteins also belong to the class of $Ca^{++}$ dependent phospholipid binding proteins. Their structure can be written analogously to VAC-alpha and beta (FIG. 14). However, the homologies between VAC-alpha and VAC-beta are more marked than those between VAC and lipocortin:

VAC-alpha—VAC beta: 55.0%
VAC-alpha—lipocortin I: 41.9%
VAC-alpha—lipocortin II: 43.8%
VAC-beta—lipocortin I: 41.7%
VAC-beta—lipocortin II: 44.6%

It must therefore be assumed that the lipocortins also have an anticoagulant activity owing to their analogous structure and consequently can be used as anticoagulants and furthermore that this is a general property of this class of $Ca^{++}$ dependent phospholipid binding proteins. Furthermore, on the basis of the analogous structures, it may be assumed that the proteins according to the invention have, in addition to their anticoagulant activity, the properties of the class of $Ca^{++}$ dependent phospholipid binding proteins already known.* For example, the anti-inflammatory properties of lipocortins may be mentioned here. The present invention therefore also relates to the use of the proteins according to the invention as anti-inflammatory agents and the use of the proteins according to the invention in the treatment of all indications which apply to the lipocortins, such as rheumatic complaints. For this purpose, the products according to the invention corresponding to the natural proteins can be modified in the manner described above and their properties improved if necessary.

* An assumption which could be proofed by the phospholipase inhibitory activities of VAC (see below).

A comparison of the proteins VAC-alpha, VAC-beta, lipocortin I and lipocortin II shows that the most striking difference between the proteins is in the N-terminal peptides, particularly between the VAC proteins on the one hand and the lipocortins on the other hand. A modification according to the invention therefore envisages the exchanging of these N-terminal peptides. These modified proteins can be prepared by producing the DNA molecules coding for these N-terminal peptides, for example by oligonucleotide synthesis in a manner known per se, and ligating them with the "residual DNA" which codes for the remaining repeats and the linker sections. Expression vectors provided with this DNA can be expressed in suitable host organisms in known manner; the expressed protein is isolated and purified.

Many members of the $Ca^{++}$ dependent phospholipid binding proteins bind to purified secretory vesicles or other constituents of the cytoskeleton (see R. H. Kretsinger et al., Nature 320 (1986), p 573 for a summary). During secretion, the vessels detach themselves from the Golgi apparatus of the cells, migrate to the cell membrane and fuse with it. The contents of the vesicles are thus freed from the cell. Analogously with the coupling of excitation with muscle contraction, it has been proposed (W. W. Douglas, Br.J.Pharmac. 34 (1968), 451) that the stimulus and secretion are coupled via $Ca^{++}$. The $Ca^{++}$ dependent phospholipid binding proteins could play an important part. In the conserved, 17 amino acid long region of each repeat, VAC-alpha has 5 to 6 amino acids which contain hydroxyl groups (Asp, Glu, Thr, Ser), three of them in identical positions. In VAC-beta, four of these amino acids occur in each repeat. Although none of the proteins has the EF-Hand structure observed in calmodulin, troponin C, S-100 and parvalbumin (R. H. Kretsinger et al., CRC Crit. Rev.Biochem. 8 (1980), p119) which is responsible for the $Ca^{++}$ binding in these molecules, the conserving of this subsection in each repeat leads one to conclude that this region is responsible for the $Ca^{++}$ binding.

By controlled mutations in this area, attempts can be made to vary the biological activity of the proteins. Mutations according to the invention envisage, for example, complete or partial replacement of the regions coding for the 17 amino acids of the conserved region:

a) from the VAC proteins by areas which encode the corresponding amino acids of the lipocortins,
b) from VAC-alpha by areas which code the corresponding amino acids of VAC-beta and vice versa, c) from lipocortin I by areas which code the corresponding amino acids of lipocortin II and vice versa, d) from lipocortins by areas which code the corresponding amino acid of the VAC proteins or e) in the other polypeptides/proteins by areas which code the corresponding amino acids of the other polypeptides/proteins in each case, by substituting the corresponding areas coding for these amino acids.

The above-mentioned analogous structure also leads one to expect that proteins which show this analogy will have both anti-inflammatory and anticoagulant properties and can therefore be used accordingly therapeutically and/or prophylactically.

The present invention therefore relates in particular to the use of the polypeptides as anti-inflammatory agents, as anti-rheumatic agents, in the indications which apply to lipocortins, the use of the polypeptides/proteins which have repeat areas as blood coagulation-inhibiting agents, as thrombin-inhibiting agents, as anti-inflammatory agents, as anti-rheumatic agents, use of the lipocortins as coagulation-inhibiting agents, as thrombin inhibiting agents and in the indications which apply to the VAC proteins, while specifically excluding the known uses of the proteins with repeat areas of this kind, some of which are described in this application.

The invention further relates to agents for therapeutic treatment which contain, in addition to pharmaceutically inert carriers, an effective amount of one of these polypeptides.

The present invention also relates to DNA molecules which code for a polypeptide/protein with repeat areas, DNA molecules which code for one of the repeat areas, DNA molecules which are characterized in that the areas coding for the full repeats are rearranged, the proteins coded thereby, the preparation and use thereof.

The invention also includes all proteins which can be obtained by these or similar mutations, the DNAs coding for them, their preparation and use, whilst the known proteins, some of which are described in the present application, the DNAs coding for them, their known preparation and use are specifically excluded.

The present invention also relates to DNA molecules of non-human origin, the proteins coded thereby, the preparation and use thereof, which can be prepared by a method analogous to the present invention.

The invention relates not only to genetic sequences which code specifically for the proteins according to the invention but also to modifications which can easily and routinely be obtained by mutation, degradation, transposition or addition. Any sequence which codes for the proteins according to the invention (i.e. which has the biological spectrum of activity described herein) and is degenerate compared with those shown, is also included; anyone skilled in the art is capable of degenerating DNA sequences of the coding regions. Similarly, any sequence which codes for a polypeptide with the spectrum of activity of the proteins according to the invention and which hybridizes with the sequences shown (or parts thereof) under stringent conditions (e.g. conditions which select for more than 85%, preferably more than 90% homology) is also included.

The hybridizations are carried out in 6×SSC/5× Denhardt's solution/0.1% SDS at 65° C. The degree of stringency is determined in the washing step. Thus, for selection of DNA sequences with approximately 85% or more homology, suitable conditions are 0.2×SSC/0.01% SDS/65° C. and for selection of DNA sequences with approximately 90% homology or more, the suitable conditions are 0.1×SSC/0.01% SDS/65° C.

The invention further relates to expression vectors which contain a DNA sequence coding for VAC, which is regulated by an expression control sequence in such a way that polypeptides with VAC activity are expressed in a host cell transformed with this expression vector.

The expression vectors of the present invention may be prepared, for example, by introducing a VAC coding DNA sequence into a vector DNA which contains an expression control sequence in such a way that the expression control sequence regulates the said DNA sequence.

The choice of a suitable vector results from the particular host cell used for the transformation. Suitable hosts include, for example, microorganisms such as yeasts, e.g. *Saccharomyces cerevisiae*, and particularly bacterial strains which have no restriction or modification enzyme, especially strains of *Escherichia coli*, e.g. *E. coli* X1776, *E. coli* HB101, *E. coli* W3110, *E. coli* HB101/LM1035, *E. coli* JA221 (30) or *E. coli* K12 strain 294, *Bacillus subtilis*, *Bacillus stearothermophilus*, Pseudomonas, Haemophilus, Streptococcus and others, also cells of higher organisms, particularly established human or animal cell lines. The preferred host cells are all the strains of *E. coli* particularly *E. coli* HB101, *E. coli* JM101 and *E. coli* W3110.

Theoretically, all vectors which replicate and express the heterologous DNA sequences coding for VAC in the host selected are suitable.

Examples of vectors which are suitable for the expression of the VAC gene in an *E. coli* strain are bacteriophages e.g. derivatives of the bacteriophage λ, or plasmids, particularly the plasmid colE1 and the derivatives thereof, e.g. pMB9, pSF2124, pBR317 or pBR322. The preferred vectors of the present invention are derived from plasmid pBR322. Suitable vectors contain a complete replicon and a labelling gene which makes it possible to select and identify the microorganisms transformed with the expression plasmids on the basis of a phenotypical feature. Suitable markings may give the microorganism resistance to heavy metals, antibiotics and the like, for example. Moreover, preferred vectors according to this invention contain, in addition to the replicon and labelling gene regions, recognition sequences for restriction endonucleases, so that at these points the DNA sequence coding for the amino acid sequence of VAC and optionally the expression control sequence can be inserted.

A preferred vector, the plasmid pBR322, contains an intact replicon, labelling genes ($tet^R$ and $amp^R$) which give resistance to tetracycline and ampicillin and a number of unique recognition sequences for restriction endonucleases, e.g. PstI (cuts in the $amp^R$ gene, the $tet^R$ gene remains intact), BamHI, HindIII, SalI (all cut in the $tet^R$ gene whilst the $amp^R$ gene remains intact), NruI and EcoRI.

A number of expression control sequences may be used to regulate the VAC expression. In particular, expression control sequences of strongly expressed genes of the host cell which is to be transformed are used. In the case of pBR322 as the hybrid vector and *E. coli* as the host organism, for example, the expression control sequences (which contain inter alia the promoter and the ribosomal binding site) of the lactose operon, tryptophan operon, arabinose operon and the like, the β-lactamase gene, the corresponding sequence of the phage λN gene or the phage fd-layer protein gene and others are suitable. While the promoter of the β-lactamase gene (β-lac gene) is already contained in the plasmid pBR322, the other expression control sequences must be introduced in the plasmid. The preferred expression control sequence in the present invention is that of the tryptophan operon (trp po) and that of *Serratia marcescens* and also of *E. coli* and the alkaline phosphatase promoter or the hybrid thereof.

In addition to these particularly common promoters, other microbial promoters have also been developed and used. The genetic sequence for the proteins according to the invention may, for example, be used under the control of the leftward promoter of the bacteriophage lambda ($P_L$). This promoter is a particularly effective controllable promoter. Control is made possible by the lambda repressor of which adjacent restriction cutting sites are known. A temperature-sensitive allele of this repressor gene may be inserted into a vector which contains a protein gene sequence. If the temperature is increased to 42° C., the repressor is inactivated and the promoter is activated. By using this system, it is possible to establish a clone bank in which a functional protein gene sequence is placed close to a ribosome binding site at varying distances from the lambda $P_L$ promoter. These clones can then be checked and those with the highest yield selected.

The expression and translation of a sequence coding for the proteins according to the invention may also be effected under the control of other regulating systems which may be regarded as "homologous" to the organism in its untransformed form. Thus, for example, chromosomal DNA from a lactose-dependent *E. coli* contains a lactose or lac-operon which allows the degradation of lactose by secreting the enzyme beta-galactosidase.

The lac-control elements may be obtained from the bacteriophage lambda-plac5, which is infectious for *E. coli*. The lac-operon of the phage may be obtained from the same bacterial species by transduction. Regulating systems which may be used in the process according to the invention may originate from plasmid DNA which is native to the organism. The lac-promoter-operator system may be induced by IPTG.

Other promoter-operator systems or parts thereof may be used with equally good effect: for example, colicin $E_1$-operator, galactose operator, xylose-A operator, tac-promoter, etc.

In addition to prokaryotes, eukaryotic microorganisms such as yeast cultures may also be used. *Saccharomyces cerevisiae* is the most commonly used of the eukaryotic microorganisms, although a number of other species are generally obtainable.

Vectors suitable for replication and expression in yeast contain a yeast replication start and a selective genetic marker for yeast. Hybrid vectors which contain a yeast replication start, e.g. the chromosomal autonomically replicating segment (ars), are retained extra-chromosomally after transformation within the yeast cell and are replicated autonomously during mitosis. For expression in Saccharomyces, for example the plasmid YRp7 (Stinchcomb et al., Nature 282, 39 (1979); Kingsman et al., Gene 7, 141 (1979); Tschumper et al., Gene 10, 157 (1980)) and the plasmid YEp13 (Bwach et al., Gene 8, 121–133 (1979)) are conventionally used. The plasmid YRp7 contains the TRP1 gene which is a selectable marker for a yeast mutant which is incapable of growing in tryptophan-free medium; for example ATCC No. 44076.

The presence of the TRP1 defect as a characteristic of the yeast host genome constitutes an effective aid to detecting transformation, when cultivation is carried out without tryptophan. The situation is very similar with the plasmid YEp13, which contains the yeast gene LEU 2, which can be used to complement a LEU 2-minus mutant.

Other suitable marking genes for yeast are, in general, in the case of auxotrophic yeast mutants, genes which complement the host defects. Corresponding genes ensure prototrophy in an auxotrophic yeast mutant, e.g. the URA3 and HIS3 gene. Preferably, yeast hybrid vectors also contain a replication start and a marker gene for a bacterial host, particularly E. coli, so that the construction and cloning of the hybrid vectors and their precursors can take place in a bacterial host. Other expression control sequences which are suitable for expression in yeast include, for example, those of the PHO3 or PHO5 gene, and also promoters involved in glycolytic degradation, e.g. the PGK and GAPDH promoter.

Other suitable promoter sequences for yeast vectors contain the 5'-flanking region of ADH I (Ammerer G., Methods of Enzymology 101, 192–201 (1983)), 3-phosphoglycerate kinase (Hitzeman et al., J. Biol. Chem. 255, 2073 (1980)), or other glycolytic enzymes (Kawasaki and Fraenkel, BBRC 108, 1107–1112 (1982)) such as enolase, glyceraldehyde-3-phosphate dehydrogenase, hexokinase, pyruvate decarboxylase, phosphofructokinase, glucose-6-phosphate isomerase, phosphoglucose isomerase and glucokinase. By constructing suitable expression plasmids the termination sequences associated with these genes may also be inserted into the expression vector at the 3'-end of the sequence which is to be expressed, in order to ensure polyadenylation and termination of the mRNA.

Other promoters which also have the advantage of transcription controlled by growth conditions are the promoter regions of the genes for alcohol dehydrogenase-2, isocytochrome C, acid phosphatase, degradation enzymes which are coupled to nitrogen metabolism, the above-mentioned glyceraldehyde-3-phosphate dehydrogenase and enzymes which are responsible for the processing of maltose and galactose. Promoters which are regulated by the yeast mating type locus, for example promoters of the genes BAR1, MFα1, STE2, STE3 and STE5, may be used in temperature-regulated systems by the use of temperature-dependent sir mutations (Rhine, Ph.D. Thesis, University of Oregon, Eugene, Oreg. (1979), Herskowitz and Oshima, The Molecular Biology of the Yeast Saccharomyces, Part I, 181–209 (1981), Cold Spring Harbour Laboratory)). These mutations affect the expression of the resting mating type cassettes of yeasts and thus indirectly the mating type dependent promoters. Generally, however, any plasmid vector which contains a yeast-compatible promoter, original replication and termination sequences, is suitable.

Thus, it is also possible to use hybrid vectors which contain sequences homologous to the yeast-$2\mu$ plasmid DNA. Hybrid vectors of this kind are incorporated within the cell by recombination with existing $2\mu$ plasmids or replicate autonomously. $2\mu$ sequences are particularly suitable for plasmids with a high transformation frequency and permit a high copy number.

In addition to microorganisms, cell cultures of multicellular organisms are also suitable host organisms. In theory, any of these cultures may be used, whether obtained from vertebrate or invertebrate animal cultures. However, the greatest interest has been in vertebrate cells, with the result that the multiplication of vertebrate cells in culture (tissue culture) has become a routine method in recent years (Tissue Culture, Academic Press, Editors Kruse and Patterson, (1973)). Examples of useful host cell lines of this kind include VERO and HeLa cells, CHO cells and WI38, BHK, COS-7 and MDCK cell lines. Expression vectors for these cells generally contain (when necessary) a replication starting point, a promoter which is located in front of the gene to be expressed, together with any necessary ribosome binding site, RNA splicing site, polyadenylation site and transcriptional termination sequences.

When used in mammalian cells, the control functions in the expression vector are often obtained from viral material. For example, the promoters normally used originate from polyoma, adenovirus 2 and particularly frequently from Simian virus 40 (SV 40). The early and late promoters of SV 40 are particularly useful since both can be easily obtained from the virus as a fragment which also contains the viral replication site of the SV 40 (Fiers et al., Nature 273, 113 (1978)). It is also possible to use smaller or larger fragments of SV 40, provided that they contain the sequence, approximately 250 bp long, which extends from the HindIII cutting site to the BglI cutting site in the viral replication site. Furthermore it is also possible and often desirable to use promoter or control sequences which are normally linked to the desired genetic sequences, provided that these control sequences are compatible with the host cell systems.

A replication starting point may either be provided by corresponding vector construction in order to incorporate an exogenic site, for example from SV 40 or other viral sources (e.g. polyoma, adeno, VSV, PBV, etc.) or it may be provided by the chromosomal replication mechanisms of the host cell. If the vector is integrated into the host cell chromosome, the latter measure is usually sufficient.

The invention relates in particular to expression vectors capable of replication and phenotypical selection which contain an expression control sequence and a DNA sequence coding for the amino acid sequence of VAC, said DNA sequence together with the transcription start signal and termination signal and the translation start signal and stop signal in said expression plasmid being arranged, with regulation of said expression control sequence, in such a way that VAC is expressed in a host cell transformed with said expression plasmid.

To achieve effective expression, the VAC gene must be arranged correctly ("in phase") with the expression control sequence. It is advantageous to link the expression control sequence in the region between the main mRNA start and the ATG of the gene coding sequence, which is naturally linked to the expression control sequence (e.g. the β-lac coding sequence if the β-lac promoter is used), to the VAC gene which preferably brings with it its own translation start signal (ATG) and translation stop signal (for example TAG). This ensures effective transcription and translation.

For example, a vector, particularly pBR322, is cut with a restriction endonuclease and, optionally after modification of the linearized vector thus formed, an expression control sequence provided with corresponding restriction ends is introduced. The expression control sequence contains at the 3' end (in the direction of translation) the recognition sequence of a restriction endonuclease, so that the vector which already contains the expression control sequence is digested with said restriction enzyme and the VAC gene provided with the corresponding ends can be used. A mixture of two hybrid plasmids is thus formed containing the gene in the right or wrong orientation. It is advantageous to cleave the vector which already contains the expression control sequence with a second restriction endonuclease within the vector DNA and to use the VAC gene provided with the right ends in the resulting vector fragment. All operations on the vector are preferably carried out so that the function of the replicon and of at least one marking gene are not affected.

In a preferred embodiment of the present invention, a vector derived from pBR322, which contains an expression control sequence, particularly that of the tryptophan operon (trp po) and which carries at its 3' end (between the main mRNA start and the first ATG) the recognition sequence for a restriction endonuclease, e.g. EcoRI, which preferably forms cohesive ends, is digested with the above-mentioned restriction endonuclease and in the vector-DNA part with a second restriction endonuclease which forms flat or preferably cohesive ends, e.g. BamHI, after which the vector thus linearized is linked with the VAC-DNA having corresponding ends (e.g. with an EcoRI end before the ATG start and a BamHI end after the translation stop codon). Linking is effected in known manner by pairing the complementary (cohesive) ends and ligation, e.g. with $T_4$-DNA ligase.

Preferably, the DNA sequences according to the invention may also be expressed in the expression plasmid pER103 (E. Rastl-Dworkin et al., Gene 21, 237–248 (1983) and EP-A-0115613—deposited at the DSM under No. DSM 2773 on 20th Dec. 1983), in the plasmid parpER33 (EP-A-0115613) or the plasmid pRH100, since these vectors all contain regulatory elements which lead to a high expression rate for the cloned genes. According to the invention, the plasmid pRH100 which contains the regulatable tryptophan promoter from *Serratia marcescens* and an artificial ribosome binding site, is used as the expression vector for the synthetic protein gene. In order to prepare the expression plasmid pRH100, the plasmid pER103 (Eva Dworkin-Rastl et al., Gene 21 (1983) 237–248, EP-A-0115613) was linearized with the restriction endonuclease HindIII and the oligonucleotide sequence

5' AGCTTAAAGATGAGCTCATCTTTA 3'

3' ATTTCTACTCGAGTAGAAATTCGA 5' was inserted.

The VAC-DNA provided with corresponding (in particular EcoRI and BamHI) ends, obtained by the mRNA method, from genomic DNA or synthetically, can be cloned into a vector, e.g. pBR322, before being introduced into an expression plasmid, in order to obtain larger quantities of VAC-DNA, for example for sequence analysis. Isolation of the clones which contain the hybrid plasmid is carried out, for example, with a VAC-DNA specific, radioactively labelled oligonucleotide probe (see above). The VAC-DNA is characterized, for example, using the method of Maxam and Gilbert (11).

In another embodiment of the invention, fragments of the VAC-DNA are synthesised. The invention also relates to a process for preparing transformed host cells, characterized in that a host cell is transformed with an expression vector which contains a DNA sequence regulated by an expression control sequence and coding for the amino acid sequence of VAC.

Suitable host cells are for example the above-mentioned microorganisms, such as strains of *Saccharomyces cerevisiae, Bacillus subtilis* and, in particular, *Escherichia coli*. Transformation with the expression plasmids according to the invention is effected, for example, as described in the literature, for *S. cerevisiae* (12), *B. subtilis* (13) and *E. coli* (14). The transformed host cells are advantageously isolated from a selective nutrient medium to which is added the biocide against which the marker gene contained in the expression plasmid gives resistance. If, as is preferred, the expression plasmids contain the $amp^R$ gene, ampicillin is added to the nutrient medium accordingly. Cells which do not contain the expression plasmid are killed off in such a medium.

The invention also relates to the transformed host cells which can be obtained by the method described.

The transformed host cells can be used to prepare compounds with VAC activity. The process for preparing this compound is characterized in that the transformed host cells are cultivated and the product is released from the host cells and isolated.

The invention therefore relates in particular to a process for preparing compounds with VAC activity and salts of such compounds, characterized in that host cells transformed with an expression plasmid which contains a DNA sequence coding for the amino acid sequence of VAC and regulated by an expression control sequence are cultivated in a liquid nutrient medium which contains assimilable carbon and nitrogen sources and the product is freed from the host cells and isolated and, if necessary, a product obtainable according to this process is mixed with a reducing agent suitable for breaking the disulphide bonds and the reduced polypeptide obtained is, if desired, treated with an oxidizing agent suitable for the fresh formation of disulphide bonds and, if desired, a VAC compound obtained is converted into another VAC compound, a mixture of compounds with VAC activity obtained by the process is separated into the individual components and/or, if desired, a salt obtained is converted into the polypeptide and a polypeptide obtained is converted into the corresponding salt thereof.

The present invention relates particularly to a process for preparing VAC compounds.

The transformed host cells according to the invention are cultivated in a manner known in the art. Thus, various carbon sources may be used to cultivate the transformed host microorganisms according to the invention. Examples of preferred carbon sources include assimilable carbohydrates, such as glucose, maltose, mannitol or lactose, or an acetate which may be used either on its own or in suitable mixtures. Suitable nitrogen sources include, for example, amino acids such as casamino acids, peptides and proteins and the breakdown products thereof such as tryptone, peptone or meat extracts; also yeast extracts, malt extract, and also ammonium salts, e.g. ammonium chloride, sulphate or nitrate, which may be used either on their own or in suitable mixtures. Inorganic salts which may also be used, include for example sulphates, chlorides, phosphates and carbonates of sodium, potassium, magnesium and calcium.

The medium also contains, for example, growth promoting substances such as trace elements, e.g. iron, zinc, manganese and the like and preferably substances which exert a selection pressure and prevent the growth of cells which have lost the expression plasmid. Thus, for example, ampicillin is added to the medium if the expression plasmid contains an $amp^R$ gene. The addition of antibiotically active substances in this way also ensures that any contaminating, antibiotic-sensitive microorganisms are killed off.

The conditions of cultivation, such as temperature, pH of the medium and fermentation time, are selected so as to obtain the maximum VAC titre. Thus, an *E. coli* or yeast strain is preferably cultivated under aerobic conditions in a submerged culture with shaking or stirring at a temperature of about 20° to 40° C., preferably about 30° C., and at a pH of from 4 to 9, preferably at pH 7, for about 4 to 20 hours, preferably 8 to 12 hours. The expression product accumulates within the cells.

When the cell density has reached a sufficient level, the cultivation is stopped and if necessary the product is freed from the cells of the microorganism. For this purpose, the cells are destroyed, e.g. by treating with a detergent such as SDS or triton or lysed with lysozyme or an enzyme with a similar activity. Alternatively or additionally, mechanical forces such as shear forces (e.g. an X press, French press or Dyno-Mill) may be used or the cells may be broken up by shaking with glass beads or aluminium oxide or by alternately freezing, e.g. in liquid nitrogen, and thawing, e.g. to 30° to 40° C., or by ultrasound. The resulting mixture which contains proteins, nucleic acids and other cell constituents is concentrated with proteins in known manner after being centrifuged. Thus, for example, the majority of the non-protein constituents are separated off by polyethyleneimine treatment and the proteins including the VAC compounds are precipitated, for example, by saturation of the solution with ammonium sulphate or other salts. Other purification steps include, for example, chromatographic methods such as ion exchange chromatography, HPLC, reverse phase HPLC and the like. Thus, the components of the mixture are separated by dialysis, after charging using gel electrophoresis or carrier-free electrophoresis, in accordance with molecular size using a suitable Sephadex column, by affinity chromatography, e.g. with antibodies, particularly monoclonal antibodies, or with thrombin coupled to a suitable carrier for affinity chromatography, or by other methods, particularly those known from the literature.

For example, isolation of the expressed VAC compounds comprises the following steps. Separation of the cells from the culture solution by centrifuging; preparation of a crude extract by destruction of the cells, e.g. by treating with a lysing enzyme and/or alternate freezing and re-thawing; removing the insoluble matter by centrifuging; precipitating the DNA by the addition of polyethyleneimine; precipitating the proteins by means of ammonium sulphate; affinity chromatography of the dissolved precipitate on a monoclonal anti-VAC antibody column; removal of salts from the solution thus obtained by dialysis or chromatography on Sephadex G25 or Sephadex G10.

Other purification steps include gel filtration on Sephadex G50 (or G75) and reverse phase HPLC. Salts may be removed on Sephadex G25.

The VAC activity can be detected using the test with anti-VAC antibodies (e.g. monoclonal antibodies obtainable from rabbits/mice or from hybridoma cells) or the tests described in EPA 0181465 may be used.

As already mentioned, the alkaline phosphatase promoter is particularly suitable for expression of the proteins according to the invention.

The gene for alkaline phosphatase (phoA) from *E. coli* is subject to strict regulation. In the presence of phosphate the gene is switched off completely and in the absence of phosphate in the medium gene expression takes place. H. Shuttleworth et al., Nucleic Acids Res. 14 (1986) page 8689 and C. N. Chang et al., Gene 44 (1986), pages 121–125 describe the nucleotide sequence of this gene. In order to construct a suitable expression vector, the promoter region of the phoA gene was assembled from several oligonucleotides and inserted into EcoRI-ClaI cut pAT153 (Amersham). In front of the ribosomal binding site, an XhoI site was introduced.

The original EcoRI site is destroyed when the synthetic DNA fragment is ligated in. A translation start ATG was provided after the ribosomal binding site the G of which is the first nucleotide of a SacI (=SstI) site. The expression vector can be linearized by cutting with SacI at this site and the 3' overhang can be converted into a straight end by treating with DNA polymerase I—Klenow fragment in the presence of dGTP. In this way, any desired gene can be inserted at this point; for correct expression it must begin with the first base of the coding region.

The HindIII-SalI fragment of the pAT section was removed and replaced by the alkaline phosphatase transcription terminator. The original SalI site was destroyed. To do this, it was reintroduced in front of the terminator together with the BamHI site which was also deleted from pAT153. The sequence of the synthetically produced DNA is shown in FIG. 15. The resulting vector is referred to as pRH284T.

In order to prepare a vector which is suitable for expressing VAC-alpha, a DNA molecule coding for VAC-alpha was introduced into the pRH284T. For this purpose, the cDNA clone pP6/5 was cut with BglII and PstI and the 980 bp long fragment which contains the majority of the coding region and about 200 bp of 3' non-translated region was isolated. The missing 5' end of the coding region was replaced using oligonucleotides. A KpnI cutting site was simultaneously introduced into the VAC-cDNA by two mutations (GGC→GGT, Gly-7 and ACT→ACC, Thr-8).

The oligonucleotides had the following appearance:

```
             |EBI-678
                                                                     ||EBI-677
       5'  GCACAGGTTCTCAGAGGTACCGTGACTGACTTCCCTGGATTTGATGAGCGGGCT
           CGTGTCCAAGAGTCTCCATGGCACTGACTGAAGGGACCTAAACTACTCGCCCGA
           |                                         EBI-680||
           GATGCAGAAACTCTTCGGAAGGCTATAAAGGCTTGGGCACAGATGAGGAGAGC
           CACGTCTTTGAGAAGCCTTCCGATACTTTCGAACCCGTGTCTACTCCTCTCG
                                                                              EBI-
                   ||EBI-682                                                      |
           ATCCTGACTCGTTGACATCCGAAGTAATGCTCAGCGCCAGGAAATCTCTGCA    3'
           AGGACTGAGACAACTGTAGGGCTTCATTACGAGTCGCGGTCCTTTAGAG       5'
           679||                                            EBI-681|
```

Figure 16:
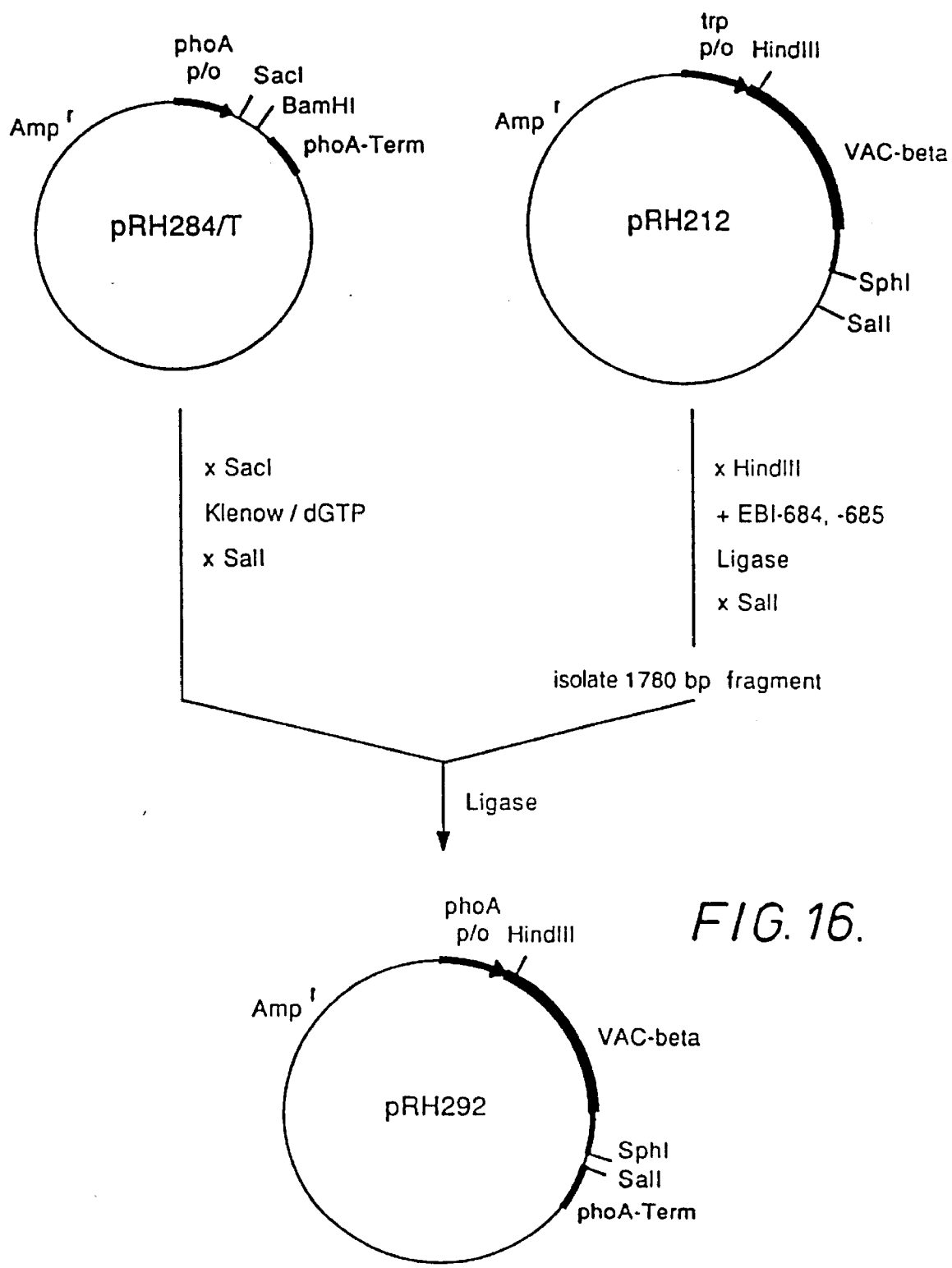

The vector thus produced was designated pRH291 (FIG. 16).

Figure 17:
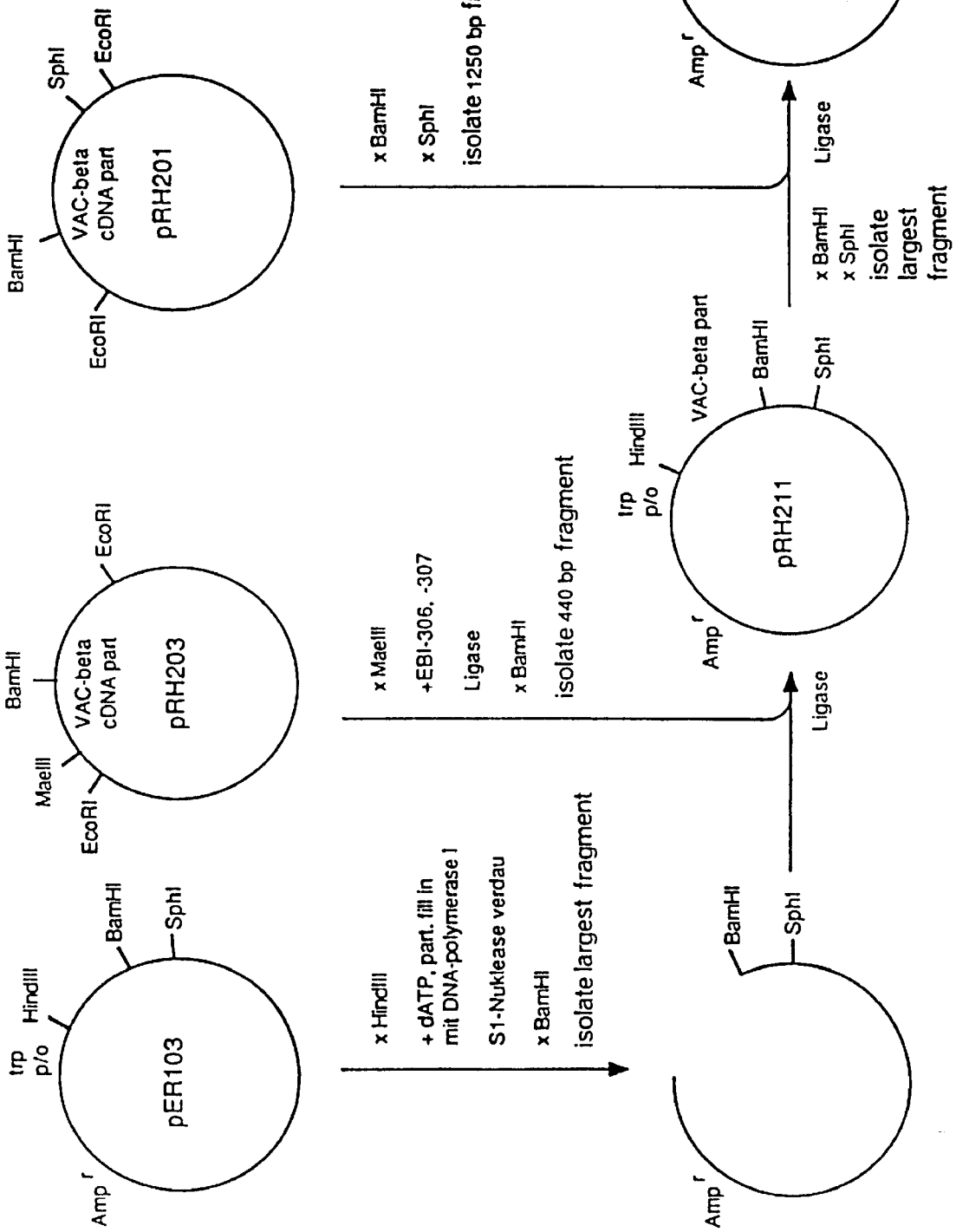

In order to express VAC-beta, the plasmid PER103 was preferably used as expression vector (E. Rastl-Dworkin et al., Gene 21 (1983), 237–248). The vector was linearized with HindIII. The 5' overhanging end was partially filled in with dATP and DNA polymerase I/Klenow fragment and the remaining single strand residue was digested with S1 nuclease. The vector was cut with BamHI and the large fragment was isolated (FIG. 17). The DNA molecule coding for VAC-beta was ligated into the vector thus prepared. For this purpose, the 440 bp long MaeIII-BamHI fragment which contains the codons 13 to 157 was isolated from the clone pRH203. The missing 5' end was supplemented using oligonucleotides:
EBI-307
5' CCATGGCTTGGTGGAAAGCTTGGATC-GAACAGGAAGGT 3'
3' GGTACCGAACCACCTTTCGAACCTAGCT-TGTCCTTCCACAGTG 5' EBI-306

Optimum codons were used for *E. coli* (e.g. R. Grantham et al., Nucleic Acids Res. 8 (1980), 1893–1912). This codon exchange resulted in a new HindIII site at codons 5 to 7. After re-cutting with BamHI, the 5' terminal VAC fragment was ligated into the prepared pER103 vector. The vector formed was designated pRH211. In order to complete the region coding for VAC-beta, the 1230 bp long BamHI-SphI fragment was isolated from the clone pRH201. The approximately 200 bp long pBR322 section from BamHI to SphI from the plasmid pRH211 was removed and replaced by the corresponding VAC cDNA part. This resulted in the vector pRH212. The EcoRI-BamHI fragment which contains the Trp promoter (S. marcescens), the ribosomal binding site and the synthetically produced beginning of the VAC-beta gene was checked by sequencing. The plasmid-encoded VAC-beta was detected in a maxicell system (A. Sancar et al., J. Bacteriol. 137 (1979), pp. 692–693).

The construction of an expression vector starting from pRH284T is particularly preferred for the expression of VAC-beta. For this purpose, the insert coding for VAC-beta was ligated into the expression vector in suitable manner. The vector pRH212, for example, may be used as starting material for this insert.

The expression vector pRH284T was linearized with SacI and the 3' overhanging ends were converted into straight ends using DNA polymerase I/Klenow fragment and dGTP. The vector was recut with SalI and the large fragment was isolated. The HindIII-SalI insert of clone pRH212 was isolated. The pair of oligonucleotides

5' GCTTGGTGGAA 3' EBI-684
3' CGAACCACCTTTCGA 5' EBI-685 were ligated with the VAC-beta insert and the prepared pRH284T. E. coli HB101 was transformed with the ligase solution. The resulting clone was designated pRH292 (FIG. 18).

Since the tetracycline resistance gene has been deleted from the promoter to the SalI site in the expression vectors pRH291 (VAC-α) and pRH292 (VAC-β), these vectors cannot confer any tetracycline resistance. Tetracycline-resistant expression vectors are obtained for example by the construction according to the plan in FIG. 36. VAC-α and VAC-β cDNA each have an SphI site in the 3' untranslated region. In the β-lactamase gene of the vector there is a PvuI site. Both recognition sequences are singular. Therefore, by cutting with PvuI and SphI, part of the β-lactamase gene, the phoA promoter and the cDNA containing the entire coding part of the VAC-α or β plus some 3' untranslated cDNA can be freed from the two expression vectors. On the other hand by cutting with PvuI and EcoRI the remainder of the β-lactamase gene, the replication origin and the entire tetracycline resistance gene including the promoter can be freed from the plasmid pAT153. If the SphI or EcoRI ends are straightened by enzymatic treatment, compatible ends are obtained. If vector fragment and the fragment containing VAC-α or VAC-β cDNA are ligated, expression vectors are formed which contain the complete tetracycline resistance gene: pGN25 (VAC-α), pGN26 (VAC-β).

Competent host organisms, particularly E. coli, more especially E. coli HB101 were transformed with the expression vectors thus prepared and cultivated in suitable media.

A medium which is well suited to the expression of VAC-alpha and VAC-beta will now be described with its components:
0.2–2.0 g/l $(NH_4)_2HPO_4$
0.1–1.5 g/l $K_2HPO_4.3H_2O$
0.1–5 g/l KCl
0.1–10 g/l NaCl
0–5 g/l $NH_4Cl$
0.1–5 g/l $MgSO_4. 7H_2O$
0.001–0.1 g/l $CaCl_2$
1–50 mg/l thiamine.HCl
0.5–100 mg/l $(NH_4)_2Fe(SO_4)_2.6H_2O$
0.1–5 mg/l $AlCl_3.6H_2O$
0.1–10 mg/l $CoCl_2.6H_2O$
0.2–5 mg/l $KCr(SO_4)_2.12H_2O$
0.1–5 mg/l $CuSO_4.5H_2O$
0.05–1 mg/l $H_3BO_3$
0.1–5 mg/l $MnSO_4.H_2O$
0.1–5 mg/l $NiSO_4. 6H_2O$
0.1–5 mg/l $Na_2MoO_4.2H_2O$
0.1–5 mg/l $ZnSO_4.7H_2O$
10–30 g/l casein hydrolysate (Merck Art. No. 2238)
0–100 g/l casein hydrolysate (Sigma C9386)
0.10–1 mg/l cysteine
0–10 g/l yeast extract (Difco)
0–2 g/l citric acid
0–50 g/l glucose (start)
5–50 g/l glucose, (fed in during fermentation)

A medium with the following composition is particularly suitable:
Media: 1) Preliminary Culture
10 g/l tryptone
5 g/l yeast extract
4 g/l glucose
9 g/l $Na_2HPO_4.2H_2O$
1 g/l $NH_4Cl$
1 g/l KCl
1 ml/l 1M $MgSO_4.7H_2O$
100 mg/l ampicillin
Starting pH=7.2
2) Main Culture
0.68 g/l $(NH_4)_2HPO_4$
0.62 g/l $K_2HPO_4.3H_2O$
2.33 g/l KCl
0.5 g/l NaCl
0.53 g/l $NH_4Cl$
1.23 g/l $MgSO_4.7H_2O$
0.011 g/l $CaCl_2$
10 mg/l thiamine.HCl
3.92 mg/l $(NH_4)_2Fe(SO_4)_2.6H_2O$
0.72 mg/l $AlCl_3.6H_2O$
0.71 mg/l $CoCl_2.6H_2O$
1.5 mg/l $KCr(SO_4)_2.12H_2O$
0.75mg/l $CuSO_4.5H_2O$
0.19 mg/l $H_3BO_3$
0.51 mg/l $MnSO_4.H_2O$
0.79 mg/l $NiSO_4.6H_2O$
0.73 mg/l $Na_2MoO_4.2H_2O$
0.86 mg/l $ZnSO_4.7H_2O$
21 g/l casein hydrolysate (Merck Art. No. 2238)
25 g/l casein hydrolysate (Sigma C9386)
100 mg/l cysteine
2 g/l yeast extract
1 g/l citric acid
11 g/l glucose.$H_2O$ (start or feed)

For fermentation, for example, the pre-culture medium was inoculated with E. coli transformed with the corresponding expression vector and incubated with stirring and with the introduction of oxygen. Some of this pre-culture was then transferred into a fermenter with the main culture medium and cultivated with stirring and aeration. During the fermentation period, the concentration of glucose and the partial oxygen pressure were observed and adjusted to the optimum. After about 20 hours' fermentation the mixture was cooled, the nutrient medium was separated from the biomass and frozen.

Figure 19A:
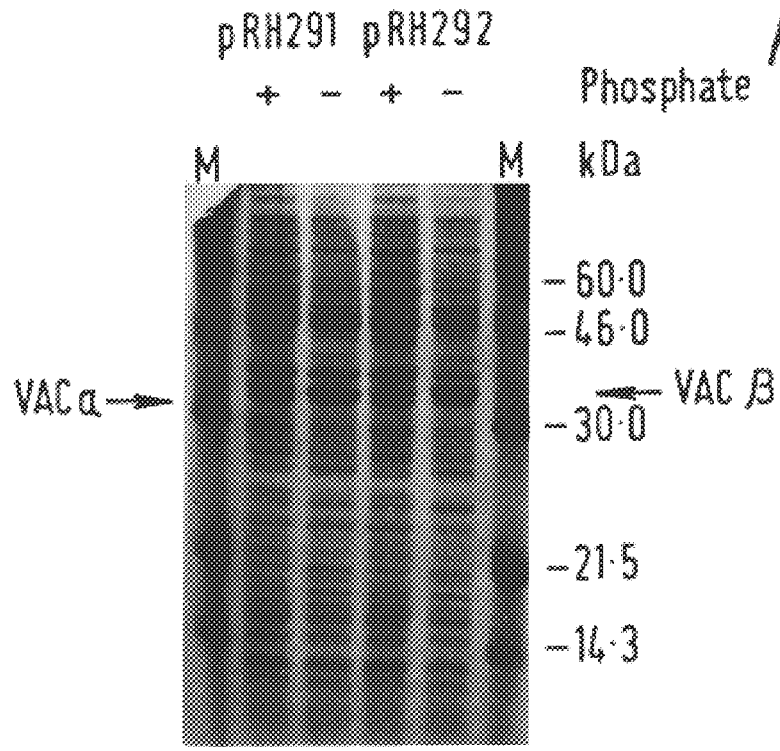
Figure 19B:
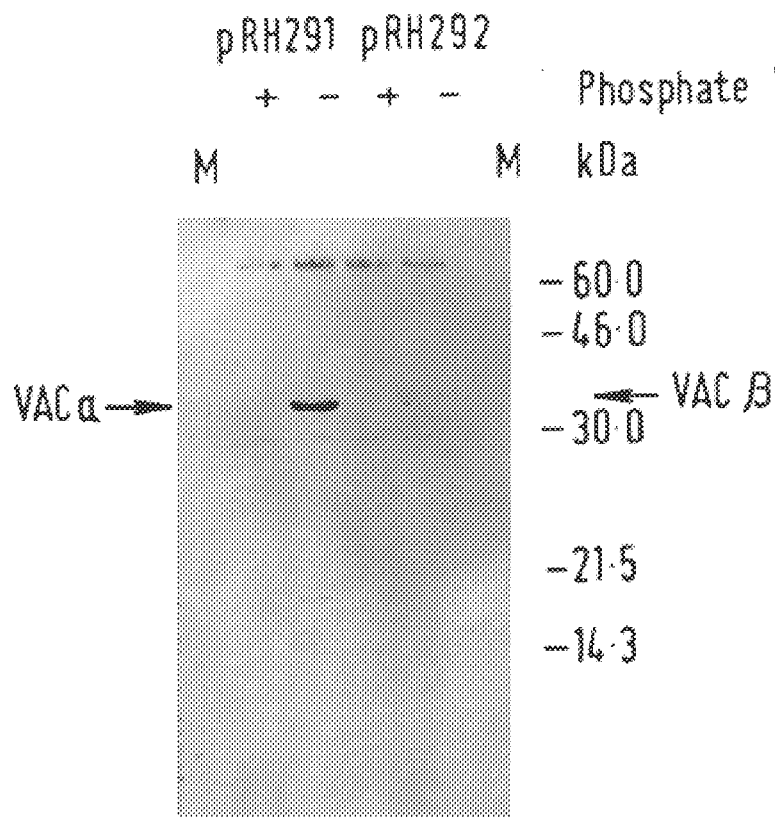
Figure 20:
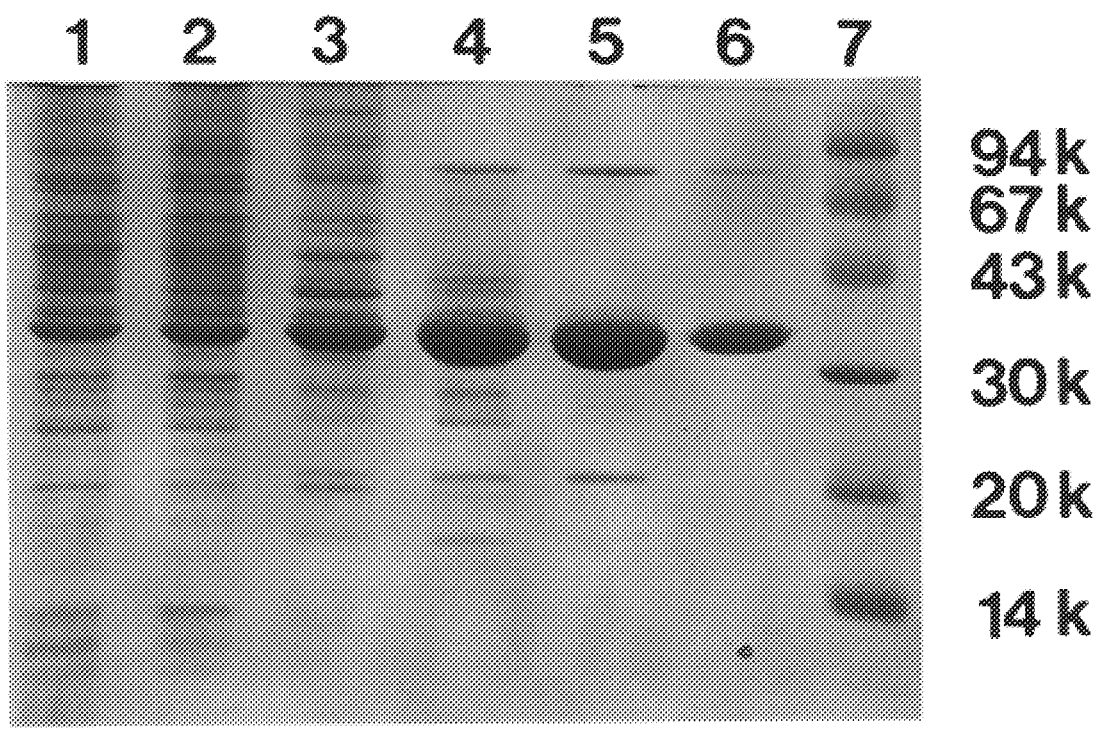
Figure 21:
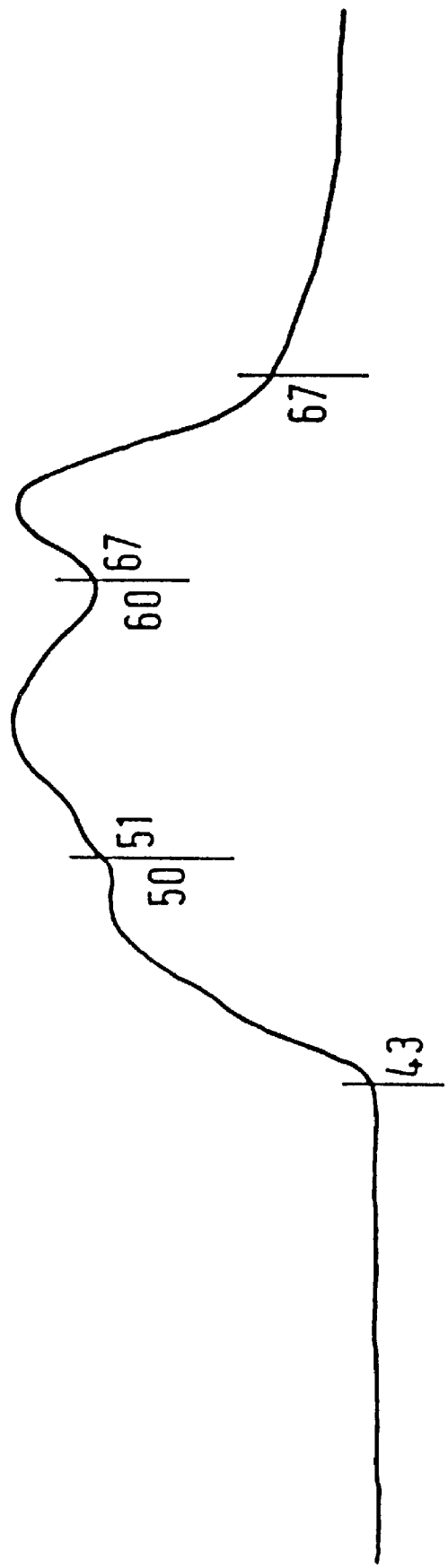
Figure 22:
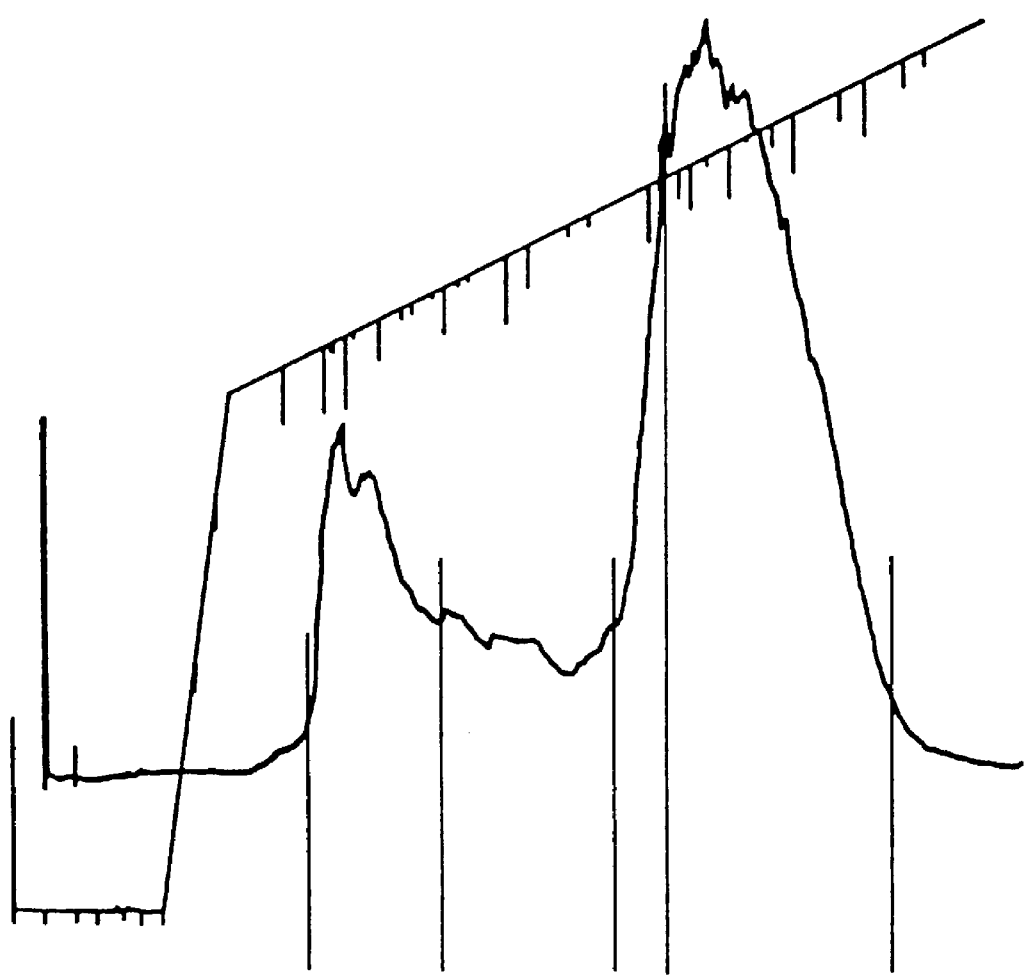
Figure 23:
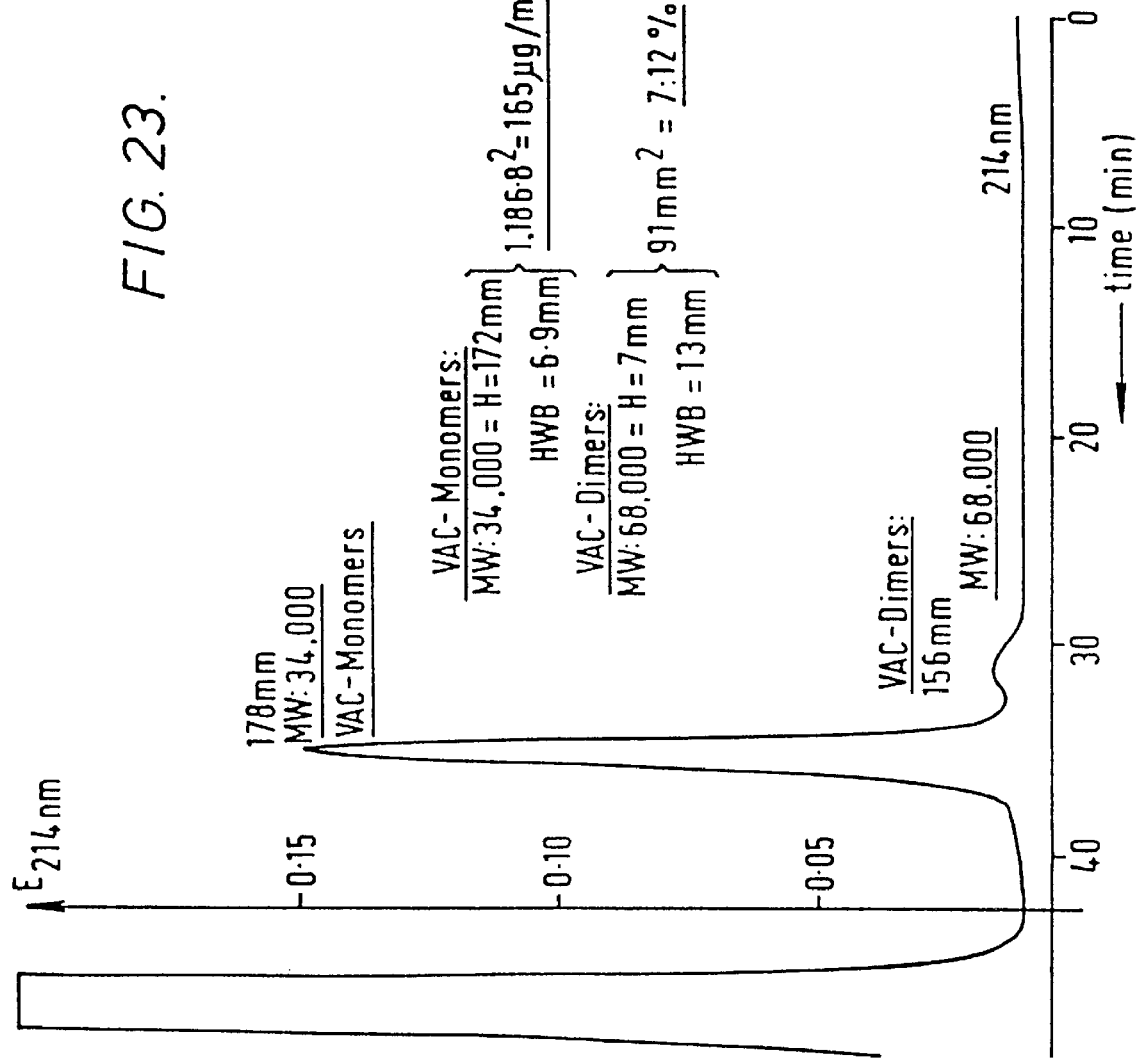
Figure 24:
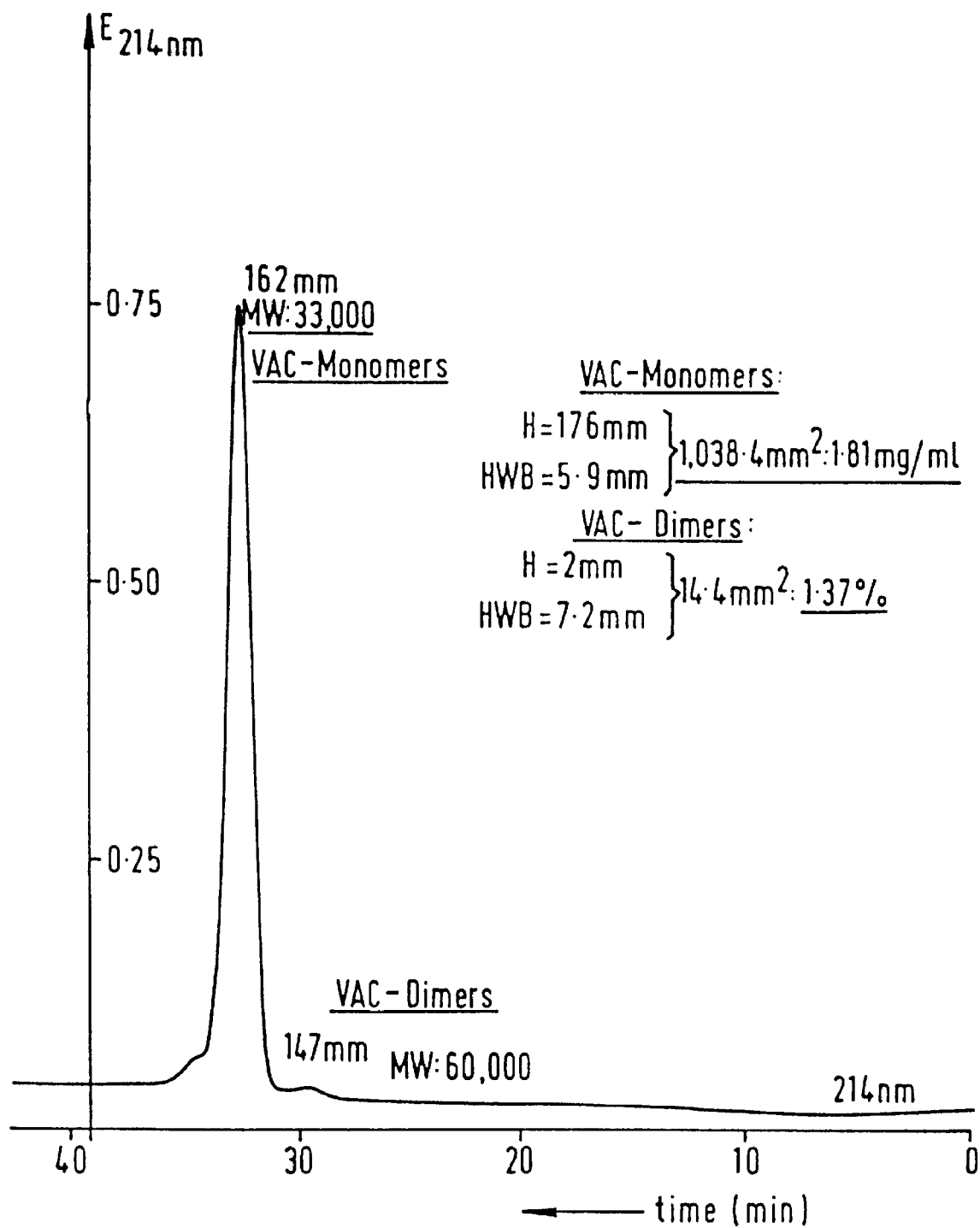
Figure 25:
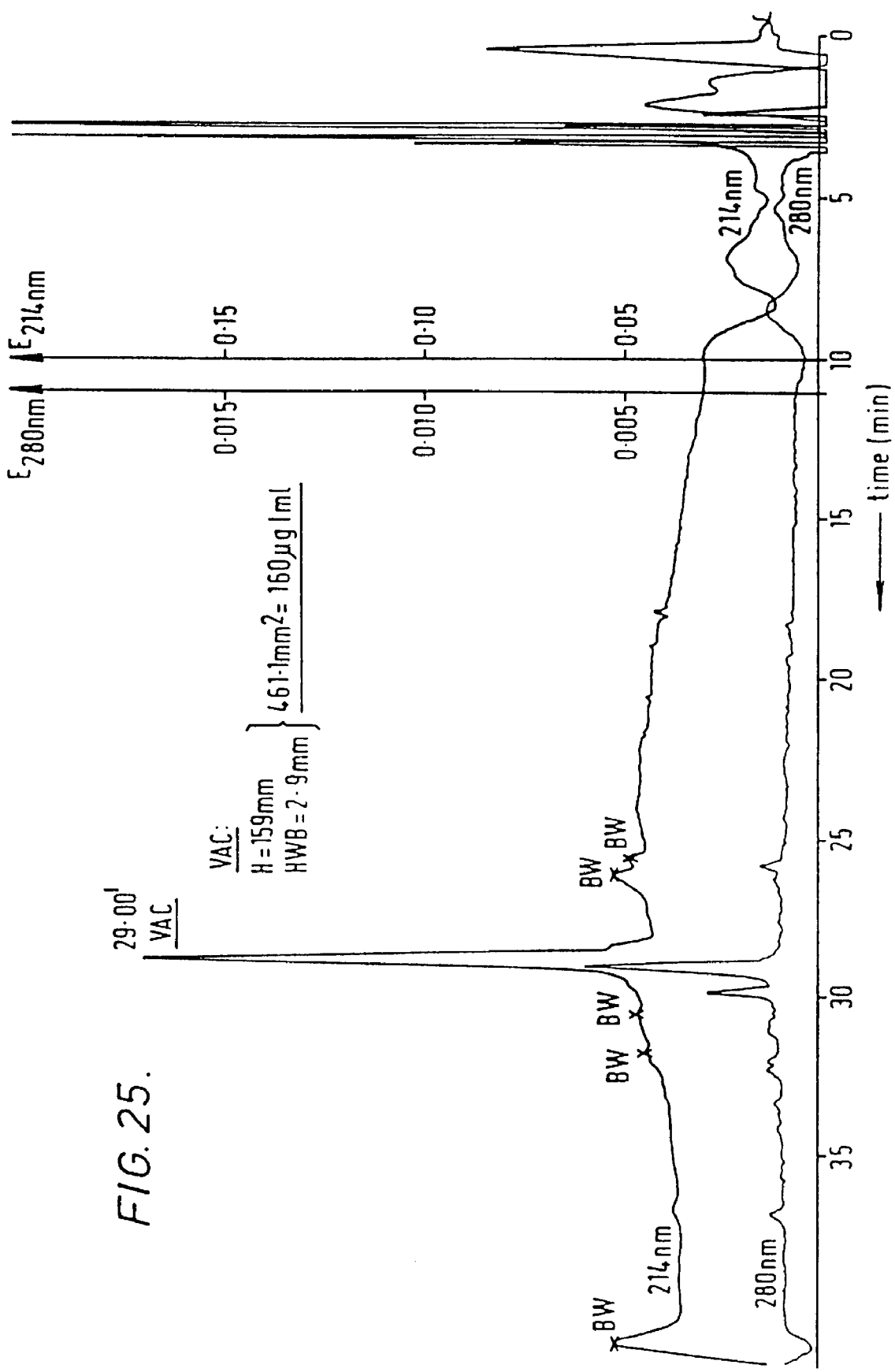
Figure 26:
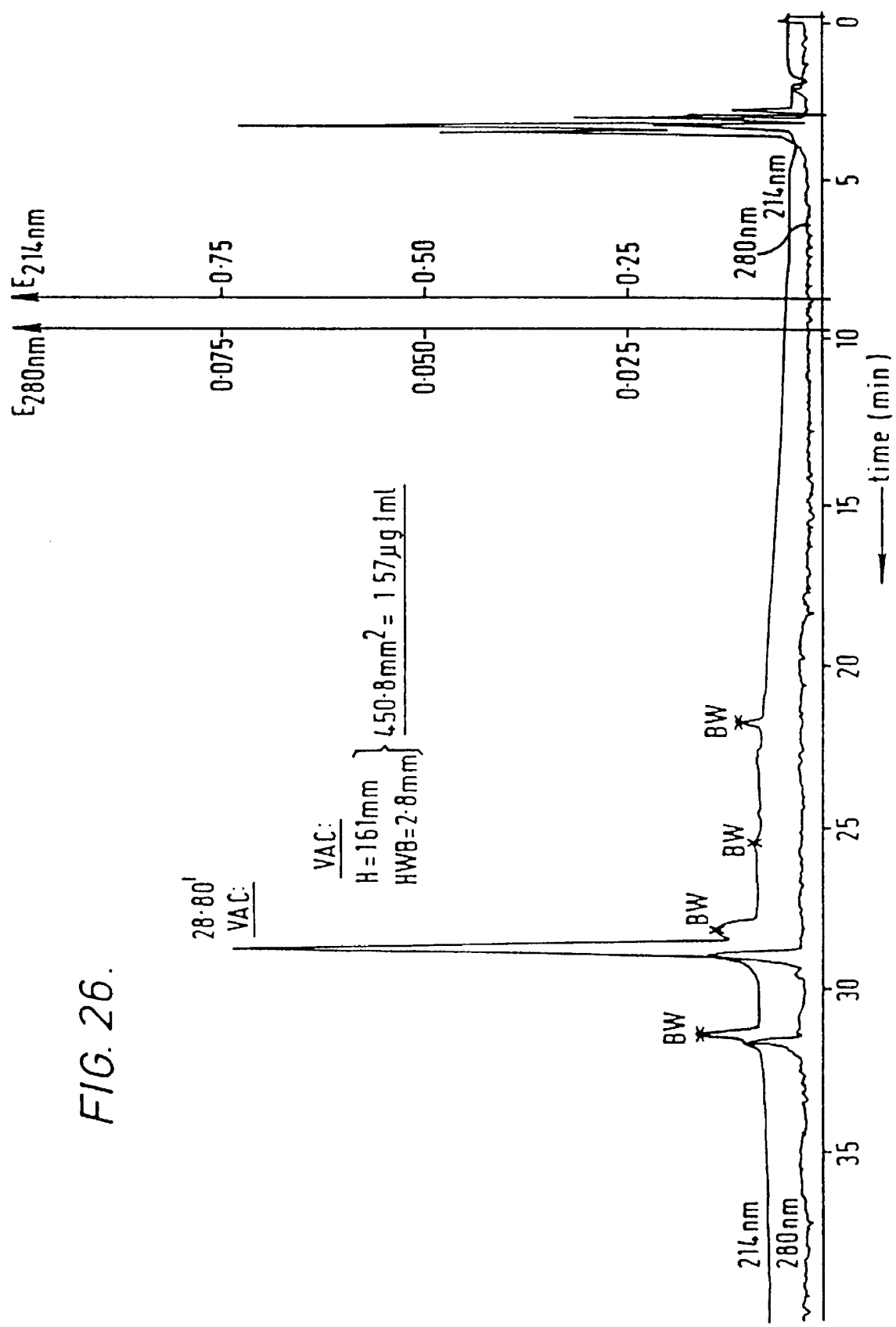
Figure 27:
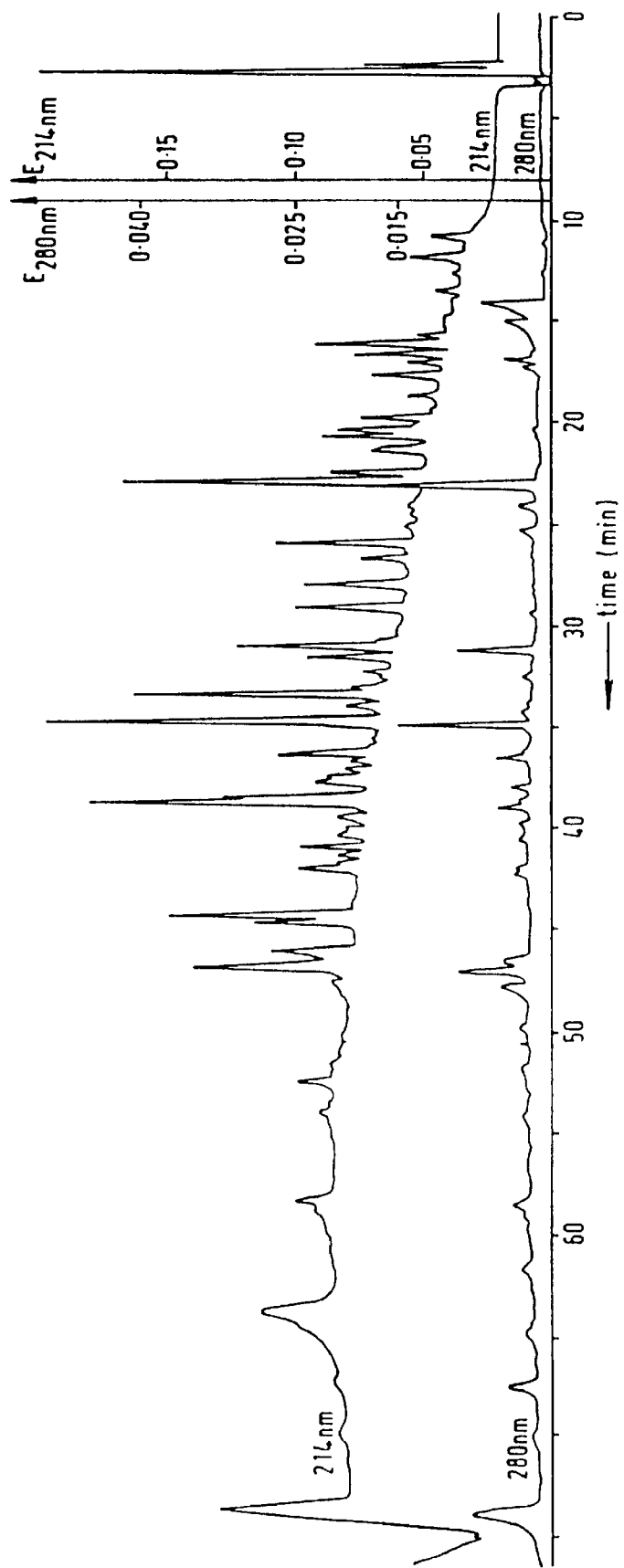
Figure 28:
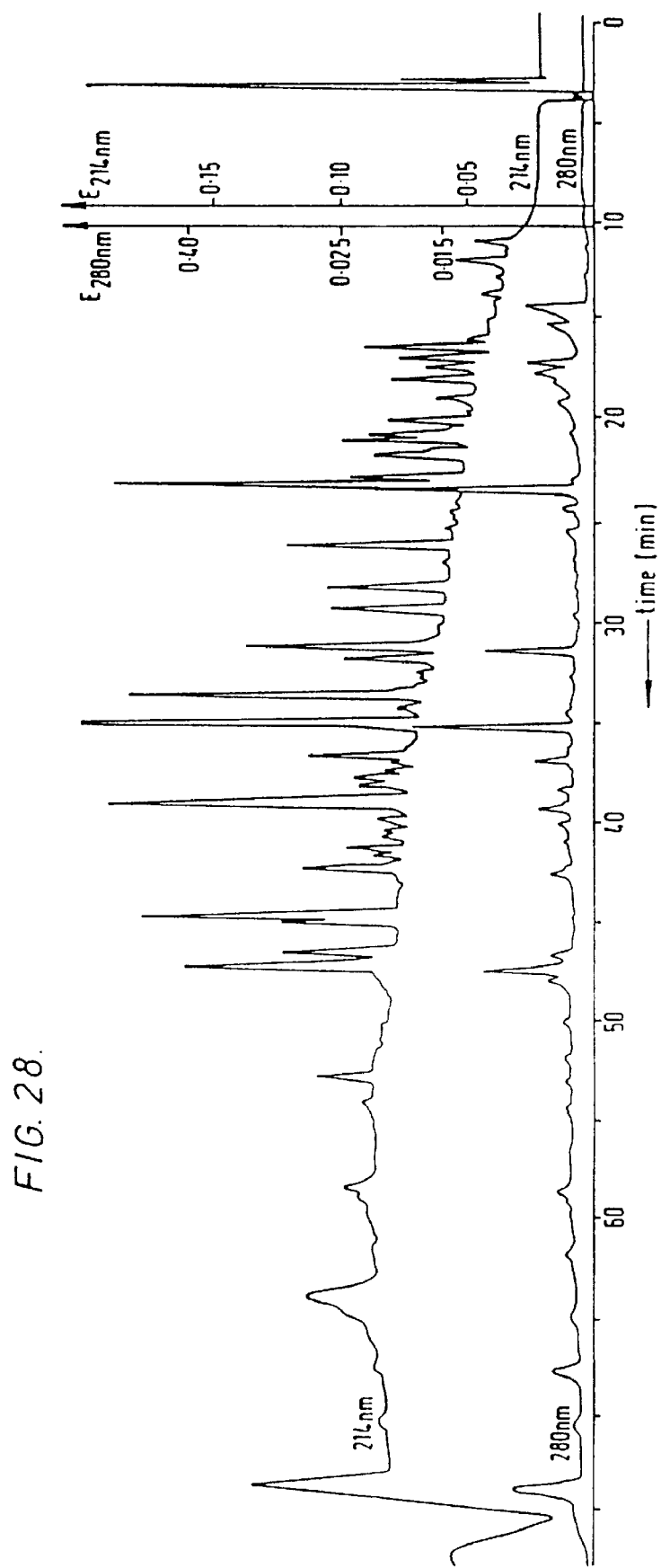
Figure 29:
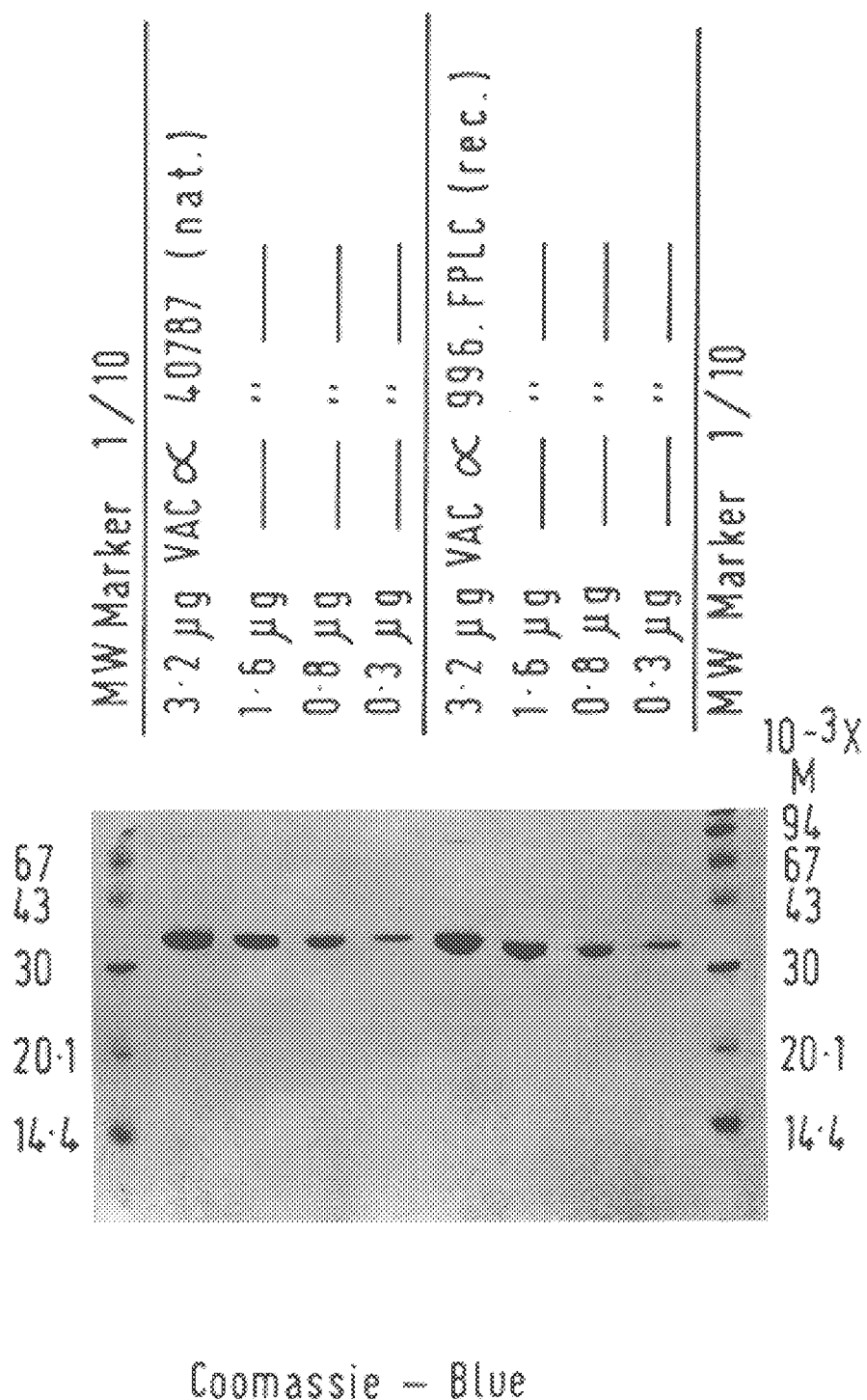
Figure 30:
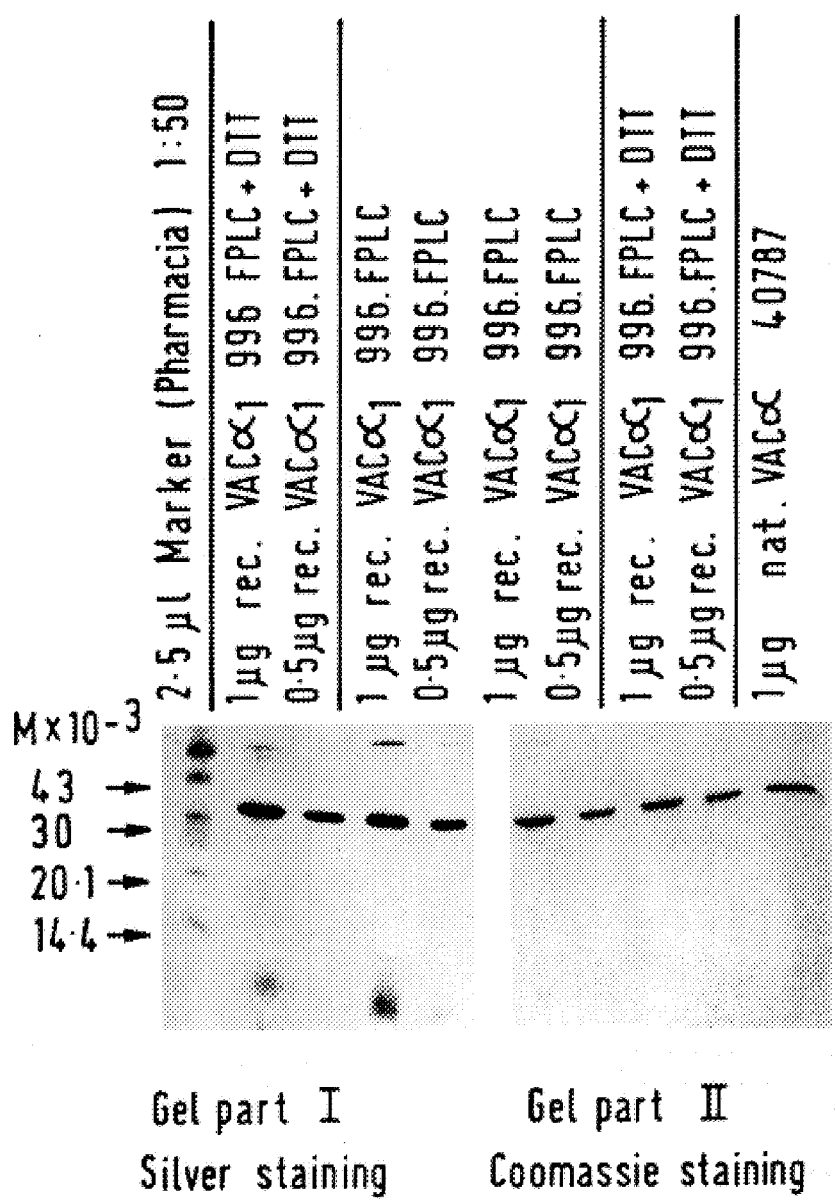
Figure 31:
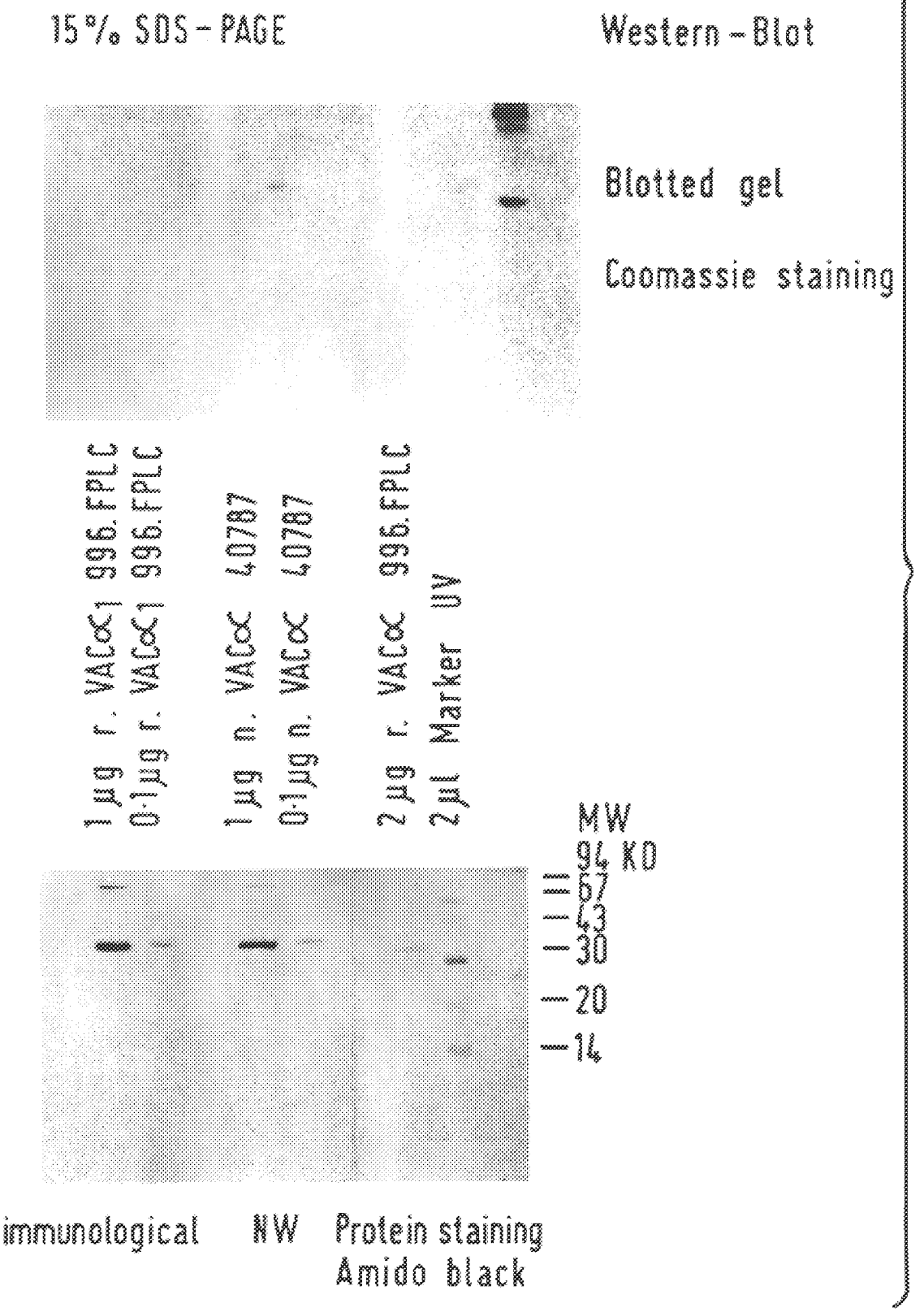
Figure 32:
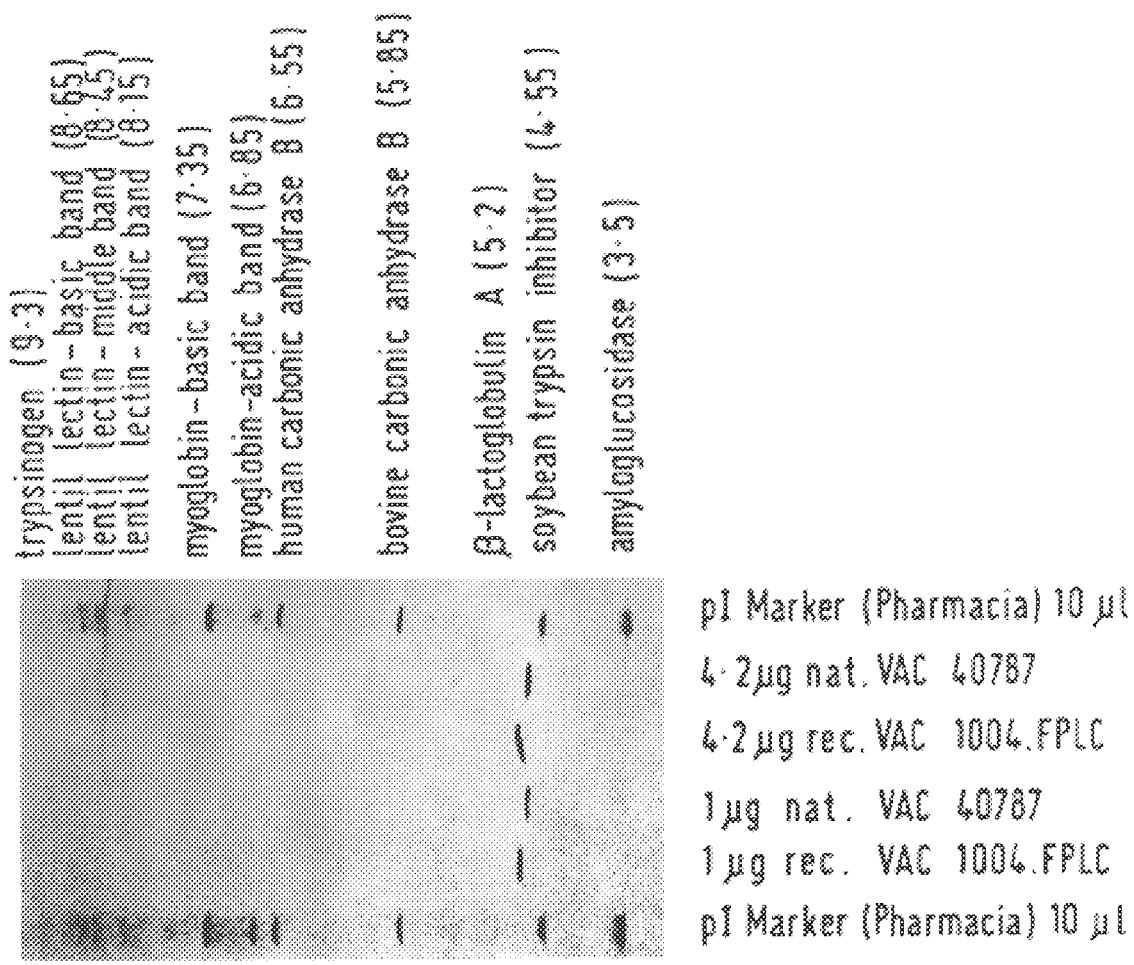
Figure 32A:
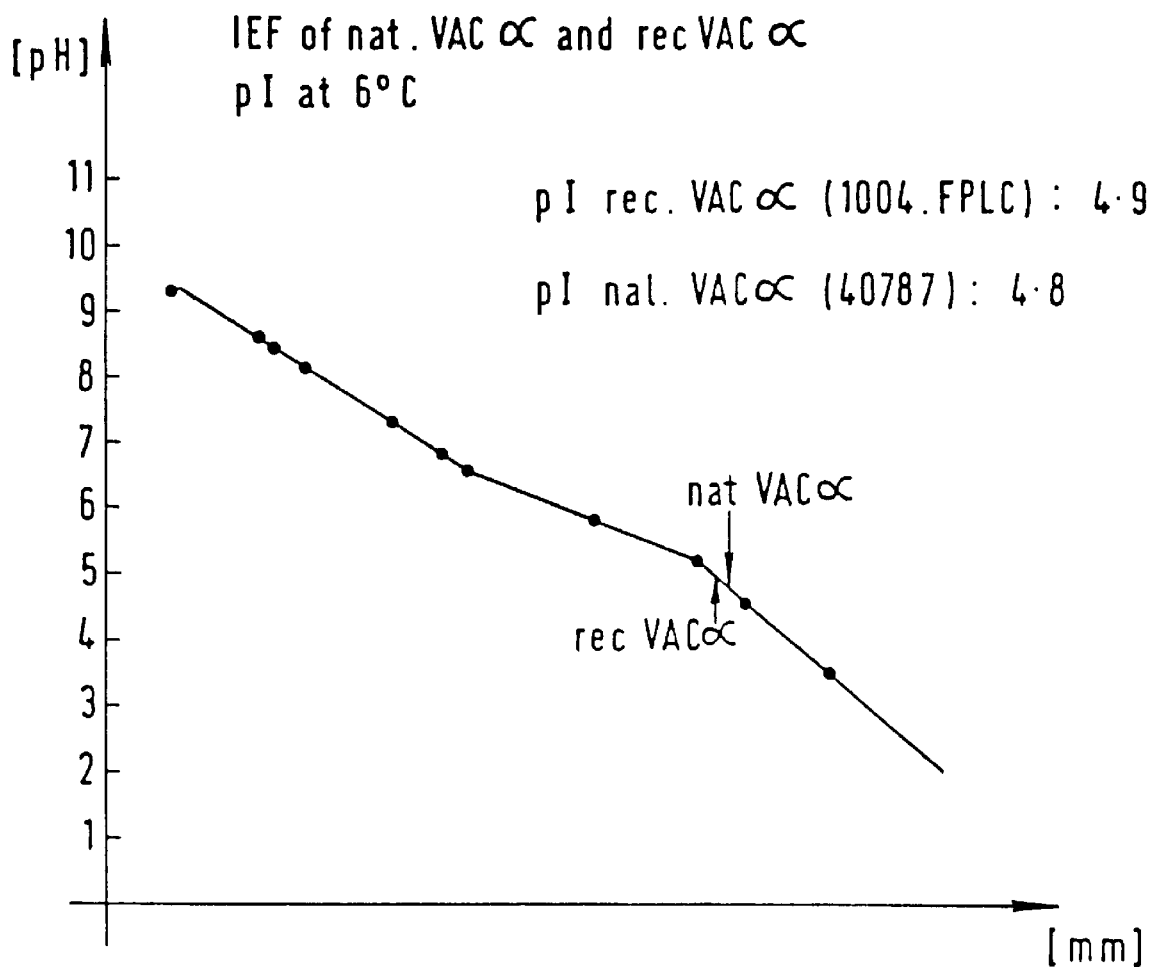

The expressed proteins were detected, for example, by Western blot. The results are shown in FIG. 19.

"+phosphate" is the control without any expression, "−phosphate" indicates the expression of VAC-alpha (clone HB101/pRH291) or VAC-beta (clone HB101/pRH292) protein under the control of the alkaline phosphatase promoter. Both VAC-alpha and VAC-beta protein can already be detected on the stained gel. The quantity of VAC proteins formed is, surprisingly, at least 20 mg/l/OD$_{600\,nm}$ bacterial culture.

The Western blot clearly shows the stained VAC-alpha band. In addition, some proteins of lower molecular weight can be seen in the range up to 30 kD, possibly formed by proteolytic cleavage at the N and/or C terminus of the VAC-alpha protein. Another noticeable feature is a protein recognized by the antiserum in the range below 20 kD, which could be a half molecule of VAC-alpha protein formed by proteolysis. Surprisingly, VAC-beta was also recognized by anti-VAC antiserum. Since this band is much more faintly coloured than the VAC-alpha band but the VAC-beta band in the Coomassie Blue stained gel corresponds to the VAC-alpha in its intensity, it can be concluded that recognition of the VAC-beta protein by the anti-VAC antiserum is substantially poorer than recognition of the VAC-alpha protein.

In order to isolate and purify the expressed proteins, the frozen biomass was suspended in a suitable lysis buffer. The cells were then mechanically destroyed, for example using a Manton-Gaulin press. After the addition of a precipitating agent for non-protein constituents such as polyethyleneimine the solid components were removed, for example, by centrifuging. After the proteins had been precipitated, preferably by ammonium sulphate fractionation, dissolving of the precipitate, removal of the precipitation agent and clarification of the solution, the extract thus obtained was subjected to various chromatographic purification steps. Instead of the precipitation of the proteins the crude VAC extract can also be purified by chromatographic preliminary purification so that it can then be subjected to a purification cycle. SiO$_2$ has proved suitable, for example, as a column material for the preliminary purification, but other materials with similar properties are also suitable. According to the invention, Silica Catalyst Carrier, grade 953W made by Messrs Grace was used. A chromatographic purification cycle suitable for purifying the proteins according to the invention consisted of for example a DEAE fast flow Sepharose, a Sephacryl S-200 High Resolution and a Q-Sepharose Fast Flow Chromatography. The purity of the proteins according to the invention thus obtained was determined by SDS-PAGE, Western blot, gel permeation HPLC, reverse phase HPLC amino-acid determination, N-terminal sequencing and isoelectric focussing.

The parameters which have to be adhered to for all the steps of cultivation, isolation and purification, such as temperature, ratios of quantities, sequence of the individual steps, pH values, particular reagents, etc., are known to those skilled in the art. The examples which follow may, if desired, be suitably modified in a manner known to the person skilled in the art.

It is particularly important to determine whether a VAC protein produced by genetic engineering and hereinafter referred to as r-VAC for short, is identical to the VAC protein obtained from natural material (see EPA 0 181 465), hereinafter referred to as VAC; identical both in its structure and its biological properties.

The following methods were used to answer these questions:

1. gel permeation HPLC
2. reverse phase HPLC
3. N-terminal sequencing
4. tryptic peptide map
5. SDS gel electrophoresis
6. Western blot
7. isoelectric focussing The gel permeation HPLC shows a molecular weight of 34,000 for VAC and 33,000 for r-VAC, which can be regarded as equivalent within the range of accuracy of the method. It should be borne in mind that strictly speaking the column used differentiates not according to molecular weight but according to molecular size.

In reverse phase HPLC, both proteins elute after a retention time of about 29 minutes.

N-terminal sequencing of the "r-VAC" up to amino acid 39 showed a 100% agreement with the expected sequence. N-terminal methionine, often additionally found in proteins produced by genetic engineering, could not, surprisingly, be detected. As expected, the N-terminus of r-VAC is present in unblocked state.

A comparison of tryptic fragmentation showed a virtually identical peptide pattern.

A comparison of the two proteins by SDS-PAGE also showed virtually identical behaviour. Both contain dimeric forms which are obviously bound via disulphide bridges and can be reduced by dithiothreitol.

Similarly immunological comparison by Western blot confirmed that the two proteins were identical.

The difference of +0.1 pH units in r-VAC found when determining the isoelectric point can be explained by the free N-terminus.

To check the biological activity of r-VAC, various coagulation tests were carried out and the results were compared with those which are obtained with VAC from natural material. All the tests carried out, the modified prothrombin time test and the thrombin test, as well as the factor $X_a$ generation in tissue factor-activated plasma clearly prove that r-VAC has biological activity and that this is indistinguishable from that of VAC from natural material.

The cDNA derived amino acid sequence ot VAC β shows a 54% homology with VACα. Based on these findings we investigated some biological activities of VAC β and compared them with VAC α.

1.) The Effects of VAC α and VAC β on the Prothrombinase Activity:

FIG. 47 shows that the two proteins VAC α and VAC β exert the same inhibitory effect on the prothrombinase activity. This suggests that VAC α and VAC β inhibit coagulation via the same mechanism.

2. Phospholipase Inhibitory Activities of VAC

On the basis of their primary structure VAC α and VAC β can be categorized into the family of the annexins (Geisow, M. J. (1986) Febs Letters 203, 99–103). Some other members of this family, e.g. calpactin I and II, have been demonstrated to be phospholipase inhibitors. They exhibit this activity through a calcium dependent binding to the phospholipids and thereby blocking the access of the phospholipase to its substrate (Davidson, F. F., Dennis, E. A., Powell, M., & Glenney, J. R., Jr (1987), J. Biol. Chem. 262, 1698–1705).

Since VAC α and VAC β bind calcium dependently to phospholipids, we investigated whether the two proteins have possible antiphospholipase activities also. A procedure with $^3$H-oleic acid labeled *E. coli* was chosen for this purpose.

FIGS. 48 and 49 illustrate that VAC α as well as VAC β inhibit phospholipase $A_2$ activity. Both proteins are furthermore equally active under the chosen conditions. 50% inhibition is accomplished by approximately 65 nM VAC α or VAC β. Decreasing the substrate concentration two fold results in a two fold decrease of the $ID_{50}$ of VAC. This indicates that VAC acts at the substrate level. Hence, it is likely that VAC binds to the phospholipid membranes and thereby inhibits phospholipase activity.

Calpactin I has been shown to bind to phospholipid membranes at the micromolar $Ca^{++}$ level (Drust, D. S. & Creutz, C. E. (1988) Nature 331, 88–91). We investigated whether VAC is able to inhibit phospholipase activity at low calcium concentration. Since the pancreatic phospholipase $A_2$ was inactive at $Ca^{++}$ concentrations below 50 $\mu$M, this is the lowest concentration tested. FIGS. 50 and 51 show the calcium dependency of VAC induced inhibition of phospholipase activity. At all $Ca^{++}$ concentrations tested VAC $\alpha$ as well as VAC $\beta$ exhibited inhibitory activities. However, there appeared to be a functional difference between VAC $\alpha$ and VAC $\beta$. At the lowest $Ca^{++}$ concentration VAC $\beta$ was significantly more effective then VAC $\alpha$. This could imply that VAC $\beta$ requires less $Ca^{++}$ for membrane binding.

VAC proteins obtained according to the invention may be converted into other VAC proteins (peptides) in a manner known per se.

Tests have shown that disulphide bridges have nothing to do with the coagulation-inhibiting activity of natural VAC. Depending on the choice of host cell, it cannot be ruled out that the cysteine groups will become linked in the primary translation product, forming disulphide bridges, in a way which differs from the naturally occurring process. It is possible that the "false" tertiary structure of the product established will lead to a reduction in or even loss of, but possibly an improvement in, the valuable pharmacological properties, particularly the coagulation-inhibiting activity, and this can be determined using the above-mentioned VAC assays. In such cases it may be convenient to cleave the disulphide bonds with a suitable reducing agent and to treat the reduced polypeptide with a suitable oxidizing agent to re-form the disulphide bonds. Using the VAC activity of the product formed it is possible to determine whether the conditions selected (reducing and/or oxidizing agent) have resulted in the desired increase in biological activity or whether the conditions have to be modified in known manner.

Examples of suitable reducing agents for cleaving disulphide bridges include thiol compounds such as thiophenol, 4-nitrothiophenol, 1,4-butanedithiol and particularly 1,4-dithiothreitol. The reduction is advantageously carried out in an aqueous/alkaline medium, for example in a dilute aqueous solution of an alkali metal hydroxide, e.g. sodium hydroxide, alkali metal carbonate, e.g. sodium carbonate, or an organic base, particularly a tri-lower alkylamine, e.g. triethylamine, at ambient temperature.

Oxidizing agents which are suitable for re-forming disulphide bonds in the reduced polypeptides include, for example, oxygen from the air, which is passed through an aqueous solution of the polypeptide, to which, if desired, a catalytic quantity of a salt of a transition metal has been added, e.g. iron(III) sulphate, iron(III) chloride or copper(II) sulphate; iodine, also in the form of the potassium iodide adduct $KI_3$, which is preferably used in alcoholic, e.g. methanolic, or aqueous-alcoholic, e.g. aqueous-methanolic solution; potassium hexacyano-ferrate(III) in aqueous solution; 1,2-diiodoethane or dimethyl or diethyl azodicarboxylate, which are reacted in water or in a mixture consisting of water and a water-miscible alcohol, e.g. methanol. The oxidation is carried out, in particular, at ambient temperature.

The separation of the reagents, particularly the salts and the oxidizing or reducing agents and their secondary products from the desired VAC compound is effected by methods known in the art, for example by molecular weight filtration, e.g. using Sephadex or Biogel.

A mixture of compounds with VAC activity obtainable according to this process can be separated into the individual components in known manner. Suitable methods of separation include, for example, chromatographic methods such as adsorption chromatography, ion exchange chromatography, HPLC or reverse phase HPLC, and also multiplicative distribution or electrophoretic methods, e.g. electrophoresis on cellulose acetate or gel electrophoresis, particularly polyacrylamide gel electrophoresis ("PAGE").

The compounds which may be prepared according to the invention may occur not only in free form but also in the form of their salts, particularly their pharmaceutically acceptable salts. Since they contain a plurality of amino acid groups with free amino groups, the compounds according to the invention may, for example, occur in the form of acid addition salts. The acid addition salts used may be, in particular, physiologically acceptable salts with conventional, therapeutically useful acids; examples of inorganic acids include the hydrohalic acids such as hydrochloric acid and also sulphuric and phosphoric or pyrophosphoric acid; examples of organic acids include, primarily, sulphonic acids such as benzenesulphonic or p-toluenesulphonic or lower alkanesulphonic acids such as methanesulphonic acid, and carboxylic acids such as acetic, lactic, palmitic and stearic acid, malic, tartaric, ascorbic and citric acid. Since the VAC compounds also contain amino acid groups with free carboxyl groups, they may also occur as metal salts, particularly as alkali metal or alkaline earth metal salts, e.g. sodium, calcium or magnesium salts, or as ammonium salts derived from ammonia or a physiologically acceptable organic nitrogen-containing base. However, since they also contain free carboxyl groups and free amino groups, they may also occur as internal salts.

Depending on the procedure used, the compounds according to the invention are obtained in free form, in the form of acid addition salts or salts with bases. The free compounds may be obtained from the acid addition salts and the salts with bases in known manner, for example by adjusting the pH to the isoelectric point. Similarly, therapeutically acceptable acid addition salts or salts with bases may in turn be obtained from the free compounds by reacting with acids or bases, e.g. with those which form the above-mentioned salts, and by evaporation or lyophilization.

The property of antibodies to bind specific antigens is of practical use outside the body in qualitative and quantitative measurement (immunoassay) and in the purification of antigens (immunoaffinity chromatography). Serum from immunized animals normally contains a variety of different antibodies which react with the same antigen at different binding sites with different affinities, and also antibodies against other antigens which reflect the earlier experiences of the individual. The successful use of antibodies to detect and purify antigens does, however, require high specificity and reproducibility.

Homogeneous antibodies which satisfy these requirements have been made accessible by the hybridoma technique described by Köhler and Milstein (17). Basically, the technique consists in fusing antibody-secreting B-lymphocytes, e.g. from the spleen of immunized animals, with tumour cells. The hybridoma cells formed combine the capacity for unlimited replication by division with the ability to form and secrete a uniform type of antibody. By cultivation in a selective medium in which non-fused tumour cells die off but hybridoma cells replicate and by suitable manipulation, it is possible to obtain and cultivate clones, i.e. cell populations which are derived from a single hybridoma cell and are genetically identical, and the monoclonal antibodies produced by the cells are then isolated.

The present invention relates to monoclonal antibodies against VAC, hybridoma cells which produce such antibodies and processes for preparing them. Hybridoma cell lines and the monoclonal antibodies which react specifically with VAC and which are secreted thereby are preferred. The process for preparing monoclonal anti-VAC-α and anti-VAC-β antibodies is characterized in that mice are immunized with VAC, B-lymphocytes from such immunized animals are fused with myeloma cells, the hybridoma cells formed are cloned, then cultivated in vitro or by being injected into mice and antibodies are isolated from the cultures.

The invention further relates to immunoaffinity chromatography columns and test kits for immunoassays which contain these antibodies.

According to the process of the invention, mice such as Balb/c mice are immunized in known manner. In a preferred embodiment, VAC is injected roughly every week or at longer intervals over a period of several weeks, for example 5 to 12 weeks, until a sufficient number of antibody-producing B-lymphocytes has formed.

To increase the immunogenicity of the VAC used, it was coupled to strongly immunogenic carriers such as, for example, heterologous albumin or "keyhole limpet hemocyanin" (KLH). Preferably, different VAC/KLH preparations were used, and according to one immunization plan, immunization was continued until sufficient antibody-producing cells had formed, for example up to about 40 weeks.

Organs which contain B-lymphocytes, e g. spleen cells, are taken from the immunized mice and fused with those myeloma cells cannot grow, as a result of mutation, in a selective culture medium. Such myeloma cells are known and include, for example, those designated X63-Ag8, X63-Ag8.6.5.3, MPC-11, NSl-Ag4/1, MOPC-21 NS/1 or SP 2/0. In a preferred embodiment, spleen cells from immunized mice are fused with myeloma cells of the cell line X63-Ag8.6.5.3.

The fusion is carried out by known methods by mixing the B-lymphocytes and the myeloma cells with the addition of a cell fusion agent such as polyethyleneglycol, Sendai virus, calcium chloride or lysolecithin. Fusion is preferably carried out in the presence of polyethyleneglycol, for example with a molecular weight of between 1000 and 4000.

After the fusion, the resulting hybrids are cultivated by a known method in a selective culture medium to which hypoxanthine, aminopterine and thymidine (HAT medium) has been added. Non-fused myeloma cells cannot grow in this medium and will therefore die off, as will normal lymphocytes.

The supernatants from the hybridoma cultures can be tested by known methods for their content of specific antibodies, for example by radioimmunoassay, ELISA or agglutination. Surprisingly, it is found that hybridoma cells which secrete antibodies specifically against VAC can be obtained by the method described. The hybridoma cells which produce antibodies of the desired specificity are selected out of the mixture of different hybridoma cells produced by fusion by cloning. To do this, cultures are set up starting from a single growing cell by a method known as "limiting dilution".

For mass production, the hybridoma cell clones which are producing antibodies of the desired specificity are either cultivated in vitro in known media or injected into mice for replication. In a preferred embodiment hybridoma cells are injected into mice which have been pre-treated with pristane, ascitic fluid is removed and antibodies are isolated therefrom by precipitation with ammonium sulphate solution.

The VAC-specific antibodies obtained by means of these hybridoma cells can be used in known manner to prepare immunoaffinity chromatography columns. In a preferred embodiment of the invention, a suitable carrier material (suspended in a buffer solution) is mixed with an antibody solution, any unbound components are then washed away and unoccupied sites of the carrier material are blocked. The VAC-specific antibodies obtained by means of the hybridoma cells can be used in known manner to prepare test kits. These test kits may be based on various methods, for example radioimmunoassay, latex agglutination, spot tests, competitive or sandwich immunoassay, enzyme immunoassay, immunofluorescence or immunochemical enzyme tests. These kits may contain, in addition to conventional antibodies of various origins, antibody conjugates with enzymes or fluorescence carriers, as well as VAC labelled with radioactive isotopes such as $I^{125}$ or conjugated with enzymes, for example horseradish peroxidase or alkaline phosphatase, as well as enzyme substrates, suitable buffers, gels, latex, polystyrene or other fillers and carriers.

The known proteins (peptides) obtainable according to the present invention have valuable pharmacological properties and may be used in preventive medicine or, more particularly, for therapeutic purposes.

The new VAC compounds according to the invention may therefore be used, analogously to natural VAC, for the therapy and prevention of thromboses and thromboembolisms, including the prevention of post-operative thrombosis, for acute shock treatment (e.g. in the event of septic or polytraumatic shock), for the treatment of consumption coagulopathy, in hemodialysis, hemoseparation, preserved blood and in extracorporeal circulation.

The invention also relates to pharmaceutical compositions which contain at least one of the compounds according to the invention or a pharmaceutically acceptable salt thereof, optionally together with a pharmaceutically acceptable carrier and/or excipients. These compositions may be used particularly in the above-mentioned indications if they are administered, for example, by parenteral route, e.g. by intravenous, intracutaneous, subcutaneous or intramuscular route, or topically.

The invention also relates to the use of the new compounds according to the invention and pharmaceutical compositions containing them for the preventative and therapeutic treatment of the human and animal body, particularly for the syndromes mentioned above, primarily for inhibiting blood coagulation inside and outside the human and animal body.

The dosage depends mainly on the specific form of administration and the purpose of the treatment or prevention. The size of the individual doses and the plan of administration can best be determined in the light of an individual assessment of the particular case: the methods required to determine relevant blood factors are well known to those skilled in the art. Normally, for an injection, the therapeutically effective quantity of the compounds according to the invention is in the range from about 0.005 to 0.1 mg/kg of body weight. The preferred range is from about 0.01 to about 0.05 mg/kg of body weight. The substance is administered by intravenous, intramuscular or subcutaneous injection. Accordingly, pharmaceutical preparations for parenteral administration, in the form of a single dose, contain about 0.4 to about 7.5 mg of the compound of the invention per dose, depending on the method of administration. In addition to the active substance, these pharmaceutical compositions usually also contain a buffer, e.g. a phosphate buffer, which is supposed to keep the pH between about 3.5 and 7, and also sodium chloride, mannitol or sorbitol to produce an isotonic solution. They may occur in freeze-dried or dissolved form, whilst solutions may contain a preservative with an antibacterial effect, e.g. 0.2 to 0.3% of methyl or ethyl 4-hydroxybenzoate. A preparation for topical use may take the form of an aqueous solution, lotion or jelly, oily solution or suspension, or a greasy or, more particularly, emulsified ointment. A preparation in the form of an aqueous solution may be obtained, for example, by dissolving the active substances according to the invention or a therapeutically acceptable salt thereof in an aqueous buffer solution at pH 4 to 6.5 and, if desired, adding another active substance, e.g. an anti-inflammatory agent and/or a polymeric binder, e.g. polyvinylpyrrolidone and/or a preservative. The concentration of the active substance ranges from about 0.1 to about 1.5 mg, preferably 0.25 to 1.0 mg, in 10 ml of a solution or 10 g of a gel.

An oily preparation for topical application is obtained, for example, by suspending the active substance according to the invention or a therapeutically acceptable salt thereof in an oil, optionally with the addition of swelling agents, such as aluminium stearate, and/or surface active agents (surfactants), with an HLB value (hydrophilic lipophilic balance) of below 10, such as fatty acid monoesters of polyhydric alcohols, e.g. glycerine monostearate, sorbitan monolaurate, sorbitan monostearate or sorbitan monooleate. A greasy ointment is obtained, for example, by suspending the active substances according to the invention or the salts thereof in a spreadable grease base, optionally with the addition of a surfactant having an HLB value of less than 10. An emulsified ointment is obtained by triturating an aqueous solution of the substances according to the invention or the salts thereof in a soft, spreadable, grease base with the addition of a surfactant with an HLB value of less than 10. All these topical preparations may also contain preservatives. The concentration of the active substance is from 0.1 to 1.5 mg, preferably 0.25 to 1.0 mg, in about 10 g of the basic composition.

In addition to the pharmaceutical compositions described above and their analogues which are intended for direct medical use in the body of humans or mammals, the present invention also relates to pharmaceutical compositions and preparations for medical use outside the living body of the human or mammal. Compositions and preparations of this kind are used primarily as anticoagulant additives to blood which is subjected to circulation or treatment, e.g. extracorporeal circulation or dialysis in artificial kidneys), preservation or modification (e.g. hemoseparation) outside the body. These preparations, such as storage solutions or preparations in the form of dosage units, are similar in composition to the injectable preparations described above; however, the quantity or concentration of the active substance is conveniently related to the volume of blood which is to be treated. Depending on the specific purpose, a suitable dosage range is from about 0.01 to about 1.0 mg of active substance per liter of blood, although the upper limit may be exceeded without any danger.

In particular, the invention relates to the DNA molecules coding for VAC proteins as described in the examples, expression plasmids containing such DNA molecules, microorganisms transformed with such expression plasmids, monoclonal antibodies against VAC, hybridoma cells which produce such antibodies, and test kits for immunoassays which contain such antibodies, the processes for preparing them described in the examples and the processes described in the examples for preparing proteins/polypeptides with VAC activity by means of the transformed microorganisms, and the new VAC compounds described in the examples.

When the present application refers to vascular anticoagulant proteins or VAC protein for short, this means that, unless otherwise stated, it is referring to polypeptides/proteins which essentially have the properties native to the proteins described for the first time in EPA 181465. These properties can be detected and checked by the methods of testing and characterization described therein (VAC activity).

This definition also includes the polypeptides/proteins which constitute aggregations such as for example dimers, trimers or tetramers, even if they have no or only limited biological activity per se in the aggregated form, provided that they can be converted in vivo or in vitro into at least one active component.

If, within the scope of the present invention, polypeptides/proteins are obtained which have no or only limited biological activity per se, for example fusion proteins or so called "pro-drugs", polypeptides/proteins which can be converted into the active components by a manner known to those skilled in the art, for example by processing in vitro or in vivo, or polypeptides/proteins which only develop their activity in vivo, these are also covered by the definition of vascular anticoagulant proteins, VAC proteins for short, and are thus part of the object of this invention.

The phrase "compounds with VAC activity" also refers to those polypeptides expressed by the above-mentioned transformed host cells which show a VAC activity and a positive reaction with anti-VAC antibodies and which have the primary structure of VAC or a structure derived therefrom. VAC compounds with a structure derived from the primary structure of VAC are those modified VAC compounds in which the modification consists of a shortening of the primary structure of the VAC, a rearrangement of the repeat structure or a modification which results in a change in the stability or activity.

In the present invention, the term "VAC-DNA/gene" refers to the DNA molecules which code for the VAC proteins defined hereinbefore.

The following Examples and drawings serve to illustrate the invention and are not intended to restrict it in any way.

To simplify the following Examples, any methods which recur frequently are described in abbreviated form.

Plasmids are written with a small "p", followed by capital letters and numbers. Starting plasmids are commercially obtainable or publicly available without restriction. They may also be constructed from such plasmids using published methods.

The "cutting" or "digestion" of DNA refers to the catalytic cleavage of the DNA by means of restriction endonucleases (restriction enzymes) at specific sites for this purpose, known as restriction sites. Restriction endonucleases are commercially available and are used under the conditions recommended by the manufacturers (buffer, bovine serum albumin (BSA) as carrier protein, dithiothreitol (DTT) as antioxidant).

Restriction endonucleases are written with a capital letter, usually followed by small letters and normally a Roman numeral. The letters depend on the microorganism from which the restriction endonuclease in question was isolated (for example: SmaI: *Serratia marcescens*). Usually, approximately 1 ug of DNA is cut with one or more units of the enzyme in about 20 ul of buffer solution. Normally, an incubation period of 1 hour at 37° C. is used, but may vary depending on the instructions for use provided by the manufacturer. After the cutting, the 5' phosphate group is sometimes removed by incubation with alkaline phosphatase from calves' intestines (CIP). This serves to prevent undesired reactions of the specific site in a subsequent ligase reaction (e.g. circularization of a linearized plasmid without insertion of a second DNA fragment). Unless otherwise stated, DNA fragments are normally not dephosphorylated after cutting restriction endonucleases. The reaction conditions for incubation with alkaline phosphatase may be found, for example, in the M13 Cloning and Sequencing Handbook (Cloning and Sequencing Handbook published by Amersham, PI/129/83/12). After incubation, protein is eliminated by extraction with phenol and chloroform and the DNA is precipitated from the aqueous phase by the addition of ethanol.

"Isolation" of a specific DNA fragment indicates that the cut DNA is separated on a 1% agarose gel, for example. After electrophoresis and making the DNA visible in UV light by staining with ethidium bromide (EtBr), the desired fragment is located by means of molecular weight markers which have been applied and bound to DE 81 paper (Schleicher and Schüll) by further electrophoresis. The DNA is washed by rinsing with low salt buffer (200 mM NaCl, 20 mM tris pH=7.5, 1 mM EDTA) and then eluted with a high salt buffer (1M NaCl, 20 mM Tris pH=7.5, 1 mM EDTA). The DNA is precipitated by the addition of ethanol. "Southern Analysis" is the method by which the presence of a specific DNA fragment in a DNA mixture is demonstrated by hybridization with a known, labelled oligonucleotide probe or a labelled DNA fragment. Unless otherwise specified, Southern Analysis hereinafter means the separation of the DNA mixture on a 1% agarose gel, denaturing and transfer to nitrocellulose filters (Schleicher and Sch üll), BA 85) using the method of E. Southern, J. Mol. Biol. 98 (1978), pages 503–517, and hybridization as described in R. Hauptmann et al., Nucleic Acids Res. 13 (1985), pages 4739–4749.

"Transformation" refers to the introduction of DNA into an organism so that the DNA can be replicated therein, either extra-chromosomally or as a chromosomal integrant. Transformation of *E. coli* follows the method specified in the M13 Cloning and Sequencing Handbook (Cloning and Sequencing Handbook published by Amersham, PI/129/83/12).

"Sequencing" of a DNA indicates the analysis of the nucleotide sequence in a DNA. To do this, the DNA is cut with various restriction enzymes and the fragments are introduced into correspondingly cut M13 mp8, mp9, mp18 or mp19 double-stranded DNA, or the DNA is introduced by ultrasound, subsequent repair of the ends and size selection into SmaI cut, dephosphorylated M13 mp8 DNA (by the shotgun method). After the transformation of *E. coli* JM101, single stranded DNA is isolated from recombinant M13 phages in accordance with the M13 Cloning and Sequencing manual (Cloning and Sequencing Handbook published by Amersham, PI/129/83/12) and sequenced by Sanger's dideoxy method (F. Sanger et al., Proc. Natl. Acad. Sci. 74 (1977), pp. 5463–5467). The evaluation of the sequences is carried out using the computer programs originally developed by R. Staden (R. Staden, Nucleic Acids Res. 10 (1982), pp.4731–4751) and modified by Ch. Pieler (C. Pieler 1987, Dissertation, University of Vienna).

"Ligation" relates to the process of forming phosphodiester bonds between two ends of double stranded DNA fragments. Usually, between 0.02 and 0.2 ug DNA fragments in 10 ul are ligated with about 5 units of T4-DNA ligase ("ligase") in a suitable buffer solution (T. Maniatis et al., Molecular Cloning, 1982, page 474).

"Preparation" of DNA from transformants means the isolation of the plasmid DNA from bacteria using the alkaline SDS method modified according to Birnboim and Doly (T. Maniatis et al., Molecular cloning, 1982, pp. 368–369) omitting the lysozyme. The bacteria from a 1.5 to 50 ml culture are used.

"Oligonucleotides" are short polydeoxynucleotides which are synthesised chemically. The Applied Biosystems Synthesizer Model 381A was used for this. The oligonucleotides are worked up in accordance with the model 381A User Manual (Applied Biosystems) and purified by polyacrylamide gel electrophoresis (PAGE).

"Phosphorylation" means the enzymatic transfer of the gamma-phosphate group from ATP to a free 5'OH group of a nucleic acid, usually an oligonucleotide. In 10 ul of solution, up to 100 pMol of the oligonucleotide are phosphorylated with 10 units of T4 polynucleotide kinase in the presence of 100 pMol of ATP in suitable buffer solution (70 mM Tris, pH=7.6, 10 mM MgCl$_2$, 5 mM DTT) for 30 minutes at 37° C. The reaction is usually stopped by heating to 100° C. for 10 minutes.

Some of the abbreviations used will now be defined:

| | |
|---|---|
| bp: | base pairs |
| BSA: | bovine serum albumin |
| DTT: | dithiothreitol |
| EDTA: | ethylenedinitrilotetraacetic acid, disodium salt |
| SDS: | sodium dodecylsulphate |
| Tris: | Tris(hydroxymethyl)-aminomethane |
| Denhardt: | 0.02% Ficoll, 0.02% polyvinylpyrrolidone, 0.02% BSA |
| LB: | 10 g/l tryptone, 5 g/l yeast extract, 5 g/l NaCl |
| 1× SSC: | 150 mM NaCl, 15 mM tri-sodium citrate, pH = 7 |
| TE: | 10 mM Tris pH = 8.0, 1 mM EDTA |

List of Figures:

| | |
|---|---|
| 0.1: | Tryptic fragments from placenta VAC |
| 0.2: | HPLC of the tryptic peptides from placenta-VAC |
| 0.3: | HPLC of the tryptic peptides from umbilical cord VAC |
| 0.4: | Gel permeation HPLC of placenta and umbilical cord VAC |
| 0.5: | Reverse phase HPLC of placenta-VAC |
| 0.6: | SDS gel electrophoresis of placenta VAC |
| 1: | Screening oligonucleotide EBI-386, 387 and 388 |
| 2: | Screening oligonucleotides EBI-118 and 119 |
| 3: | Northern blot analysis with VAC-alpha and VAC-beta cDNA |
| 4A–4C: | VAC-alpha cDNA sequence |
| 5A–5B: | Arrangement of the peptide sequences in the VAC-alpha cDNA derived amino acid sequence |
| 6: | Subsequence repeated four times in VAC-alpha protein |
| 7A–7C: | VAC-beta cDNA sequence |
| 8: | Subsequence repeated four times in VAC-beta protein |
| 9: | Amino acid composition of VAC-alpha and VAC-beta |
| 10: | Genomic Southern blot analysis with VAC-alpha and VAC-beta cDNA |
| 11: | Amino acid comparison of VAC-alpha with VAC-beta |
| 12A–12B: | Nucleotide comparison between VAC-alpha and beta cDNA |
| 13A–13B: | Hydrophilicity plot of VAC-alpha and VAC-beta |
| 14: | Comparison of VAC-alpha, VAC-beta, lipocortin I and lipocortin II |

| | |
|---|---|
| 15: | Sequence of the promoter and terminator section in pRH284 |
| 16: | Construction of pRH291 |
| 17: | Construction of pRH212 |
| 18: | Construction of pRH292 |
| 19: | SDS gel electrophoresis of the expressed proteins<br>a) Coomassie Blue stained protein gel<br>b) Western blot<br>Legend: M = molecular weight marker<br>+phosphate = inhibition of VAC expression<br>−phosphate = VAC expression (pho promoter induced) |
| 20: | Purification of VAC-alpha; Coomassie Blue stained SDS gel electrophoresis gel<br>Bands: |
| | 1: Crude extract<br>2: Ammonium sulphate pellets (dissolved and dialysed) 12: 5 ug of DEAE-FF Sepharose fractions 1–11<br>3: VAC pool after DEAE-FF Sepharose chromatography<br>4: VAC pool after Sephacryl-S 200 HR chromatography<br>5: Purified VAC after Q-Sepharose-FF chromatography<br>6: Purified natural VAC from human placenta<br>7: Molecular weight marker (Pharmacia; 94 kD, 67 kD, 43 kD, 30 kD, 20 kD and 14 kD) |
| 21: | Sephacryl S-200 HR chromatography of pre-purified r-VAC-α |
| 22: | Q-Sepharose-FF chromatography of pre-purified r-VAC-α |
| 23: | Gel permeation HPLC of natural VAC |
| 24: | Gel permeation HPLC of recombinant VAC-α |
| 25: | Reverse phase HPLC of natural VAC |
| 26: | Reverse phase HPLC of recombinant VAC-α |
| 27: | HPLC of the tryptic fragments from natural VAC |
| 28: | HPLC of the tryptic fragments from recombinant VAC-α |
| 29: | SDS gel from a comparison between natural and recombinant VAC-α in the presence or absence of DTT |
| 30: | SDS gel from recombinant VAC-α in the presence or absence of DTT |
| 31: | Western Blot analysis of natural VAC and recombinant VAC-α |
| 32: | Isoelectric focussing of natural VAC and recombinant VAC-α |
| 33: | Modified prothrombin time test with natural and recombinant VAC |
| 34: | Thrombin time test with natural and recombinant VAC |
| 35: | Factor Xa formation in plasma by natural and recombinant VAC |
| 36: | Binding of VAC to phospholipid double layers |

List of Figures:
0.1: Tryptic fragments from placenta VAC
0.2: HPLC of the tryptic peptides from placenta-VAC
0.3: HPLC of the tryptic peptides from umbilical cord VAC
0.4: Gel permeation HPLC of placenta and umbilical cord VAC
0.5: Reverse phase HPLC of placenta-VAC
0.6: SDS gel electrophoresis of placenta VAC
1: Screening oligonucleotide EBI-386, 387 and 388
2: Screening oligonucleotides EBI-118 and 119
3: Northern blot analysis with VAC-alpha and VAC-beta cDNA
4A–4C: VAC-alpha cDNA sequence
5A–5B: Arrangement of the peptide sequences in the VAC-alpha cDNA derived amino acid sequence
6: Subsequence repeated four times in VAC-alpha protein
7A–7C: VAC-beta cDNA sequence
8: Subsequence repeated four times in VAC-beta protein
9: Amino acid composition of VAC-alpha and VAC-beta
10: Genomic Southern blot analysis with VAC-alpha and VAC-beta cDNA
11: Amino acid comparison of VAC-alpha with VAC-beta
12A–12B: Nucleotide comparison between VAC-alpha and beta cDNA
13A–13B: Hydrophilicity plot of VAC-alpha and VAC-beta
14: Comparison of VAC-alpha, VAC-beta, lipocortin I and lipocortin II
15: Sequence of the promoter and terminator section in pRH284
16: Construction of pRH291
17: Construction of pRH212
18: Construction of pRH292
19: SDS gel electrophoresis of the expressed proteins
  a) Coomassie Blue stained protein gel
  b) Western blot
  Legend: M=molecular weight marker
  +phosphate=inhibition of VAC expression
  −phosphate=VAC expression (pho promoter induced)
20: Purification of VAC-alpha; Coomassie Blue stained SDS gel electrophoresis gel
  Bands:
  1: Crude extract
  2: Ammonium sulphate pellets (dissolved and dialysed) 12: 5 ug of DEAE-FF Sepharose fractions 1–11
  3: VAC pool after DEAE-FF Sepharose chromatography
  4: VAC pool after Sephacryl-S 200 HR chromatography
  5: Purified VAC after Q-Sepharose-FF chromatography
  6: Purified natural VAC from human placenta
  7: Molecular weight marker (Pharmacia; 94 kD, 67 kD, 43 kD, 30 kD, 20 kD and 14 kD)
21: Sephacryl S-200 HR chromatography of prepurified r-VAC-α
22: Q-Sepharose-FF chromatography of pre-purified r-VAC-α
23: Gel permeation HPLC of natural VAC
24: Gel permeation HPLC of recombinant VAC-α
25: Reverse phase HPLC of natural VAC
26: Reverse phase HPLC of recombinant VAC-α
27: HPLC of the tryptic fragments from natural VAC
28: HPLC of the tryptic fragments from recombinant VAC-α
29: SDS gel from a comparison between natural and recombinant VAC-α in the presence or absence of DTT
30: SDS gel from recombinant VAC-α in the presence or absence of DTT
31: Western Blot analysis of natural VAC and recombinant VAC-α
32: Isoelectric focussing of natural VAC and recombinant VAC-α
33: Modified prothrombin time test with natural and recombinant VAC
34: Thrombin time test with natural and recombinant VAC
35: Factor Xa formation in plasma by natural and recombinant VAC
36: Binding of VAC to phospholipid double layers
37: Construction of pGN25 and pGN26.
38: Purification of recombinant VAC-β; Coomassie Blue stained SDS gel electrophoresis gel.
39: Purification of recombinant VAC-β; in process samples.
40: Gel permeation HPLC of recombinant VAC-β.
41: Reverse phase HPLC of recombinant VAC-β.
42: Reverse phase HPLC of recombinant VAC-β after incubation.
43A–43B: Amino acid analysis of recombinant VAC-β.
44: N terminal sequencing of recombinant VAC-β.
45: SDS gel of recombinant VAC-β in the presence or absence of DTT.

46A–46B: Isoelectric focussing of recombinant VAC-β.

47: Effect of VAC α and VAC β on prothrombinase activity. Prothrombin activation was measured in the presence of varying amounts of VAC α (o) or VAC β (•) as described in the text.

48: Effect of VAC α on the phospholipase $A_2$ activity. Phospholipase $A_2$ activity was determined as described in the text. VAC α induced inhibition was measured at either 13.2 μM phospholipid (open circles) or 6.6 μM phospholipid (closed circles).

49: Effect of VAC β on the phospholipase $A_2$ activity. Determination of % inhibition is described in the text. Inhibition was measured at 13.2 μM (open circle) or 6.6 μM phospholipid (closed circles).

50: The effect of $Ca^{++}$ on the VAC α induced inhibition of phospholipase activity. Inhibition was measured at 6.6 μM phospholipid and 1 mM (open circles), 0.5 mM (closed circles), 0.1 mM (open squares) or 0.05 mM $Ca^{++}$ (closed squares).

51: The effect of $Ca^{++}$ on the VAC β induced inhibition of phospholipase activity. Inhibition was measured at 6.6 μM phospholipid and 1 mM (open circles), 0.5 mM (closed circles), 0.1 mM (open squares) or 0.05 mM $Ca^{++}$ (closed squares).

Example O

The material isolated from umbilical cord vessels and/or placenta and then purified was repurified by reverse phase HPLC.

| Stationary phase: | Bakerbond WP-RP 18, 4.6 × 250 mm, 5 um particles, 300 Å pores |
|---|---|
| Mobile phase A: | 0.1% trifluoroacetic acid in water, pH 2.2 |
| Mobile phase B: | 0.1% trifluoroacetic acid in acetonitrile |
| Gradient: | 20–68% B in 24 min. |
| Flux: | 1 ml/min |
| Detection: | UV, 214 nm |

After this purification step, both materials, both being substances with a molecular weight of 32,000, were digested with trypsin.

Reaction Conditions

| 30 ug of VAC from placenta were reacted in 135 ul of 0.15M $NH_4HCO_3$, pH 8.0 + 2% w/w trypsin (Worthington) for 6 hours at 37° C. + 2% w/w trypsin (Worthington) overnight at 37° C. |
|---|
| 30 ug of VAC from umbilical cord were reacted in 100 ul of 1% $NH_4HCO_3$, pH 8.0 + 2% w/w trypsin (Worthington) for 6 hours at 37° C. + 2% w/w trypsin (Worthington) overnight at 37° C. |

The fragments obtained were separated by HPLC and subjected to sequencing with a gas phase sequenator Type 470A made by Applied Biosystems, Program 02 RPTH.

HPLC Separation Conditions:

| Stationary phase: | μBondapak C18, 3.8 × 300 mm, 10 mm particles |
|---|---|
| Mobile phase A: | 0.1% trifluoroacetic acid in water, pH 2.2 |
| Mobile phase B: | 0.1% trifluoroacetic acid in acetonitrile |
| Gradient: | 0–55% B in 55 min |
| Flux: | 1 ml/min |
| Detection: | UV, 214 nm (upper trace) 280 nm (lower trace) |

In addition to tryptic digestion, the material purified by reverse phase HPLC was also subjected to BrCN cleavage. These cleavage peptides were also sequenced and compared with the data relating to the peptides from the tryptic digestion.

BrCN Cleavage:

111 ug of VAC purified by RP-HPLC were dissolved in 111 ul of 70% formic acid. This already contained a 250-fold molar excess of BrCN (90 mcg). Incubation was effected in the dark for 17 hours at ambient temperature. 100 ul were used for the HPLC separation.

| HPLC column: | μBondapak C18 |
|---|---|
| Mobile phase A: | 0.1% trifluoroacetic acid in water |
| Mobile phase B: | 0.1% trifluoroacetic acid in acetonitrile |
| Gradient: | 0–70% B in 70 min |
| Flux: | 1 ml/min |
| Detection: | UV, 214 and 280 nm |

Comparison of the results thus obtained and analysis by gel permeation HPLC and SDS gel electrophoresis proves that VAC from placenta and VAC from umbilical cord are identical.

Gel Permeation HPLC:

| Stationary phase: | Waters I-125, 7.8 × 600 mm, 10 um particles |
|---|---|
| Mobile phase: | 0.5M $Na_2SO_4$, 0.02M $Na_2PO_4$, pH 7.0, 25% propyleneglycol, 0.04% Tween 20 |
| Flux: | 0.5 ml/min |
| Detection: | UV, 214 nm |

SDS Gel Electrophoresis

| SDS gel: | 15% |
|---|---|
| Gel thickness: | 0.7 mm |
| Electrophoresis conditions: | 20 mA/plate, 2–3 hours' running time |
| Staining: | Coomassie Blue |
| Probes: | 8 ug of VAC from umbilical cord or 7 ug of VAC from placenta |

EXAMPLE 1

Preparation of a Human Placental cDNA Library a) Total RNA Isolation from Placenta GT: 5M guanidinium thiocyanate, 50 mM Tris pH=7.4, 25 mM EDTA. Before use 8% (v/v) of beta-mercaptomethanol are added. 20 ml of GT are cooled on ice for 5 to 10 minutes before use, the GT should not be precipitated during this time.

GH: 6M guanidiun hydrochloride, 25 mM EDTA, 10 mM beta-mercaptoethanol, pH=7.0. Cooling with ice 1 g of deep frozen and mechanically powdered placenta are mixed in 20 ml of GT (0° C.) for 20 seconds at maximum speed using a Polytron (Brinkmann). The volume of the homogenized mixture is determined, it is poured into 0.3 vol of ethanol (−20° C.), mixed and immediately centrifuged at 12,000 rpm 5' at −10° C. (Beckman JA 21 centrifuge, JS13.1 rotor). Any protein film and the supernatant are removed. 10 ml of ice cold GH are added to the pellet and homogenized for 10 seconds using the Polytron. The suspension is centrifuged for 5 minutes at −10° C. and at 12,000 rpm. The supernatant is transferred into a sterile Corex tube and the pellet is discarded. 0.025 vol of 1M acetic acid and 0.75 vol of cold ethanol (−20° C.) are added to the supernatant and mixed thoroughly. After about 2 hours' incubation at −20° C. the mixture is centrifuged for 10 minutes at 6000 rpm at −20° C. (JA20 Rotor). The protein film and supernatant are carefully removed. 2 ml of GH (0° C.) are added to the pellet, the pellet is resuspended and the suspension is transferred into a 15 ml Corex tube. The old Corex tube is rinsed out with another 8 ml of GH, and the solution is combined with the 2 ml. It is important that the entire pellet be suspended and if necessary it should be subjected to subsequent treatment by mild sonication. 0.025 vol of 1M acetic acid and 0.5 vol of cold ethanol (−70° C.) are added and incubated for about 2 hours at −20° C. Centrifugation (6000 rpm, 10 min, JA20 rotor), dissolving and precipitation are repeated twice, the total quantity of GH being halved to 5 ml. After the last centrifugation, no film of protein should be visible above the solution, otherwise this purification step must be repeated. The pellet is vortexed for 2 minutes with 5 ml of diethyl pyrocarbonate-treated water (0° C.). The clear solution is decanted, some more water is added to any pellet residues remaining and vortexing is continued until the solution is clear. By the addition of 0.1 vol of 3M Na-acetate (pH=5.8), 2.5 vol of ethanol and 1 hours incubation at −70° C. the RNA is centrifuged off for 10 minutes at 6000 rpm and at 4° C. Dissolving and precipitation are repeated once. Finally, the RNA is stored in ethanol at −20° C.

b) poly-A$^+$-RNA Isolation 0.5 mg of oligo dT cellulose (Collaborative Research, Type 3, binding capacity: 5 mg poly-A$^+$ RNA/g) are suspended in binding buffer (200 mM NaCl, 0.2% SDS, 10 mM Tris, pH=7.4, 1 mM EDTA). 1 ml of this suspension is packed into a column and washed successively with 10 ml of water, 10 ml of 0.1N NaOH, 10 ml of water and finally 10 ml of binding buffer. The total RNA is pelleted out of the alkaline solution by centrifuging (10 min., 6000 rpm, JA20 rotor). About 10 mg of RNA are dissolved in 4.5 ml of water. After the addition of 50 μl of 2% SDS, the solution is heated to 70° C. for 3 minutes and immediately cooled on ice. After the addition of 50 μl of 1M Tris (pH=7.4), 10 μl of 0.5M EDTA and 200 μl of 5M NaCl the solution is immediately added to the column. The solution dripping out of the column is poured back into the column. This procedure is repeated three times in all. The column is then washed with 30 ml of binding buffer. The bound RNA is eluted with 5 ml of 0.2% SDS. The column is washed with 10 ml of water, 10 ml of 0.1N NaOH and 10 ml of H$_2$O and equilibrated with 10 ml of binding buffer. The RNA solution is heated to 70° C. for another 3 minutes, rapidly cooled on ice, 50 μl of 1M Tris pH=7.4, 10 μl of 0.5M EDTA and 200 μl of 5M NaCl are added and the resulting solution is poured onto the column. The solution running through is poured back into the oligo-dT column three times in all. After washing, the RNA is eluted with 30 ml of 0.2% SDS.

By the addition of 0.1 vol of 3M Na-acetate pH=5.6 and 2.5 vol of ethanol and incubation at −20° C. (16 hours) the RNA is precipitated. It is centrifuged off (10,000 rpm, 15 min., JA-20 Rotor) and dissolved in water at a concentration of 1 μg/μl.

c) Construction of the lambda-qt10 cDNA library

Synthesis of the cDNA, methylation of the internal EcoRI sites, the application of EcoRI linkers, the recutting with EcoRI, the removal of the short DNA fragments, the ligation with the lambda-gt10 arms and the packaging of the ligated DNA in vitro were effected using the cDNA synthesis system made by Amersham (RPN 1256) and the cDNA cloning system lambda-gt10 (Amersham, RPN 1257). The operating procedures supplied with the systems were adhered to exactly. Starting from about 3 μg, approximately 0.5×10$^6$ recombinant lambda-gt10 phages were finally obtained from the mRNA.

EXAMPLE 2 cDNA isolation a) Searching through the lambda-qt10 library with oligonucleotides In order to search through the cDNA library for cDNA coding for VAC protein, two oligonucleotides were synthesized corresponding to the sequences of the tryptic peptide P16/II and one oligonucleotide was synthesized corresponding to the Staph A peptide P20/I/6 (FIG. 1). These oligonucleotides are all mixtures of all the variants which take into account every possibility of coding of the corresponding mRNA. EBI-386 has 512 variations with a chain length of 20 nucleotides and fits the Staph-A peptide P20/I/6. In order to minimize the variation in the oligonucleotide for the tryptic peptide P16/II, two oligonucleotides (20-mers) were synthesized: EBI-387: 128 variations, EBI-388: 64 variations.

Moreover, two oligonucleotides fitting the tryptic VAC peptide P30/I were synthesized using desoxyinosine as the base at "wobble" positions (FIG. 2): EBI-118 and EBI-119. This substitution has been described by E. Ohtsuka et al., J. Biol. Chem. 260/5 (1985), pp. 2605–2608, and Y. Takahashi et al., Proc. Nat. Acad. Sci. (1985) pp. 1931–1935. Inosine base-pairs well with cytosine, but still hardly disturbs the formation of the double helix if other nucleotides are presented as partners.

60 pMol of each oligonucleotide were phosphorylated with 60 pMol of gamma-$^{32}$P-ATP (Amersham, PB 218, 5000 Ci/mMol) in 30 μl of solution using 20 units of T$_4$ polynucleotide kinase. The solution contained 70 mM Tris pH 7.5, 10 mM MgCl$_2$ and 5 mM DTT and the incubation period was 30 minutes. The reaction was stopped by the addition of 30 mM EDTA and heating to 70° C. for 5 minutes. The labelled oligonucleotide was separated from any non-incorporated radioactivity by column chromatography using Biogel P6DG (Biorad). Between 70 and 110× 10$^6$ cpm of phosphorus-32 were incorporated for each oligonucleotide.

15 pMol each of EBI-118 and EBI-119 were phosphorylated in 90 μl with the addition of 45 pMol of gamma-$^{32}$P-ATP (Amersham, PB 218 5000 Ci/mMol) with 10 units of T$_4$ polynucleotide kinase and subsequently purified over Biogel P6DG. A total of 70×10$^6$ cpm of phosphorus-32 were incorporated.

Approximately 1.2×10$^6$ pfu (plaque forming units) recombinant phages of a human placental cDNA library in the phage lambda-gt10 were used to infect E. coli C600. About 50,000 phages were plated for each 13.5 cm Petri dish (LB, 10 mM MgSO$_4$, 15 g/l Bacto-Agar). When the plaques were virtually confluent, two extracts from each plate were prepared on nitrocellulose filters (Schleicher and Schüll, BA 85) (T. Maniatis et al., Molecular Cloning, 1982, pp 320–321). The filters were treated in TE at 100° C. for 3×20 minutes and then washed overnight at 65° C.: Wash solution: 50 mM Tris pH=8

1M NaCl
1 mM EDTA
0.1% SDS

The filters were then prehybridized for 4 hours at 49° C.:
Prehybridizing solution:
6 x SSC
5 x Denhardt
0.1% SDS
1 mM Na-pyrophosphate
50 mM NaH$_2$PO$_4$ pH=6.5
100 mcM ATP
80 mcg/ml of denatured herring sperm DNA Hybridization was carried out in the same solution using the entire quantity of labelled oligonucleotides. The doubled extracts from plates 1 to 6 were hybridized with EBI-386, those from plates 7 to 12 were hybridized with EBI-387 and EBI-388 for 16 hours at 49° C. The extracts from plates 13 to 24 were hybridised for 16 hours at 37° C. with EBI-118 and EBI-119. After hybridization had been carried out, the filters were rinsed twice with 6x SSC/0.01% SDS, and washed 2×30 minutes at ambient temperature with 6x SSC/0.01% SDS and 3×20 minutes in the same solution at 49° C. and 37° C., respectively. After drying in air, the filters were exposed on Kodak X-Omat S film at −70° C. using intensifier film.

Lambda phages which showed hybridization with the oligonucleotide on both filters were purified for homogeneity using the same hybridization procedure.

The hybridization with EBI-386, 387 and 388 resulted in the phages lambda P11/3, lambda P6/5 and lambda P6/6. Hybridization with EBI-118 and 119 resulted in the phages lambda-Nr15, lambda-Nr19 and lambda-Nr22.

b) Isolation of the cDNA insert

*E. coli* C 600 was infected with 2.5×10$^6$ pfu (plaque forming units) of phages and plated with 6 ml of top agarose (0.7% agarose, 10 mM MgSO$_4$, LB) on 13.5 cm agar dishes (LB, 10 mM MgSO$_4$, 1.5% agarose, 0.2% glucose). After 5½ hours' incubation at 37° C. the plaques were confluent. The plates were cooled for 30 minutes at 4° C. and the agarose was covered with 10 ml of lambda diluent (10 mM Tris, pH=8, 10 mM MgSO$_4$, 0.1 mM EDTA). The phages were eluted overnight at 4° C. with gentle shaking. The supernatant phage suspension (about 8 ml) was transferred to Corex tubes and centrifuged for 10 minutes at 15,000 rpm (4° C., JA 21 centrifuge). The supernatant was decanted into polycarbonate tubes and centrifuged at 50,000 rpm (20° C., L70 Beckman centrifuge, 20° C., 50 Ti Rotor) until omega$^2$t=3×10$^{10}$ (about 23 minutes). The pelleted phages were resuspended in 0.5 ml of lambda diluent after removal of the supernatant and then transferred into Eppendorf test tubes. The suspension was freed from any unsuspended particles by brief centrifuging and the supernatant was placed in a fresh test tube. After the addition of 10 μg/ml of RNaseA and 1 μg/ml of DNase I the mixture was incubated for 30 minutes at 37° C. After the addition of 25 mM EDTA, 25 mM Tris, pH=8, 0.2% SDS, the mixture was incubated for 30 minutes at 70° C. Next, 1 vol of phenol/chloroform (1:1) was added, and proteins were extracted by tilting the test tube. After 2 minutes' centrifugation in the Eppendorf centrifuge the aqueous phase was extracted with 1 vol of chloroform (only by tilting, not by vortexing). After phase separation by centrifugation, 1/20 vol of 3M Na-acetate and 1 ml of ethanol were added to the supernatant. The DNA phages were thus precipitated in the form of filaments. After 5 minutes' incubation at 0° C. the DNA was removed by centrifuging (10 minutes). The pellet was washed once with 70% ethanol, dried and dissolved overnight in 50 μl of TE (4° C.). The DNAs were cut with EcoRI and the resulting fragments were separated on a 1% agarose gel. The cDNA inserts of the clones lambda-P11/3, lambda-P6/5 and lambda-P6/6 ranged from about 1300 to 1400 bp in size. Sequence analysis showed all three clones were derived from one and the same mRNA. However, the 5' end of the mRNA was missing from the cDNAs. The inserts of the phages lambda-Nr15, lambda-Nr19 and lambda-Nr22 had lengths of about 1600, 1100 and 1000 bp. Sequence analysis indicated an approximately complete cDNA. The cDNAs of the two phage groups lambda-P11/3, lambda-P6/5 and lambda-P6/6 and lambda-Nr15, lambda-Nr19 and lambda-Nr22 are derived from two different mRNAs, as indicated by the following sequence analysis.

The EcoRI inserts of the three clones lambda-P11/3, lambda-P6/5 and lambda-P6/6 were isolated and ligated into the EcoRI-cut Bluescribe M13$^+$ vector (Vector Cloning Systems, 3770 Tansy Street, San Diego, Calif. 92121, USA). The resulting clones were designated pP6/5, pP6/6 and pP11/3.

The EcoRI inserts of the three clones lambda-Nr15, lambda-Nr19 and lambda-Nr22 were isolated and ligated into the EcoRI-cut Bluescribe M13$^+$ vector. The resulting clones were designated pRH201, pRH202 and pRH203.

c) Other VAC cDNA clones

In order to obtain other cDNA clones, the human placental lambda-gt10 library was searched once again, this time using the EcoRI insert of pP11/3 as the probe.

This DNA fragment was radioactively labelled by nick translation (T. Maniatis, Molecular Cloning, 1982, pages 109–112, no DNase I used). In all, 4×10$^5$ phages on 8 plates were investigated. The treatment of the nitrocellulose filters was carried out as described in T. Maniatis, Molecular Cloning, 1982, pages 320–321. The hybridization solution contained 6xSSC, 5xDenhardt's, 0.1% SDS and 20×10$^6$ cpm pP11/3 insert. Hybridization lasted for 16 hours at 65° C. The filters were then washed 3×10 minutes at ambient temperature with 6xSSC/0.01% SDS and 3×45 minutes at 65° C. with 0.2xSSC. In all, 69 positively reacting clones were obtained (lambda-VAC1 to lambda-VAC69).

12 of these clones were prepared on a small scale as described above, the cDNA inserts with EcoRI were freed and separated on a 1% agarose gel. It became apparent that the insert of the clone lambda-VAC10 contains the entire reading frame coding for VAC protein.

EXAMPLE 3

Characterization of the cDNAs coding for VAC-alpha and VAC-beta a) Northern blot experiment 5 μl of water, 16 μl of formamide, 6 μl of formaldehyde and 3 μl of 0.1M NaOH were added to 2 μg of poly-A$^{30}$ RNA, the solution was incubated for 10 minutes at 68° C. and then cooled on ice. After the addition of 5 μl of dye solution (0.4% each of bromophenol blue and xylene cyanol in 50% glycerol, 1 mM EDTA) the RNA was separated on a formamide agarose gel (1.5% agarose, 10 mM Na-phosphate pH=7.6, 1 mM EDTA, 5 mM Na-acetate, 6% formaldehyde, electrophoresis 100 V, 3 hours, eluting buffer as gel buffer, without formaldehyde). Total RNA was applied as a reference substance. This trace was taken off after electrophoresis and stained with EtBr in order to determine the position of the 28 and 18 S rRNA. The remainder of the gel was washed twice for 10 minutes in 10xSSC and the RNA was transferred to nitrocellulose filters with 10xSSC. The filter was washed with 2xSSC, dried and baked for 2 hours in vacuo at 80° C. 1 μg each of pP11/3 and pRH203 were radioactively labelled with the multiprime DNA labelling system (Amersham, RPN 1601). The nitrocellulose filter was prehybridized for 2 hours at 65° C. in 6xSSC/5x Denhark's/0.1% (d SDS. One trace was hybridised with 180×10$^6$ cpm pP11/3 or pRH203 (16 hours at 65° C.). The filters were washed twice, for 30 minutes at ambient temperature, with 6xSSC/0.01% SDS and twice for 30 minutes at 65° C. with 0.2xSSC/0.01% SDS, dried and exposed on Kodak X-Omat S film with intensifier film.

The results are shown in FIG. 3. The cDNA of the clone pP11/3 hybridizes to an mRNA about 1700 bases long ("VAC-alpha"), whilst the cDNA of the clone pRH 203 hybridizes to an mRNA about 2200 bases long ("VAC-beta").

Since, firstly, the quantity of radioactivity used and the amount of mRNA applied per trace were approximately the same and secondly the hybridization of a genome blot in the same solution produced bands of equal intensity with both cDNAs (see below), it can be concluded that the shorter mRNA ("VAC-alpha") is present in placenta in larger quantities than the longer ("VAC-beta") mRNA.

b) Sequence analysis of the VAC-alpha cDNA

The cDNA of clones pP6/5, pP6/6 and pP11/3 were totally sequenced and those of the clones lambda-VAC1 to 12 were partially sequenced. The results are shown in FIG. 4. In all, 1465 bases were sequenced. The cDNA has a long open reading frame which can code for 320 amino acids. If the DNA sequence is translated into an amino acid sequence, all the sequenced peptides can be accommodated in this sequence (FIG. 5). Therefore, this cDNA is the one whose corresponding mRNA codes for VAC protein. Since the sequences of the second isolated cDNA (see below) code for a protein which is similar, but different from VAC, the name VAC-alpha is introduced here.

The first ATG codon (bases 35–37) is preceded by a stop codon in the same reading frame. Bases 30 to 38 satisfy the Kozak rule fairly well (M. Kozak, Nature 308 (1984) pages 241–246), which gives the consensus sequence near the translation start codon as CC(A/G)CCAUGG; the corresponding sequence here is TCGCTATGG. The 3' untranslated region is 471 bases long. 15 bases before the start of the poly-A section is the polyadenylation sequence AATAAA (N. J. Proudfoot et al., Nature 263 (1976), pp 211–214). If the poly-A section of the mRNA is reckoned to have chain lengths of 150 to 200 bases, the total length of the mRNA, based on the cDNA sequence, will be 1600–1650. Since a higher value was determined in the Northern blot experiment, the 5' untranslated region does not appear in complete form in any cDNA.

Unlike all the other cDNA clones, the cDNA of clone pP6/5 has C instead of A at position 100. Consequently, the triplet 98–100 (22nd codon) would change from GAA to GAC and would code for Asp instead of Glu. This deviation may have causes: a) the reverse transcriptase has incorporated a wrong nucleotide, b) they are the transcripts of two allelic genes which differ at this point or c) there are two non-allelic genes which differ at this position.

The long open reading frame codes for a protein with 320 amino acids, of which the Met-1 will probably be cleaved and the following alanine will be blocked at the amino group, possibly by acylation. The calculated molecular weight is 35,896 D and is greater than the weight according to SDS-PAGE. Certainly, the proportion of charged amino acids (Asp, Glu, Lys, Arg, His) at 30.6% (98/320) is well above average compared with the average value of 25.1%. This would explain the different migration behaviour of the protein in the SDS-PAGE. Among the strongly charged amino acids, the acidic amino acids (Asp and Glu) are predominant, being 54 in number as against the basic amino acids (Lys and Arg) of which there are 41. This explains the acidic isoelectric point of the VAC-alpha protein (pI=4.4 to 4.8). VAC-alpha contains only one triplet coding for cysteine (amino acid position 316); no typical N-glycosylation site (Asn-XXX-Ser/Thr) is present. Structural analysis of the amino acid sequence (modified according to Pustell, J. et al., Nucleic Acids Res. 10 (1982) pp 4765–4782) shows a fourfold repetition of a sequence 67 amino acids long (FIG. 6), hereinafter referred to as "repeats". Within this sequence, 7 amino acids (10.4%) are preserved in all four repeats, 15 amino acids (22.4%) occur in three of the four repeats and at 28 positions (41.8%) two repeats contain the same amino acid.

A comparison with published data (M. J. Geisow, FEBS Letters 203 (1986), pp. 99–103, M. J. Geisow et al., TIBS 11 (1986), pp. 420–423) surprisingly showed that VAC-alpha therefore belongs to a fairly large group of Ca$^{++}$ dependent phospholipid binding proteins. A consensus sequence is described (Lys-Gly-fob-Gly-Thr-Asp-Glu-var-var-Leu-Ile-fil-Ile-Leu-Ala-fob-Arg; fob=hydrophobic, fil=hydrophilic, var=variable), which could have been involved in the Ca$^{++}$ binding (M. J. Geisow et al., Nature 320 (1986), pp. 636–638). This sequence occurs in each of the four repeated 67 amino acid long subsequences of the proteins according to the invention (FIG. 6). The 6 amino acid long section at the end of each repeat which consists almost exclusively of hydrophobic amino acids is also noticeable ("oooooo" in FIG. 6).

c) Sequence analysis of the VAC-beta cDNA

The VAC-beta cDNA sequence of clones Nr15, Nr19 and Nr22 yielded 1940 bp and merges into a poly-A section (FIG. 7). 16 bases before the poly-A section is the polyadenylation signal AATAAA. Certainly, this consensus sequence occurs at nucleotide position 1704–1709. It is not known why this sequence is not used as a polyadenylation signal. The sequence additionally required at the 3' end of the AATAAA sequence, namely YGTGTTYY (Gill A. et al., Nature 312 (1984), pp. 473–474) only occurs a relatively long way on (TGTGTTAT, position 1735–1742); it is possible that this is the explanation for nonacceptance of the first polyadenylation sequence.

The cDNA contains a long open reading frame which extends from the start of the cDNA to position 1087. It would contain a coding potential for 362 amino acids. For reasons of analogy with VAC-alpha and owing to the fact that a 34,000 D protein also occurs in the purification of VAC (see EPA 181465) the first methionine codon (ATG, positions 107–109) was taken as the start of translation. The Kozak rule is not so well satisfied here as in the case of VAC-alpha (AAGAGATGG at position 102–110).

The resulting protein (VAC-beta) would be 327 amino acids long. It has 4 cysteine groups (amino acid position 161, 206, 250 and 293) and a potential N-glycosylation site (Asn-Lys-Ser, amino acid position 225–227). The calculated molecular weight is 36,837 (FIG. 9). In VAC-beta, too, there is a larger than average number of charged groups: 97/327 (29.6%), whilst the acidic amino acids (Asp+Glu: 49) predominate over the basic amino acids (Lys+Arg 42); this would explain the lower molecular weight detected by SDS-PAGE.

VAC-beta also shows an internal repetition of a 67 amino acid long sequence (FIG. 8). Within this sequence, 7 amino acids (10.4%) are preserved in all four repeats, 17 amino acids (25.4%) occur in three of the four repeats, and at 25 positions (37.7%) two repeats contained the same amino acid. VAC-beta also shows high similarity with the 17 amino acid long consensus sequence. The remarks made regarding VAC-alpha also apply to VAC-beta.

d) Genomic Southern blot analysis

The analysis of chromosomal DNA from human placenta according to Southern shows a complex picture. The DNA has been cut with EcoRI, HindIII, BamHI and PstI. The DNA transferred to nitrocellulose was hybridized both with a VAC-alpha DNA (pP11/3) and also with a VAC-beta DNA (pRH203). The filters were washed under stringent conditions (see point a)), i.e. with 0.2xSSC and 65° C. Nevertheless, a relatively large number of bands appeared on each digestion (FIG. 10). Comparison of the two blots showed that the cross reaction of VAC-alpha and beta DNA can probably be ruled out under these conditions. The multiplicity of bands can be explained either by the existence of genes which are similar to the VAC-alpha or VAC-beta gene or it may be a gene which is interrupted by a large number of and/or long introns.

EXAMPLE 4

Protein analysis

FIG. 11 shows a comparison of the amino acid sequences of VAC-alpha and VAC-beta. The repeated structures can be arranged identically in both proteins. The connecting peptides are also of the same length with the exception of those between the second and third repeats. In VAC-alpha, a gap must be inserted into this connecting peptide in order to permit optimum matching of the two sequences. The N-terminal peptide of the two proteins is of different lengths, 19 amino acids in the case of VAC-alpha and 25 amino acids in VAC-beta. This peptide also has the lowest homology. The two proteins are identical at 176 of 320 amino acid positions, corresponding to a degree of homology of 55.0%.

At this point, a comparison of the nucleotide sequences of VAC-alpha and beta cDNAs should also be inserted. If two genes and their products are compared with each other, greater homology is seen on the DNA (=RNA) plane than on the amino acid plane, which is explained by the fact that, in the nucleic acid, a change in a base triplet is sufficient to encode a new amino acid.

FIG. 12 shows a comparison of the coding regions of VAC-alpha and VAC-beta cDNA. Surprisingly, the DNAs show a degree of homology of only 54.2%, i.e. rather less than the two proteins.

FIG. 13 shows the hydrophilicity profiles of the two proteins. The algorithm of Hopp and Wood was used (T. P. Hopp et al., Proc.Natl.Acad.Sci. 78 (1981) pp. 3824–3828). The four repeat areas are indicated by the bars and the connecting peptides in the sequence below are shown in a frame. It is noticeable that the connecting peptide between the second and third repeats is particularly hydrophilic. In this peptide, both in VAC-alpha and VAC-beta, there is an arginine in the same position. It would therefore be possible for this arginine to be a preferred point of attack for a protease with trypsin-like specificity. The molecule would have to break into two halves of substantially equal size. It would be possible for a "half molecule" of this kind to develop a biological activity, for example an anticoagulant activity. On the other hand, replacement of this arginine by for example histidine might give the VAC-proteins greater stability.

FIG. 13 also clearly shows that neither VAC-alpha nor VAC-beta has a fairly long hydrophobic region which would enable either secretion through a membrane or storage of the proteins in a membrane. It can therefore be assumed that VAC-alpha and VAC-beta are intracellular proteins.

Wallner et al. (Nature 320 (1986), pp.77–81) report the structure of human lipocortin I, Saris et al. (Cell 46 (1986), pp.201–212) and Huang et al. (Cell 46 (1986), pp. 191–199) report the structure of murine or human calpactin I, which is also known as lipocortin II. These proteins also belong to the category of the $Ca^{++}$ dependent phospholipid binding proteins. Their structure can be written down analogously to VAC-alpha and beta (FIG. 14). The homologies between VAC-alpha and VAC-beta are more marked than those between VAC and lipocortin:

VAC-alpha—VAC-beta: 55.0%
VAC-alpha—lipocortin I: 41.9%
VAC-alpha—lipocortin II: 43.8%
VAC-beta—lipocorin I: 41.7%
VAC-beta—lipocortin II: 44.6%

It can therefore be assumed that the lipocortins also have an anticoagulant activity, in view of their analogous structure, and consequently may be used as anticoagulants and furthermore that this is a general property of this class of $Ca^{++}$ dependent phospholipid binding proteins.

Many of the $Ca^{++}$ dependent phospholipid dependent proteins bind to purified secretory vesicles or other components of the cytoskeleton (see R. H. Kretsinger et al., Nature 320 (1986), page 573 for a summary). During secretion, the vesicles become detached from the Golgi apparatus of the cell, migrate to the cell membrane and fuse with it. The contents of the vesicles are thus freed from the cell. Analogously to the coupling of stimulation with muscle contraction, it has been proposed (W. W. Douglas, Br.J.Pharmac. 34 (1968), 451) that the stimulus and secretion are also coupled via $Ca^{++}$. The $Ca^{++}$ dependent phospholipid binding proteins could play an important part. In the conserved, 17 amino acid long region of each repeat, VAC-alpha has 5 to 6 amino acids which contain hydroxyl groups (Asp, Glu, Thr, Ser), three of them at identical positions. In VAC-beta, four of these amino acids occur in each repeat. Although none of the proteins has the EF hand structure observed in calmodulin, troponin C, S-100 and parvalbumin (R. H. Kretsinger et al., CRC Crit. Rev. Biochem. 8 (1980), p119) which is responsible for $Ca^{++}$ binding in these molecules, the conserving of this subsection in each repeat leads one to conclude that this region is responsible for the $Ca^{++}$ binding.

By controlled mutation in this area, attempts could be made to alter the biological activity of VAC proteins.

EXAMPLE 5

Expression of VAC-alpha in *E. coli* a) pRH284T: Expression vector with the alkaline phosphatase promoter and terminator The gene for alkaline phosphatase (PhoA) from *E. coli* is subject to stringent regulation. In the presence of phosphate, the gene is switched off completely and in the absence of phosphate in the medium genetic expression takes place. H. Shuttleworth et al., Nucleic Acids Res. 14 (1986) page 8689 and C. N. Chang et al., Gene 44 (1986), pp.121–125 describe the nucleotide sequence of this gene.

The promoter region of the PhoA gene was assembled from several oligonucleotides and inserted in pAT153 cut with EcoRI-ClaI. In front of the ribosomal binding site, an XhoI site was inserted. The original EcoRI site is destroyed when the synthetic DNA fragment is ligated in. After the ribosomal binding site, a translation start ATG was provided, the G of which is the first nucleotide of a SacI (=SstI) site. The expression vector can be linearized by cutting with SacI at this point and the 3' overhang can be converted into a straight end by treatment with DNA polymerase I—Klenow fragment in the presence of dGTP. In this way, any desired gene may be inserted at this point, and for correct expression it must begin with the first base of the coding region.

The HindIII-SalI fragment of the pAT section was removed and replaced by the alkaline phosphatase transcription terminator. The original SalI site was destroyed. In order to do this, it was reintroduced in front of the terminator together with the BamHI site which had also been deleted from pAT153. The sequence of the synthetically produced DNA is shown in FIG. 15.

b) Expression clone pRH291

The cDNA clone pP6/5 was cut with BglII and PstI and the 980 bp long fragment which contains the majority of the coding region and about 200 bp 3' untranslated region was isolated. The missing 5' end of the coding region was replaced by means of oligonucleotides. By two mutations (GGC→GGT, Gly-7 and ACT→ACC, Thr-8), at the same time a KpnI cutting site was introduced into the VAC-cDNA.

The oligonucleotides had the following appearance:
|EBI-678 ||EBI-677
5' EGCACAGGTTCTCAGAGGTACCGTGACT-GACTTCCCTGGATTTGATGAGCGGGCT 3'
CGTGTCCAAGAGTCTCCATGGCACT-GACTGAAGGGACCTAAACTACTCGCCCGA
|EBI-680||
GATGCAGAAACTCTTCGGAAGGCTAT-GAAAGGCTTGGGCACAGATGAGGAGAGC
CTACGTCTTTGAGAAGCCTTC-CGATACTTTCCGAACCCGTGTCTACTCCTCTCG
EBI-||EBI-682|
ATCCTGACTCTGTTGACATCCCGAAG-TAATGCTCAGCGCCAGGAAATCTCTGCA 3'
TAGGACTGAGACAACTGTAGGGCTTCAT-TACGAGTCGCGGTCCTTTAGAG 5'679||EBI-681|

The oligonucleotides EBI-680, 677, 678 and 682 were phosphorylated at the 51 end. EBI-678 and 680, EBI-677 and 679 and EBI-682 and 681 were heated to 100° C. in pairs and slowly cooled (100 pMol in 20 mcl). The double-stranded oligonucleotides were combined and ligated. pRH284T was linearized with SacI, the 3' overhanging end was reduced to a straight end by treating with DNA polymerase I/Klenow fragment in the presence of dGTP, and then recut with BamHI. About 30 ng of vector, 200 ng of cDNA and 250 nMol of oligonucleotides were ligated in 15 mcl of solution. Competent E. coli HB101 were transformed with the ligase solution. The resulting clone was designated pRH291 (FIG. 16).

EXAMPLE 6

VAC-beta expression in E. coli a) Expression clone pRH212

The plasmid pER103 was used as expression vector (E. Rastl-Dworkin et al., Gene 21 (1983), 237–248). The vector was linearized with HindIII. The 51 overhanging end was partly filled in with dATP and DNA polymerase I/Klenow fragment and the remaining single strand residue was digested with S1 nuclease. The vector was recut with BamHI and the large fragment was isolated (FIG. 17). The 440 bp long MaeIII-BamHI fragment which contains codons 13 to 157 was isolated from the clone pRH203. The missing 5' end was supplemented by the oligonucleotides:

EBI-307
5' CCATGGCTTGGTGGAAAGCTTGGATC-GAACAGGAAGGT 3'
3' GGTACCGAACCACCTTTCGAACCTAGCT-TGTCCTTCCACAGTG 5'
EBI-306

Optimum codons for E. coli were used (e.g. R. Grantham et al., Nucleic Acids Res. 8 (1980), 1893–1912). This codon exchange results in a new HindIII site at codon 5 to 7. The oligonucleotide EBI-306 was phosphorylated, hybridized with EBI-307 and ligated with the VAC-beta fragment. After recutting with BamHI the 5' terminal VAC fragment was ligated into the prepared pER103 vector. The resulting clone was designated pRH211. To complete the region coding for VAC-beta, the BamHI-SphI fragment 1230 bp long was isolated from the clone pRH201. The pBR322 section, approximately 200 bp long, from BamHI to SphI from the plasmid pRH211 was removed and replaced by the corresponding VAC-cDNA part. This resulted in the clone pRH212. The EcoRI-BamHI fragment which contains the Trp promoter (S. marcescens), the ribosomal binding site and the synthetically produced start of the VAC-beta gene was checked by sequencing.

b) Expression of VAC-beta (pRH212)

The plasmid-coded VAC-beta was detected in the Maxi-cell system (A. Sancar et al., J. Bacteriol. 137 (1979), pp.692–693). E. coli CSR603 (F⁻, thr-1, leuB6, proA2, phr-1, recA1, argE3, thi-1, uvrA6, ara-14, lacY1, galK2, xyl-5, mtl-1, gyrA98 (nalA98), rpsL31, tsx-33, lambda⁻, supE44) was transformed with pRH212 and grown to an $OD_{600}$ at 37° C. 20 ml of culture were irradiated in an open Petri dish with a UV germicidal lamp (15W) from a distance of 50 cm for 5 seconds and then incubated for another hour. 100 μg of D-cycloserine were added to the culture. After 16 hours the bacteria were removed by centrifuging, washed twice with Hershey saline solution (5.4 g/l NaCl, 3.0 g/l KCl, 1.1 g/l $NH_4Cl$, 15 mg/l $CaCl_2 \times 2H_2O$, 87 mg/l $KH_2PO_4$, 12.1 g/l Tris pH=7.4), resuspended in 5 ml of Hershey medium (per 100 ml of Hershey salts: 2.0 ml of 20% glucose, 0.5 ml of 2% threonine, 1.0 ml of 1% leucine, 1.0 ml of 2% proline, 1.0 ml of 2% arginine, 0.1 ml of 0.1% thiamine-HCl) and incubated for 2 hours with 20 μg/ml of indoleacrylic acid. After the addition of 5 μCi/ml of $^{35}$S-methionine and further incubation at 37° C. (1 hour) the plasmid-encoded proteins were radioactively labelled. The bacteria were centrifuged off and taken up in 200 μl of SDS probe buffer (Lämmli Gel System, e.g. L. G. Davies et al., Methods in Molecular Biology (1986) pp.306–310). The labelled products were separated on a 15% acrylamide gel. The gel was dried and exposed on Kodak X-Omat S film. As a reference, purified VAC-alpha protein was run with it and made visible by staining. VAC-alpha runs rather faster than the pRH212 encoded VAC-beta, as might be expected from the molecular weight. The expression of VAC-beta can also be stimulated by the addition of the inducer indoleacrylic acid (FIG. 18).

c) Expression clone pRH292

The expression vector pRH284T was linearized with SacI and the 3' overhanging ends were converted into straight ends with DNA polymerase I/Klenow fragment and dGTP. The vector was recut with SalI and the large fragment was isolated. The HindIII-SalI insert of the clone pRH212 was isolated. 0.2 pMol of the oligonucleotide pair
5' GCTTGGTGGAA 3' EBI-684
3° CGAACCACCTTTCGA 5' EBI-685
was ligated with 0.2 pMol of VAC-beta insert and 0.015 pMol of prepared pRH284T. E. coli HB101 was transformed with the ligase solution. The resulting clone was designated pRH292 (FIG. 19).

EXAMPLE 7

Detecting the expression of VAC-alpha and VAC-beta in *E. coli* a) Cultivation of the clones HB101/pRH291 and HB101/pRH292

Media: 1) Preliminary culture 10 g/l tryptone
5 g/l yeast extract
4 g/l glucose
9 g/l Na$_2$HPO$_4$.2H$_2$O
1 g/l NH$_4$Cl
1 ml/l 1M MgSO$_4$.7H$_2$O
100 mg/l ampicillin
Initiation pH=7.2
2) Main culture
0.68 g/l (NH$_4$)$_2$HPO$_4$
0.62 g/l K$_2$EPO$_4$.3H$_2$O
2.33 g/l KCl
0.5 g/l NaCl
0.53 g/l NH$_4$Cl
1.23 g/l MgSO$_4$.7H$_2$O
0.011 g/l CaCl$_2$
10 mg/l thiamine.HCl
3.92 mg/l (NH$_4$)$_2$Fe(SO$_4$)$_2$6H$_2$O
0.72 mg/l AlCl$_3$.6H$_2$O
0.72 mg/l CoCl$_2$.6H$_2$O
1.5 mg/l KCr(SO$_4$)$_2$.12H$_2$O
0.75 mg/l CuSO$_4$.5H$_2$O
0.19 mg/l H$_3$BO$_3$
0.51 mg/l MnSO$_4$.H$_2$O
0.79 mg/l NiSO$_4$.6H$_2$O
0.73 mg/l Na$_2$MoO$_4$.2H$_2$O
0.86 mg/l ZnSO$_4$.7H$_2$O
21 g/l casein hydrolysate (Merck Art. No. 2238)
25 g/l casein hydrolysate (sigma C9386)
100 mg/l cysteine
2 g/l yeast extract
1 g/l citric acid
11 g/l glucose.H$_2$O (start or feed)

700 ml of preliminary culture medium were inoculated with the expression clone and incubated for 12 to 15 hours at 37° C. with stirring (1000 rpm (revolutions per minute), magnetic rod) and with the introduction of oxygen (5 vvm (=vol/vol/min), ventilation grid). 600 ml of this preliminary culture were transferred into a fermenter containing 12 liters of main culture medium. The main culture was fermented under the following conditions:

Stirrer system: blade stirrer at 1000 rpm
Ventilation: 1.0 vvm
Temperature: 28° C.
pH: 6.5 (25% NH$_3$ for correction)

During fermentation the glucose concentration was measured. When it fell to 5 g/l, 10 g/l of glucose was added. All other additions, of 10 g/l in each case, were carried out when the glucose concentration in the fermenter fell to 10 g/l. If the partial oxygen pressure fell to about 0.05 atm, the pressure in the fermenter was increased to 0.3 bar. After 20 hours the mixture was cooled to 15° C., the biomass was separated from the nutrient medium by means of a CEPA centrifuge and frozen at −70° C.

b) Detection of the recombinant VAC-alpha or VAC-beta protein
Solutions:
Probe buffer:
125 mM Tris pH=6.8
4% SDS
10% mercaptoethanol
10% glycerol
0.02% bromophenol blue
Acrylamide gel:

| Stacking gel: | Separating gel |
|---|---|
| 3% acrylamide | 13.5% acrylamide |
| 0.1% bisacrylamide | 0.45% bisacrylamide |
| 125 mM Tris pH = 6.8 | 375 mM Tris pH = 8.8 |
| 0.1% SDS | 0.1% SDS |
| Eluant buffer: | |
| 14.4 g/l of glycine | |
| 3.025 g/l Tris | |
| 5 ml 20% SDS | |

Protein gel staining solution: Destaining solution:

| | |
|---|---|
| 0.1% Coomassie Blue | 5% methanol |
| 50% methanol | 10% acetic acid |
| 10% acetic acid | |

Glycerol solution:
7% acetic acid
2% glycerol
Transfer buffer:

| 10× transfer buffer: | 1× transfer buffer: |
|---|---|
| 24.4 g/l Tris | 100 ml/l 10× transfer buffer |
| 112.6 g/l glycerol | 200 ml/l methanol |
| | 1 ml/l Empigen |
| Blocking solution | PBS: |
| 1% Tween 20 | 8 g/l NaCl |
| 1% BSA (bovine serum albumin) | 0.2 g/l KCl |
| 10% foetal calves' serum | 1.15 g/l Na$_2$PO$_4$ |
| (GIBCO) in PBS | 0.2 g/l KH$_2$PO$_4$ |
| | 0.1 g/l MgCl$_2$ |
| | 0.7 g/l CaCl$_2$ |

Alkaline phosphatase buffer:
100 mM Tris pH=9.5
100 mM NaCl
5 mM MgCl$_2$

At the end of fermentation, the optical density of the liquor was determined and one aliquot was taken. The bacteria were pelleted in an Eppendorf centrifuge, resuspended in probe buffer with a concentration of 20 OD$_{600nm}$ (optical density at 600 nm) and denatured for 5 min at 100° C. Any insoluble parts were pelleted by centrifuging in the Eppendorf centrifuge. 5 µl aliquots were charged onto the acrylamide gel. The reference used consisted of expression clone which had been constantly grown at a higher phosphate concentration (0.08 mM phosphate). Under these conditions, the alkaline phosphatase promoter was not activated.

The proteins were separated at 6.5 V/cm (stacking gel) or at 13 V/cm (separating gel) according to the molecular weight until the bromophenol blue dye had reached the end of the gel. Half the gel was stained with Coomassie Blue. For this purpose, the gel was agitated in the staining solution for 30 minutes and then treated for one hour in the destaining solution. In order to remove excess stain more satisfactorily, a dialysis tube filled with activated charcoal was dipped into the destaining solution. The gel was then treated for 30 min in the glycerol solution and dried by means of a gel drier.

The proteins of the second gel half were transferred to a nitrocellulose filter. To do this, Sandwich Whatman 3MM paper gel nitrocellulose (Schleicher-Schuell, BA85) Whatman 3MM paper in a Biorad transfer apparatus was exposed to a voltage of 150 V (current intensity 1000 mM) in 1x transfer buffer for 2 hours with cooling. The nitrocellulose filter was treated overnight at ambient temperature in 50 ml of blocking solution. The filter was incubated for 3 hours in 5 ml of blocking solution /1:1000 dilute rabbit anti-VAC antiserum and then washed for 30 min in running water, and 3x for 15 min in PBS/1% Tween 20 (Merck-Schuchardt No. 822184). The filter was incubated for 3 hours at ambient temperature in 20 ml of blocking solution with a 1:2000 dilution of the anti-rabbit IgG (Fc) alkaline phosphatase conjugate (Promega-ProtoBlot Immunoscreening System). It was washed in running water and PBS/1% Tween 20 as described above. The bound antibody-alkaline phosphatase conjugate was detected by a colour reaction (Promega-ProtoBlot Immunoscreening System). 66 mcl of NBT (50 mg/ml nitro-blue tetrazolium in 70% dimethylformamide) and 33 µl of BCIP (50 mg/ml of 5-bromo-4-chloro-3-indolyl-phosphate in dimethylformamide) were dissolved in 10 ml of alkaline phosphatase buffer. The nitrocellulose filter was incubated in this solution until the colour developed and then washed for 30 min with running water. The filter was dried and heat-sealed in plastic film.

FIG. 19 shows the results. "+Phosphate" is the control with no expression, "−phosphate" shows the expression of VAC-alpha (clone HB101/pRH291) or VAC-beta (clone HB101/pRH292) protein under the control of the alkaline phosphatase promoter. Both VAC-alpha and also VAC-beta protein can be readily detected on the stained gel. The quantity of VAC proteins formed is, surprisingly, at least 20 mg/l/$OD_{600nm}$ bacterial culture.

Western blot clearly shows the stained VAC-alpha band. In addition, some proteins of lower molecular weight can be detected in the range up to 30 kD, possibly formed by proteolytic cleavage at the N and/or C-terminus of the VAC-alpha protein. A protein recognized by the anti-serum in the range below 20 kD, which might be a half-molecule of VAC-alpha protein formed by proteolysis, is also noticeable. Surprisingly, VAC-beta was also recognized by the anti-VAC antiserum. Since this band is substantially less strongly stained than the VAC-alpha band but the VAC-beta band in the Coomassie blue-stained gel corresponds to the VAC-alpha in its intensity, it can be concluded that the recognition of the VAC-beta protein by the anti-VAC anti-serum is substantially worse than that of the VAC-alpha protein.

EXAMPLE 8

Purification of recombinant VAC-alpha
Starting material: E. coli HB101/pRH291. The cells were centrifuged and frozen at −70° C.
a) Cell homogenization and extraction 103.5 g of frozen cell cake was suspended in 500 ml of ice cold lysis buffer (100 mM Tris/HCl, 50 mM EDTA and 200 mM NaCl, pH 7.5) and treated with an Ultra-Turrax (5 brief pulses) in order to destroy any clumps. The suspension was then passed 3 times through a Manton-Gaulin press at 6,000 psi. Finally, the press was rinsed with 300 ml of lysis buffer. A 5% solution of PEI (polyethyleneimine, molecular weight 30,000–40,000) which had been adjusted to pH 8 using 5N HCl, was slowly added to the homogenized suspension until a final concentration of 0.5% PEI was established. After having been stirred for 30 minutes in an ice bath, the solution was clarified at 9,000 g, 60 min and at 4° C. using a Beckmann J2-21 centrifuge (crude extract).
b) Ammonium sulphate fractionation:
Solid ammonium sulphate was slowly added to the stirred crude extract up to a saturation of 30% (176 g/l). The precipitate was removed after one night in the refrigerator. The clear supernatant was slowly mixed with solid ammonium sulphate until a saturation of 65% was achieved (235 g/l supernatant) and then stirred for 2 hours. The precipitate was then collected by centrifuging at 10,000 g 30 min at 4° C. It was dissolved in 500 ml of 20 mM Tris/HCl+50 mM NaCl, pH 7.4, and dialyzed with the same buffer until all the ammonium sulphate had been removed (determined by the absence of $BaSO_4$ formation after the addition of $BaCl_2$ to the dialyzate).
c) Chromatography on DEAE-SEPHAROSE FAST FLOW
The dialyzate was clarified by centrifuging and applied to a 160 ml DEAE-FF-Sepharose column (Pharmacia) which had been equilibrated with 20 mM Tris/HCl+50 mM NaCl, pH 7.4. As soon as the $OD_{280nm}$ of the eluate reached the buffer level, a gradient of 50–500 mM NaCl in 20 mM Tris/HCl, pH 7.4, was applied (in all, 10 column-volumes of the linear gradient). The eluate was monitored at $OD_{280nm}$ and analysed by SDS-PAGE and Western blot using a rabbit antiserum against placenta VAC, prepared in the manner described for the bovine VAC in EPA 0181465, and a swine anti-rabbit IgG coupled to alkaline phosphatase. Any fractions containing VAC were collected, and some fractions were discarded at the end of the main peak. The VAC pool was concentrated using an AMICON ultrafiltration cell and PM 10-type Ultrafilter.
d) Chromatography on Sephacryl S-200 "High Resolution"
A Pharmacia K 26/100 column (500 ml) was charged with Sephacryl S-200 HR (Pharmacia) and equilibrated with 20 mM bis-Tris/HCl +100 mM NaCl, pH 6.3, at a throughflow rate of 15–20 ml/hour. 6–15 ml aliquots of the concentrated DEAE-FF-Sepharose pool (total 87.4 ml) and subsequently the bis-Tris buffer (see above) were applied to the column. The eluate was monitored at $OD_{280nm}$. The peak representing VAC was the last noticeable peak of the UV profile, as could be shown by SDS-PAGE and Western blots of aliquots. It was collected, the pools from all the tests were combined (7 in all) and dialyzed against 20 mM bis-Tris/HCl pH 6.3.
e) Chromatography on a Q-SEPHAROSE-FAST-FLOW A 40 ml column (K 16/20) of a Q-Sepharose-fast-flow (Pharmacia) was connected up to the FPLC system (Pharmacia) and equilibrated with 20 mM bis-Tris/HCl, pH 6.3. The dialyzed VAC pool was applied to the column and washed with 20 mM bis-Tris until the $OD_{280nm}$ of the eluate had returned to the buffer level. An NaCl gradient in 20 mM bis-Tris/HCl, pH 6.3, was used for elution:
0–105 mM NaCl in 1 column volume (40 ml)
105–245 mM NaCl in 20 column volumes (800 ml)
245–350 mM NaCl in 2 column volumes (80 ml)
VAC could be identified in the last prominent peak of the UV profile, eluting at approximately 0.14M NaCl. The purity was determined by SDS-PAGE, Western blot, reverse HPLC and isoelectric focussing. The VAC pool was kept at −20° C.

EXAMPLE 9

Comparison of recombinant and natural VACα

Methods used:
a) Gel permeation HPLC
b) Reverse Phase HPLC
c) N-terminal sequencing
d) Tryptic peptide map
e) SDS gel electrophoresis
f) Western blot
g) Isoelectric focussing For the comparison, natural VAC was used on the one hand and recombinant VAC-alpha on the other hand. The test conditions for the individual methods of analysis are described hereinafter.

a) Gel permeation HPLC

| Column: | Waters Protein Pak I 125, 2× (7.8 × 300 mm), 10 micron particle diameter |
|---|---|
| Eluant: | 0.5M Na$_2$SO$_4$, 0.02M NaH$_2$PO$_4$, pH 7.0, 0.04% Tween 20, 25% propylene glycol |
| Flux: | 0.5 ml/min |
| Detection: | UV absorption, 214 nm |

The chromatograms of natural and recombinant VAC-alpha show the main peak of the VAC monomer at a molecular weight of 34,000 and 33,000, respectively. In addition, there is a small amount of earlier eluting dimers of the VAC. The molecular weight scale was calibrated by means of 4 standard proteins. The column separates, strictly speaking, according to molecular size and not molecular weight.

b) Reverse Phase HPLC

| Column: | Bakerbond WP C$_{18}$ 4.6 × 250, 5 micron particle diameter, 30 nm pore diameter |
|---|---|
| Eluant A: | 0.1% trifluoroacetic acid in water |
| Eluant B: | 0.1% trifluoroacetic acid in acetonitrile |
| Gradient: | 20% B for 2 min, 20–68% B in 24 min, 68% B for 10 min, 68–20% B in 1 min |
| Flux: | 1.0 ml/min |
| Detection: | UV absorption, 214 nm and 280 nm |

The chromatograms of natural and recombinant VAC show a retention time of about 29 min for VAC. The very small peaks also present are only partly impurities in the VAC probe. All the peaks designated BW originate from the blind value of the column.

c) N-terminal sequencing

A peak of recombinant VAC-alpha which had been desalinated by reverse phase HPLC was sequenced. Sequencing was effected with a gas phase sequenator made by the firm Applied Biosystems (Model 470A) using the program 40 APTH. The probe was dissolved in 50 μl of 70% HCOOH. 2×25 μl were appled to the sequenator. With an initial quantity of 2.3 nMol, it was possible to sequence up to amino acid 39. 100% agreement was found with the expected sequence (from natural protein and cDNA). No additional N-terminal Met could be detected ($\leq 1\%$). In recombinant VAC-alpha the N-terminus is free and not blocked, as in natural VAC.

d) Tryptic peptide map

Natural VAC and recombinant VAC-alpha were compared. From both samples, VAC was desalinated by reverse phase HPLC, dried and dissolved in 0.1% NH$_4$HCO$_3$ For the cleavage, 4% by weight of trypsin (Worthington, TPCK treated, dissolved in a quantity of 1 mg/ml in water) were added and, after 6 hours incubation at 37° C., a further 4% by weight of trypsin were added. After further incubation overnight the peptides formed were separated by reverse phase HPLC. The enclosed chromatograms (214 nm and 280 nm) show a virtually identical peptide pattern.

| Column: | Waters μBondapak C$_{18}$, 3.8 × 300 mm, 10 micron particle diameter 10 nm pore diameter |
|---|---|
| Eluant A: | 0.1% trifluoroacetic acid in water |
| Eluant B: | 0.1% trifluoroacetic acid in acetonitrile |
| Gradient: | 0–55% B in 55 min, 55% B for 15 min, 55–0% B in 1 min |
| Flux: | 1.0 ml/min |
| Detection: | UV absorption, 214 nm and 280 nm | e) SDS gel electrophoresis

SDS gel electrophoresis was carried out largely according to the method originally described by U. K. Laemmli (Nature 227, 680–685 (1979)). Silver staining was carried out using the method of Oakley (Anal. Biochem. 105, 361–363 (1980)). The first gel shows a comparison between natural and recombinant VAC-alpha. The content of dimeric VAC was quantified by scanning with a laser densitometer and was 2% in natural VAC and 4% in recombinant VAC. The second gel shows only recombinant VAC-alpha applied both with and without DTT (dithiothreitol, reducing agent). This shows that the SDS-stable dimer is obviously bound via disulphide bridges which can be reduced with DTT.

Original solutions of the reagents

15% Ammonium persulfate solution APS)

150 mg of ammonium persulfate are dissolved in 1 ml of distilled water.

30% acrylamide+0.8% bis acrylamide

| Acrylamide | bis acrylamide | Water ad. |
|---|---|---|
| 15 g | 0.4 g | 50 ml |
| 30 g | 0.8 g | 100 ml |
| 45 g | 1.2 g | 150 ml |

The acrylamide is dissolved in the corresponding volume of water and filtered before use.

Separating gel buffer 1.5M Tris HCl, 0.4% SDS (sodium dodecylsulfate), pH 8.8

18.16 g Tris +0.4 g SDS is adjusted to pH 8.8 with conc. HCl and topped up to 100 ml with distilled water.

Stacking gel buffer 0.5M Tris-HCl, 0.4% SDS, pH 6.8

6.04 g Tris+0.4 g SDS is adjusted to pH 6.8 with conc. HCl and made up to 100 ml with distilled water.

Eluting buffer 25 mM Tris, 192 mM glycine, 0.1% SDS, 0.005% Na-azide, pH 8.5

12 g Tris+57.6 g glycine+4 g SDS+0.2 g sodium azide are dissolved in about 3.5 l of distilled water, adjusted to pH 8.5 and made up to 4.0 liters. It is advisable to compare the conductivity of the new eluting buffer with the preceding batches.

0.05% Coomassie Blue staining solution 0.55 g of Coomassie Brillant Blue R 850 are dissolved in 500 ml of methanol, stirred for 30 min and filtered. 100 ml of glacial acetic acid and 500 ml of distilled water are added thereto.

Destaining solution
a) Manual destaining The destaining solution corresponds to the staining solution without the dye: 500 ml of methanol +500 ml of distilled water +100 ml of glacial acetic acid
b) Electrophoretic destaining in 7.5% acetic acid.

4x SDS application buffer (can be kept for about 1 month)

| Dye concentrate: | Bromophenol blue | 50 mg |
| --- | --- | --- |
| | Glycerol | 0.5 ml |
| | Distilled water ad. | 10 ml |

The solution can be kept for about 3 months.

| Application buffer: | dye concentrate | 0.4 ml |
| --- | --- | --- |
| | SDS | 0.8 g |
| | Glycerol | 4 g |
| | Distilled water ad. | 10 ml |

1 x SDS application buffer
Dilution 1:4 of the 4x SDS application buffer with distilled water.

Silver staining according to Oakley
Reagents

| Destainer: | Ethanol | 200 ml |
| --- | --- | --- |
| | Conc. acetic acid | 62.5 ml |
| | Distilled water ad. | 1000 ml |

10% Glutardialdehyde solution:

| 25% glutardialdehyde solution | 20 ml | or | 40 ml |
| --- | --- | --- | --- |
| Distilled water ad. | 50 ml | or | 100 ml |

The solution must be kept in a refrigerator.

0.1N ammoniacal silver solution:
Should only be prepared immediately before use:

| 0.1N silver nitrate (16.9 g/l) | 23 ml | 46 ml |
| --- | --- | --- |
| 25% ammonia solution | 0.9 ml | 1.9 ml |
| 0.36% sodium hydroxide (1.8 g/0.5 l) | 10.5 ml | 21 ml |
| distilled water ad. | 50 ml | 100 ml |

Developer solution:

| Prepare immediately before use: | | |
| --- | --- | --- |
| 0.5% citric acid (1.25 g/250 ml) | 5 ml | |
| distilled water | 1 l | |
| 37% formaldehyde | 1 ml | |

Destainer solution (Photofixer):
Kodak fixer (Photolaboratory) diluted 1:4 with distilled water. The dilution can be used several times but the time taken for destaining increases after frequent use.

2% glycerol solution:
23 g glycerol 87% in 1 l of distilled water.

Method of silver staining according to Oakley
After electrophoresis the gel was labelled at one corner and then underwent the following staining steps in the shaker:

30 min in the destainer bath 30 min in 20% glutardialdehyde solution (50 ml)

30 min in running water or overnight in about 2 l of water 10 min in ammoniacal silver solution (50 ml)

3 min in running water about 5 min in developer solution.

The developing process was not ended after an exact period of time but when the bands were sufficiently stained or, at the latest, when the background began to stain. Development was stopped by watering the gels for 30 min (in a tank or under running water).

Development still continued when the gel was in water: (diffusion time). Destaining of the gel was only necessary if the background was too strongly stained:

about 5–10 min in a Kodak fixer until optimum contrast between the bands and the background had been achieved. Note: Destaining also continued even after being stopped directly in running water (diffusion time).

30 min in 2% glycerol solution.

After this the gel could be dried on filter paper at 80° C. for one hour.

f) Western blot

Immunological proof was obtained for VAC with rabbit anti-VAC serum (diluted 1:1000) and with swine anti-rabbit IgG (1:500 dilution), which is conjugated with alkaline phosphatase. In order to detect the enzyme activity of alkaline phosphatase, the substrates BCIP (5-bromo-4-chloro-3-indolyl-phosphate) and NBT (nitro blue tetrazolium) were used. Comparative protein staining on the nitrocellulose was carried out with amido black.

Western blotting by the semi-dry method
1. Materials:

Semi-dry electroblotter (Messrs. Sartorius) SM 175 56; filter paper the same size as the gel which is to be blotted; nitrocellulose membrane (pore size 0.45 mcm) the same size as the gel;

2. Reagents

| Anode buffer 1: pH 10.4 | |
| --- | --- |
| 0.3M Tris | 3.63 g/80 ml |
| 20% methanol | 20 ml |

| Anode buffer 2: pH 10.4 | |
| --- | --- |
| 25 mM Tris | 0.3 g/80 ml |
| 20% methanol | 20 ml |

| Cathode buffer: pH 9.4 | |
| --- | --- |
| 25 mM Tris | 0.3 g/80 ml |
| 40 mM ε-aminocaproic acid | 0.52 g/80 ml (MW 131.3) |
| 20% methanol | 20 ml |

| Amido black protein staining medium | |
| --- | --- |
| 0.5% (w/v) amido black | 0.5 g in 40 ml |
| 50% methanol | 50 ml |
| 10% acetic acid | 10 ml |

Destainer
Methanol—water—acetic acid 5—5—1
PBS (Phosphate buffered saline) 10x concentrate pH 7.2

| | |
| --- | --- |
| 136 mM sodium chloride | 80 g |
| 26 mM calcium chloride | 2 g |
| 80 mM disodium hydrogen phosphate | 11.3 g |
| (80 mM disodium hydrogen phosphate.12H$_2$O | 28.7 g) |
| 14 mM potassium dihydrogen phosphate | 2 g |
| made up with distilled water to | 1 l |
| dilute 1/10 before use !!! | |

Blocking buffer:
1% BSA
0.1% Tween 20
in 1x PBS
Washing buffer:
1x PBS
1x PBS+0.1% Tween 20
1x PBS

| Staining buffer for alkaline phosphatase staining: | |
| --- | --- |
| pH 9.9 | |
| 100 mM Tris | 1.22 g |
| 100 mM sodium chloride | 0.58 g |
| 5 mM magnesium chloride.6H$_2$O | 0.10 g |
| made up to 100 ml with distilled water | |

NBT (Nitro blue tetrazolium) solution
50 mg NBT (Messrs. Sigma N-6876)/ml 70% dimethylformamide
BCIP (5-bromo-4-chloro-3-indolyl-phosphate) solution
50 mg BCIP (Messrs. Sigma B-8503)/ml in 100% dimethylformamide

| Staining medium for alkaline phosphatase | |
| --- | --- |
| Staining buffer | 10 ml |
| BCIP | 0.033 ml |
| NBT | 0.065 ml |

Antibody reagents:
Rabbit anti-VAC serum conjugated with alkaline phosphatase.
3. Effecting the blot
blotting was carried out at 0.8 mA/cm$^2$ of gel area over a period of 60 min.
4. Detecting the protein on the nitrocellulose membrane
4.1 Protein staining with amido black
The part of the nitrocellulose membrane intended for the protein staining was cut away and placed in amido black staining solution for 5 min. Then the staining solution, which could be used several times, was poured away and any excess staining solution was rinsed off the nitrocellulose membrane with water.
4.2 Immunological detection
4.2.1 Blocking of the nitrocellulose membrane
Before the immunological detection, the nitrocellulose membrane was blocked for at least 60 min (or overnight) with 1% BSA in 1 x PBS with 0.1% Tween 20.

4.2.2 Detection with enzyme-labelled antibodies
After blocking, the nitrocellulose membrane was incubated for 60 min with rabbit anti-VAC serum (suitably diluted in blocking medium).
It was then washed 3 times: 1x PBS, PBS with 0.1% Tween 20, 1 x PBS. The membrane was then incubated with swine anti-rabbit IgG, which was conjugated with alkaline phosphatase (also in a suitable dilution in blocking medium for 60 min). It was then washed again with 3 x PBS as described above.
4.2.3 Enzymatic staining of the blot
The nitrocellulose membrane was placed in staining medium (10 ml were sufficient for a minigel) and slowly moved about in a shaker until the bands appeared to be sufficiently stained. Staining was ended by washing out the staining medium with water, then the nitrocellulose membrane was dried in air.
5. Evaluation of the western blot
The immunologically/enzymatically detected bands of the blot were compared with the bands of protein staining of the blot and also with the corresponding band pattern of SDS electrophoresis and were assigned to one another.
7. Isoelectric focussing
The isoelectric point (pI) for recombinant VAC alpha, at 4.9, is 0.1 pH unit higher than for natural VAC (4.8).
Polyacrylamide gel—Isoelectric focussing (PAGIF or IEF)
Equipment and Reagents
Polyacrylamide gel plates for isoelectric focussing polymerised onto film. (LKB—"PAGplate", SERVA—"Servalyt Precotes")
Electrode solutions for the pH ranges in question:
pH 3.5–9.5 (LKB PAGplate)
Anode solution: 1M phosphoric acid
Cathode solution: 1M sodium hydroxide solution
pH 5.5–8.5 (LKB-PAGplate)
Anode solution: 0.4M HEPES (with Na-azide)
Cathode solution: 0.1M NaOH
pH 4.0–6.5 (LKB-PAGplate)
Anode solution: 0.5M phosphoric acid +0.1M glutamic acid
Cathode solution: 0.1M Beta-alanine (with Na-azide)
pH 3.5–9.5 (SERVALYT-Precotes)
Anode solution: 25 mM aspartic acid+25 mM glutamic acid
Cathode solution: 2M ethylenediamine +25 mm arginine base +37.5 mm lysine base
Coolant: Kerosene (made by SERVA)
Fixing solution: 10% Trichloroacetic acid (TCA) with 5% sulfosalicylic acid
0.05% Coomassie blue staining solution Destainer: 500 ml methanol+500 ml water+100 ml glacial acetic acid
Probes:
The probes should be low in salt, or better still, free from salt. Higher salt concentrations must be dialyzed against about 5–10 mM buffer or water before the IEF. NaCl, however, may be present in quantities of up to 100 mM without disrupting the elution fronts.
Fixing the IEF gel before protein staining
The gel was placed in the fixing solution for about 20 min but without shaking: (it is easily detached from the film). It was then watered for 5 min.
Protein staining of the IFF gels with Coomassie Blue
The fixed gels were placed in a staining solution for about 2 hours and moved around only very gently.
Destaining of the IEF gels
After the staining, the excess staining solution was rinsed away with water and the gel was destained by frequently changing the destainer. After it had been adequately destained the gel was watered again until the destainer had all been washed out.

Drying the IEF gels

The gels were placed on a wet, water-permeable transparent film or dialysis membrane with the water-impermeable side upwards and dried for one hour at 80° C.

EXAMPLE 10

Biological activity of recombinant VAC

Figure 33:
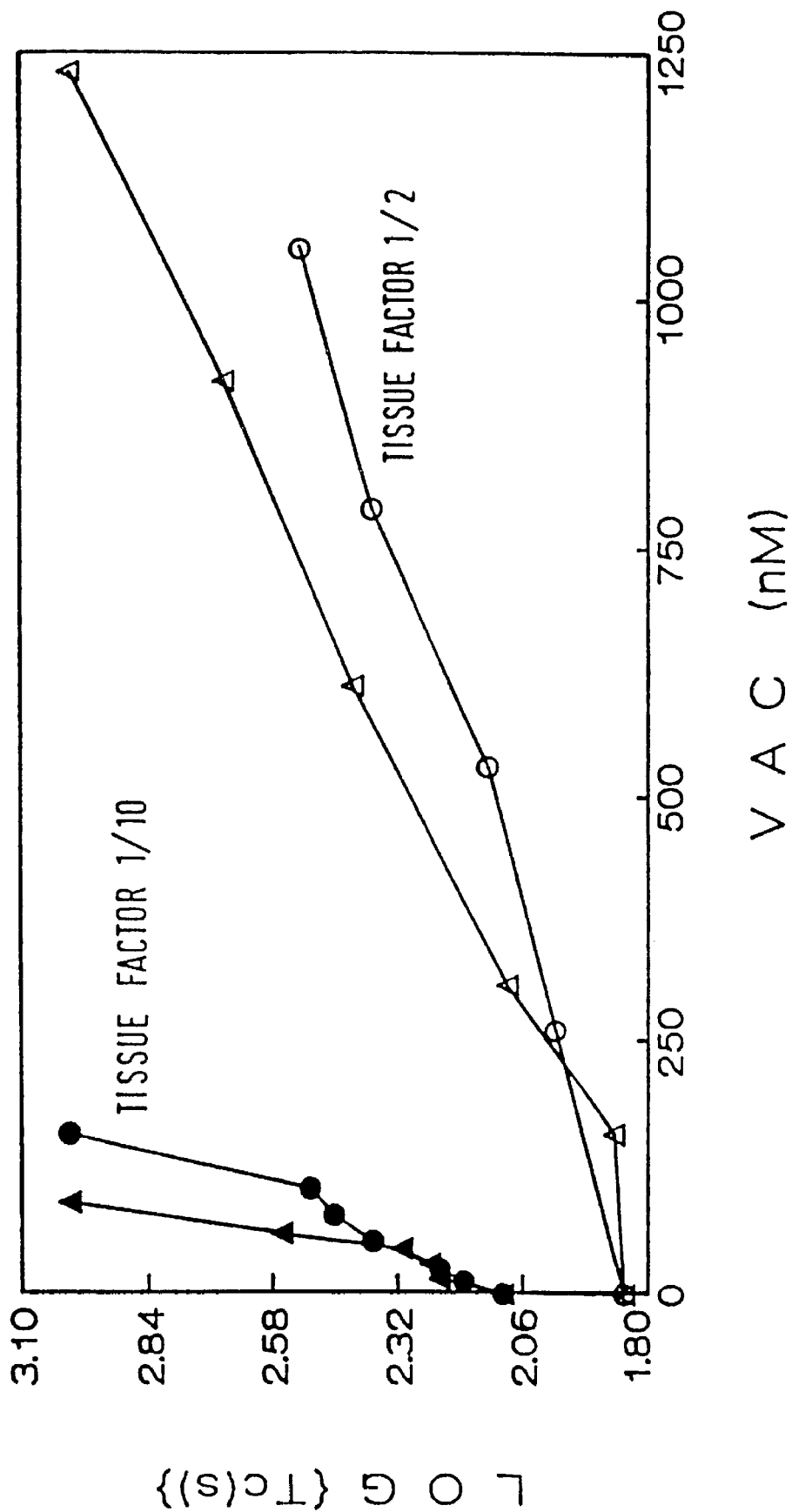

A. Modified prothrombin time test (see EPA 0181465) Citrated platelet-free plasma (PFP) was stirred for 2 min at 37° C. in the presence or absence of recombinant VAC (r-VAC) or natural VAC. After incubation, a solution of brain tissue factor and $Ca^{++}$ was added. The fibrin formation was observed and the coagulation time was recorded visually. The results are shown in FIG. 33 and prove that r-VAC and VAC inhibit fibrin formation as a function of dosage. The specific activities of r-VAC and VAC are obviously of the same order of magnitude.

Figure 34:
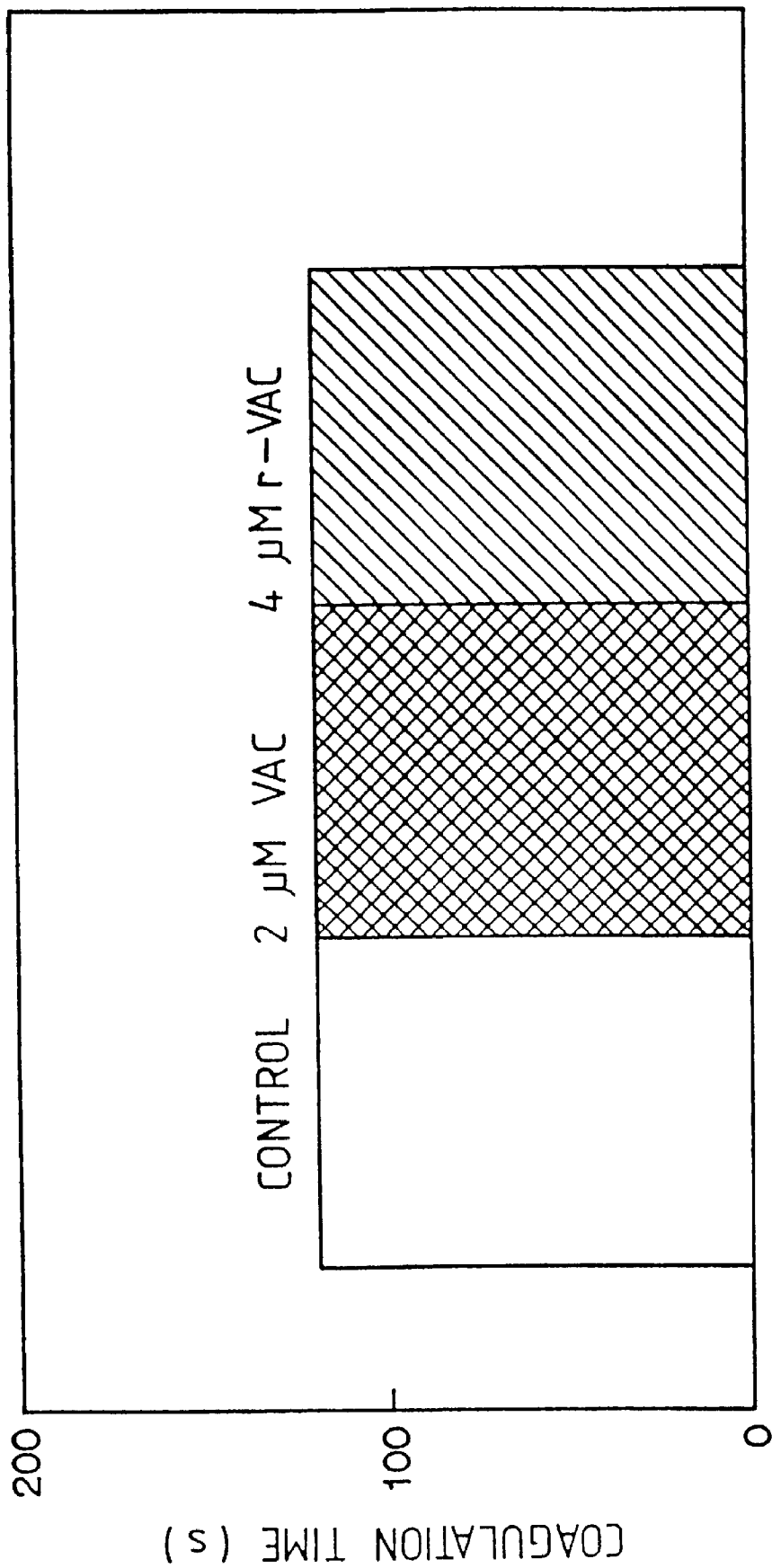

B. Thrombin time test (see EPA 0181465) Citrated PFP was stirred for 2 min at 37° C. in the presence or absence of r-VAC or VAC. After incubation, thrombin and Ca were added. The fibrin formation was observed visually. Neither r-VAC nor VAC inhibit the thrombin-induced fibrin formation, as can be seen from FIG. 34. Consequently, both r-VAC and VAC inhibit thrombin formation but not the activity of thrombin.

C. Factor Xa formation in tissue factor-activated plasma (see EPA 0181465)

Citrated PFP was stirred for 2 minutes at 37° C. in the presence or absence of r-VAC or VAC.

Subsequently, a solution of "brain tissue factor" and $Ca^{++}$ was added to the PFP in order to start off the coagulation. At certain times, samples were taken and diluted 1000 fold in a buffer. 10 µl of this solution were added to 40 µl of a mixture which contained the following components of the prothrombinase complex.

0.6 nM factor Va 50 µM phospholipids (80% dioleoyl-phosphatidylcholine/20% dioleoyl-phosphatidylserine). 1.0 µM prothrombin After a reaction time of 2 min, the amount of activated prothrombin was judged from the amidolytic activity using the chromogenic substrate S 2238. The quantity of amidolytic activity measured in this way is directly proportional to the quantity of active factor $X_a$ in the PFP.

After 100-fold dilution when VAC is present in the PFP, no effect on prothrombin activation could be observed.

Figure 35:
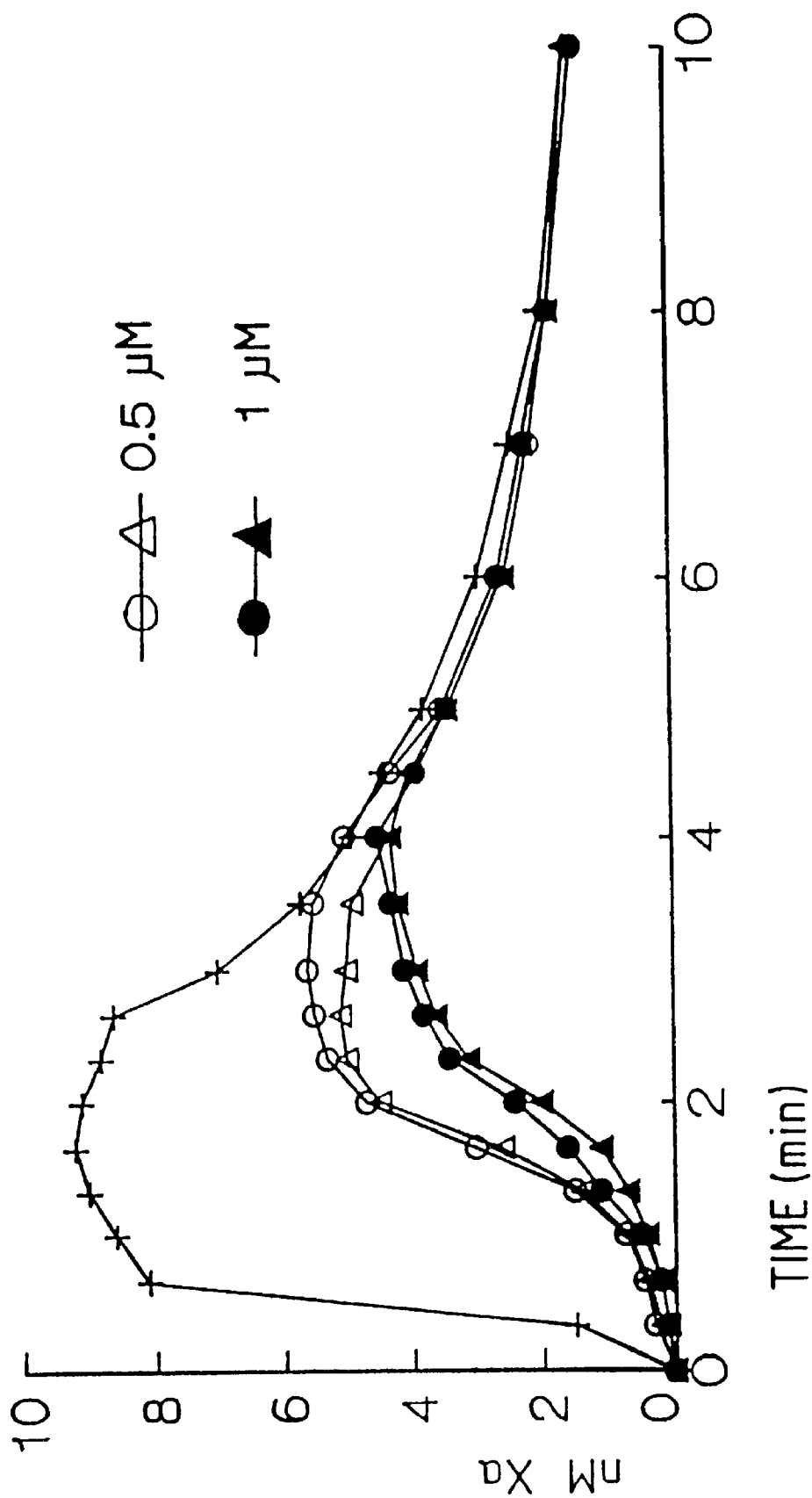

A typical factor $X_a$ formation curve and the effects of r-VAC and VAC are shown in FIG. 35. From these results it is possible to determine that r-VAC inhibits the tissue factor-induced factor X activation in plasma, as a function of dosage, in the same way as VAC.

The results also indirectly show that both r-VAC and also VAC do not inactivate the factor $X_a$ directly in a time-dependent manner. This statement can be made on the basis of the shape of the curve. After a maximum is reached, the quantity of active factor $X_a$ in the PFP begins to decrease, following pseudo first order kinetics. This decrease presumably results in the inactivation of the factor $X_a$ by antithrombin III. The pseudo first order speed constant calculated from these data is about 0.25 $min^{-1}$ and does not change when r-VAC and VAC are present.

These data clearly demonstrate that r-VAC has VAC activity. Although the specific activity of r-VAC in this coagulation test is identical to that of VAC and although r-VAC does not directly inactivate factor $X_a$ and thrombin, investigations were additionally carried out into the r-VAC bonding to phospholipids, in order to demonstrate beyond any doubt the fact that the VAC activity belongs to the r-VAC.

The binding of r-VAC and VAC to a phospholipid double layer consisting of dioleoyl-phosphatidylcholine and dioleoyl-phosphatidylserine (80%/20%) was determined by using an automatic ellipsometer. This method was described by Cuypers et al. in J. Biol. Chem. 258 (1983), 2426–2431.

Figure 36:
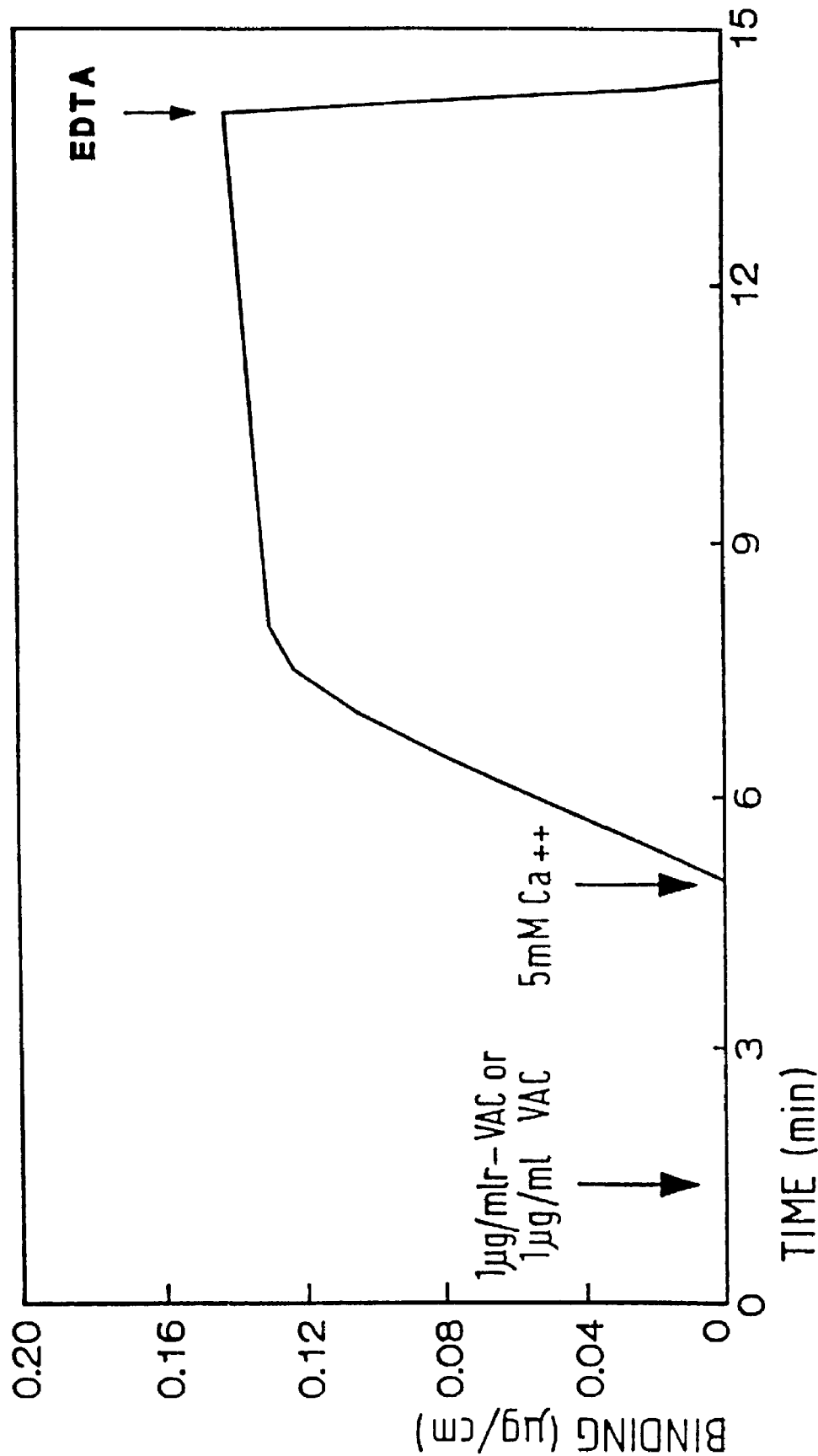
Figure 37:
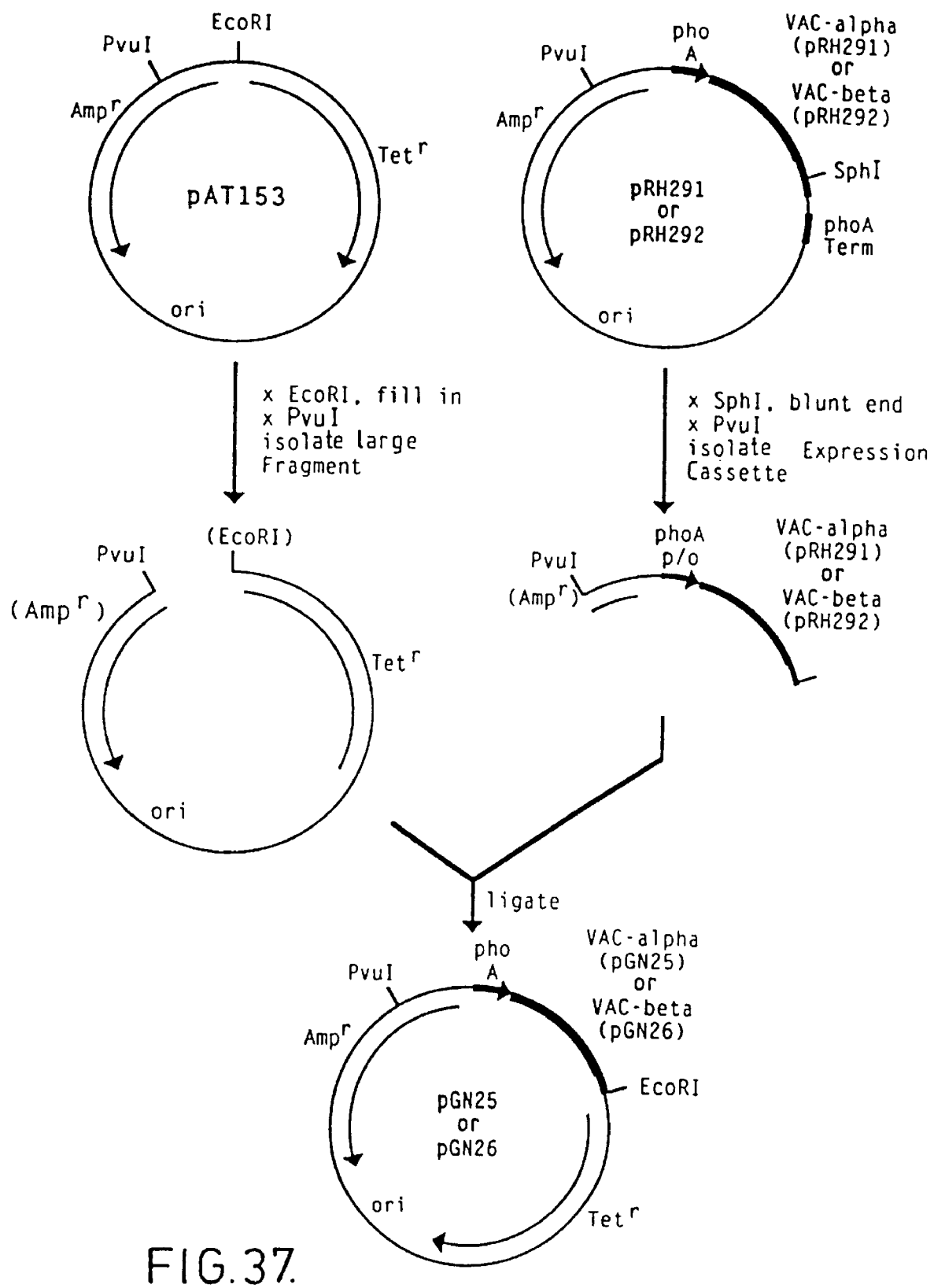
Figure 38:
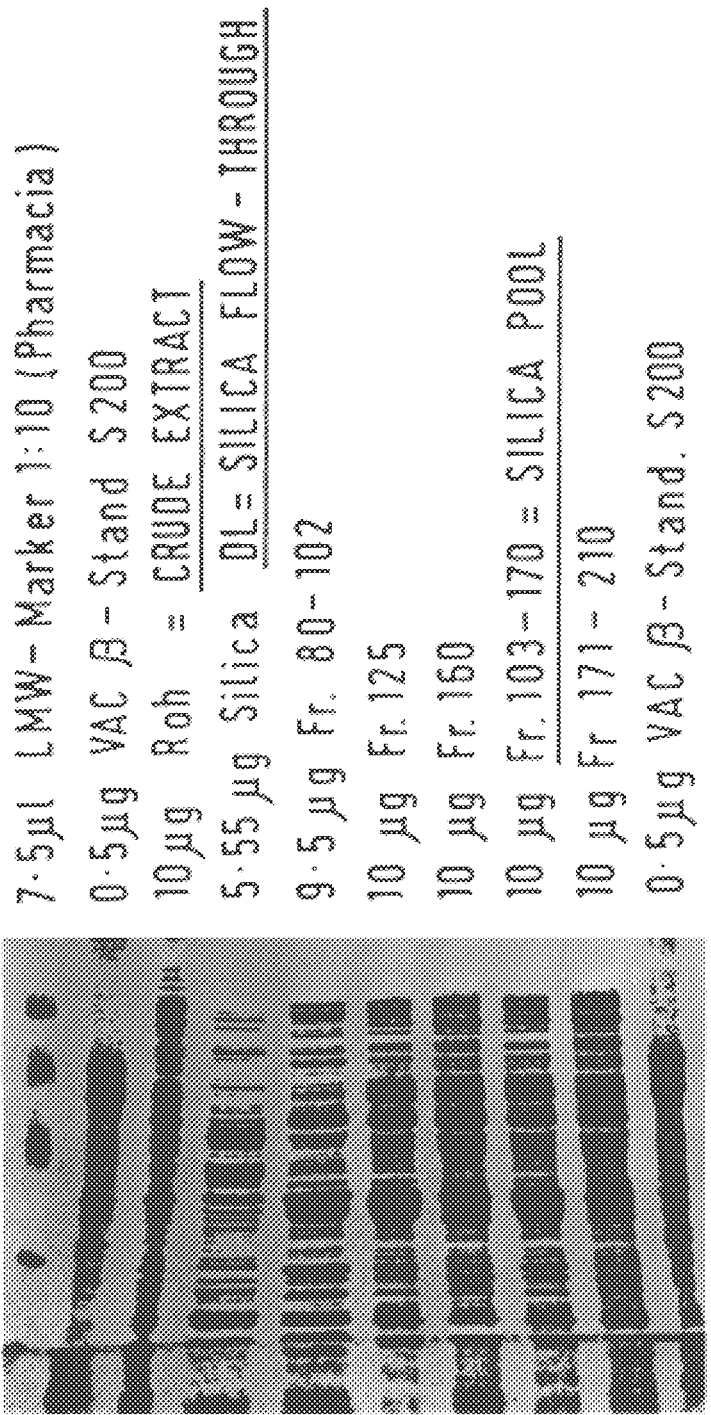

A typical result of this study is shown in FIG. 36. Both r-VAC and also VAC show identical binding kinetics to the double layer when added in a concentration of 1 µg of VAC per ml to this double layer. Binding is effected in the presence of $Ca^{2+}$ and is reversible, as can be demonstrated by the addition of EDTA.

To sum up, it is found that r-VAC is biologically active and cannot be distinguished from natural VAC.

EXAMPLE 11

Construction of tetracycline-resistant VAC-α and VAC-β expression vectors (pGN25, pGN26)

1 µl of pAT153 was cut with EcoRI in 50 mcl of solution. The enzyme activity was destroyed by heating to 70° C. and the overhanging ends were straightened by the addition of DNA polymerase I/Klenow fragment (PollK) (5 units) and the four deoxyribonucleoside triphosphates (20 µM each final concentration) in a fill-in reaction. After heating to 70° C. to destroy the PollK activity the DNA was precipitated with ethanol. The linearized DNA was recut with PvuI in 50 µl.

pRH291 and pRH292 were first linearized with SphI and the 3' overhanging end was degraded by the 3' exonucleolytic activity of PollK in the presence of dGTP. After precipitation of the DNAs these were recut with PvuI. The fragments from all three digestions were separated on agarose gel and the corresponding fragments were eluted (pAT153: 3032 bp, pRH291: 1987 bp, pRH292: 2607 bp). 50 ng of pAT153 fragment were mixed with 50 ng of pRH291 or pRH292 fragment and ligated in 10 µl. 100 µl of competent *E. coli* HB101 were combined with 5 µl of ligase solution and transformed. Selection was carried out on LB agar containing 100 µl/ml of ampicillin. Of the clones formed, some were spread out on LB agar with 12.5 µl/ml of tetracycline. The clones growing thereon were used to prepare plasmid DNA. The plasmid DNA prepared in a mini preparation was cut with various restriction enzymes and in this way the correctness of the construction was checked. One clone was selected in each case and designated pGN25 (VAC-α) or pGN26 (VAC-β).

*E. coli* HB101/pGN25 or HB101/pGN26 were subjected to fermentation as described in Example 7, but this time instead of the ampicillin 5 mg/l of tetracycline were used in the pre-culture. During the main fermentation, aliquots were taken and investigated on a 15% acrylamide/0.1% SDS gel according to Lämmli. No difference was found from the fermentations of *E. coli* HB101/pRH291 or HB101/pRH292. VAC-α and VAC-β were purified from the biomass of the fermentation. Protein analysis also showed no difference from the corresponding recombinant proteins from the fermentations of clones HB101/pRH291 and HB101/pRH292.

EXAMPLE 12

Purification of recombinant VAC-beta

Starting material:

*E. coli* clone HB101/pRH292

Cells were harvested by centrifugation and frozen at −70° C.

Cell homogenization and extraction 100 gms of frozen cells were suspended in 500 ml ice-cold lysis buffer (100 mM Tris/HCl, 50 mM EDTA and 200 mM NaCl, pH 7.5) and treated with 5 short pulses in an Ultra-Turrax to break lumps. The suspension was then passed 3-times through a Manton-Gaulin press at 6000 psi and the press finally rinsed with 300 ml lysis buffer. To the homogenised suspension was slowly added a 5% solution of PEI (polyethylene imine, mol. weight 30,000–40,000), which was adjusted to pH=8 with 5N hydrochloric acid, to give a final concentration of 0.5% PEI. After stirring in an ice-bath for 30 min., the solution was clarified at 9000 g for 60 min. at 4° C., using a Beckman J2-21 centrifuge, to obtain the crude VAC-beta extract.

Chromatography on Silica

Silica Catalyst Carrier, Grade 953 W, (Grace GmbH., Worms, BRD) was freed from fines by settling in distilled water and filled into a chromatographic column of 5 cm diameter and 20 cm bed height. After equilibration with lysis buffer, the crude extract was passed over the column and washed with 3 liters of lysis buffer. VAC-beta was eluted with a linear gradient of tetramethylammonium chloride in lysis buffer (0–1M in 2000 ml buffer). Fractions of the eluate were monitored by SDS-PAGE for VAC-beta, using a reference material. VAC-beta containing fractions were pooled.

Chromatography on DEAE-Sepharose Fast Flow

Pooled Silica-fractions were dialyzed against 20 mM Tris/HCl pH 8.4 and applied to a column (26×330 mm =175 ml) of DEAE-FF-Sepharose (Pharmacia) equilibrated with 20 mM Tris/HCl pH 8.4. The column was washed with 500 ml of buffer and VAC-beta eluted with a gradient of 0–500 mM NaCl in 875 ml buffer (5 column volumes). The eluate was monitored for protein content at 280 nm and protein containing fractions analyzed by SDS-PAGE, using a reference material. VAC-beta containing fractions were pooled and concentrated using an AMICON stirred ultrafiltration cell and a PM 10 ultrafilter.

Chromatography on Sephacryl S-200 "High Resolution"

A Pharmacia column K 26/100 (500 ml) was packed with Sephacryl S-200 HR (Pharmacia) and equilibrated with 20 mM Tris/HCl+100 mM NaCl pH 8.4 at a flow rate of 120 ml/h. The concentrated VAC-beta pool (4 ml) was applied to the column and the flow rate reduced to 60–80 ml/h. The eluate was monitored at 280 nm for protein. VAC-beta could be identified in the UV-profile as the only peak. It was pooled, thereby removing a shoulder of high molecular weight impurities, which were also detectable in the UV-profile. The purified VAC-beta was analyzed by SDS-PAGE and kept at −20° C.

Table: Purification of recombinant VAC-beta starting material: 100 g frozen cell paste.

|  | Volume (ml) | mg protein/ml[x] | mg total |
|---|---|---|---|
| CRUDE EXTRACT | 810 | 16.1 | 13,040 |
| SILICA FLOW-THROUGH | 2270 | 0.35 | 795 |
| VAC-beta SILICA POOL | 380 | 5.0 | 1,900 |
| VAC-beta DEAE-FF-POOL | 120 | 2.6 | 312 |
| DEAE-FF-POOL CONCENTRATE | 4 | 58 | 232 |
| VAC-beta SEPHACRYL-POOL | 33.5 | 2.2 | 74 |

[x]Protein by BIO-RAD protein assay (standard: bovine serum albumin)

EXAMPLE 13

Analysis and characterization of VAC-β

SDS gel electrophoresis was used as an in-process check between the individual purification steps. This analysis was carried out exactly as in the final checks and is described therein. A series of the SDS gels obtained during one purification is contained in Example 12 (purification of VAC-β).

Figure 40:
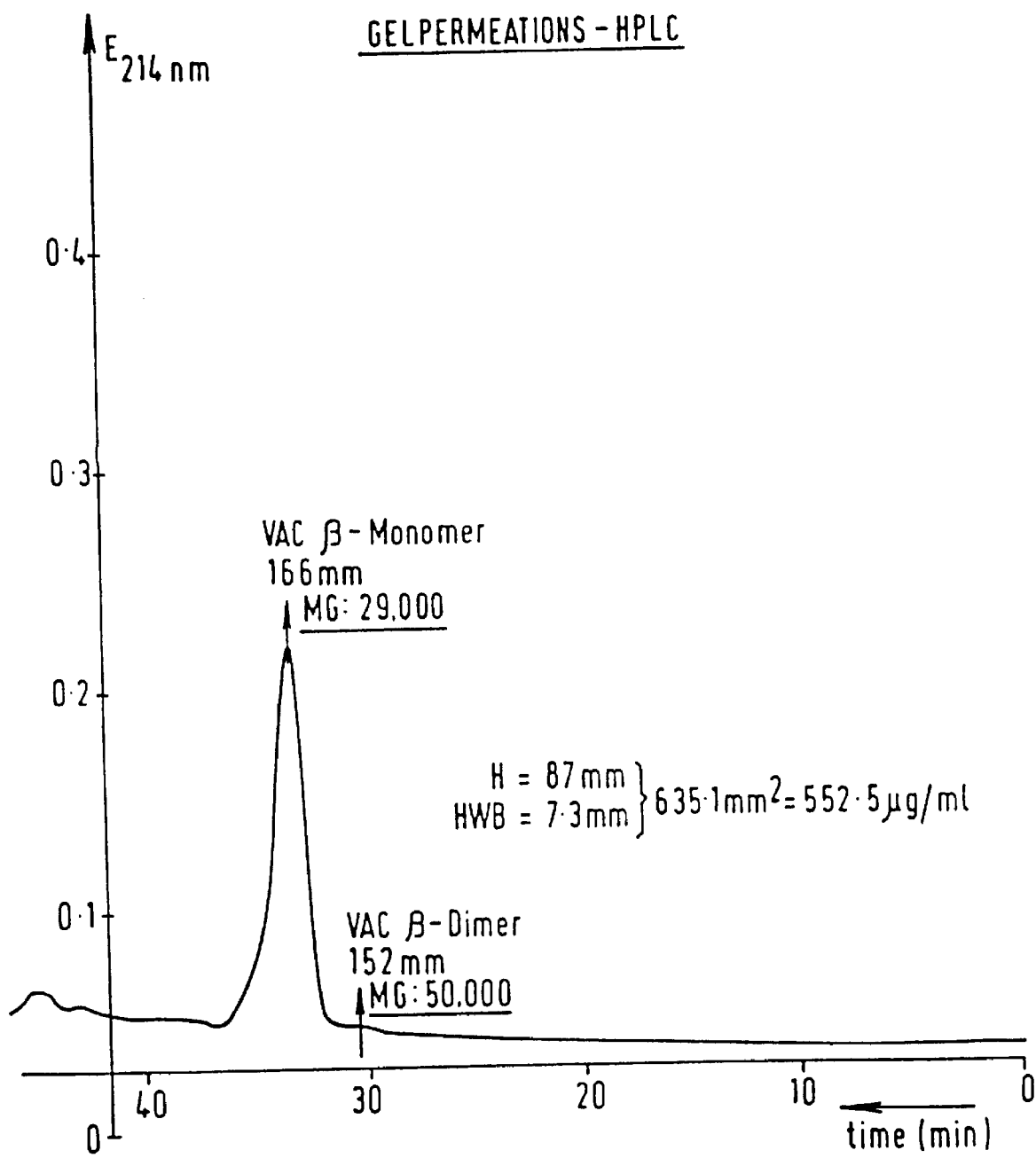
Figure 41:
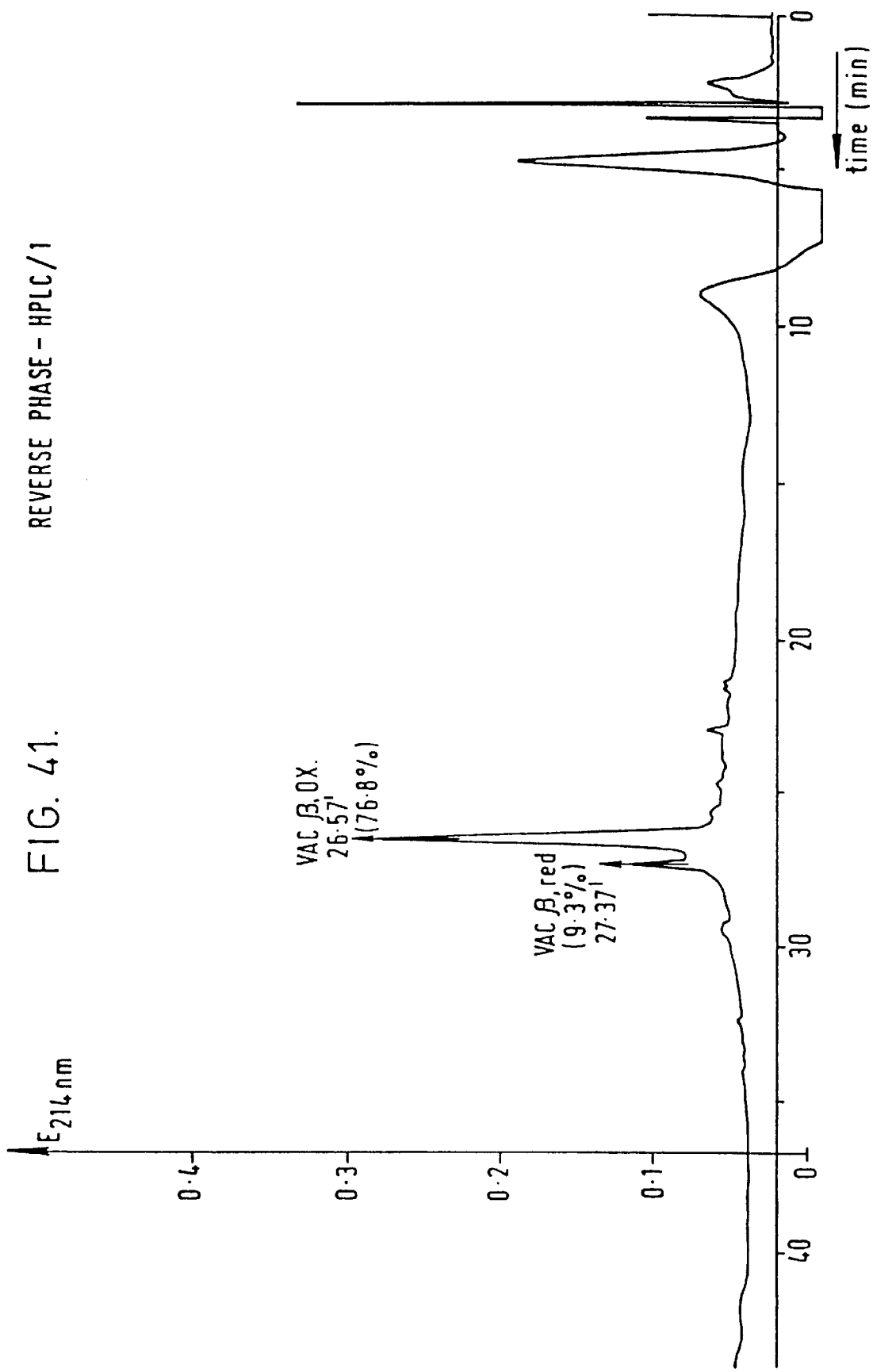

The following methods were used as final checks and to characterize the purified protein:
a) gel permeation HPLC
b) reverse phase HPLC
c) amino acid analysis
d) N terminal sequencing
e) SDS gel electrophoresis
f) isoelectric focussing a) gel permeation HPLC
column: Waters Protein Pak I 125, 2x(7.8×300 mm), particle diameter 10 μm, ambient temperature
eluant: 0.5M $Na_2SO_4$, 0.02M $NaH_2PO_4$, pH 7.0, 0.04% Tween 20, 25% propylene glycol
Flow rate: 0.5 ml/min
Detection: UV absorption, 214 nm, 0.5 OUT The chromatogram (FIG. 40) of purified VAC-β shows the main peak of the VAC-β monomer at a molecular weight of 29,000, and in addition a small amount of dimeric VAC-β can also be detected (M approx. 50,000). These values for the molecular weight are a relatively long way below the expected value (M 37,000), presumably because the gel permeation column used here separates on the basis of molecular size or configuration and not molecular weight.

b) Reverse phase HPLC
Column: Bakerbond WP $C_{18}$, 4.6×250 mm, particle diameter 5 μm, pore diameter 30 nm, ambient temperature
Eluant A: 0.1% trifluoroacetic acid in water
Eluant B: 0.1% trifluoroacetic acid in acetonitrile
Gradient: 20% B for 2 minutes, 20–68% B in 24 min., 68% B for 10 min., 68–20% B in 1 min.
Flow rate: 1 ml/min.
Detection: UV absorption, 214 nm, 0.5 OUT The chromatogram (FIG. 41) comes directly from the eluate of the last purification stage and shows the main peak of the oxidized VAC-β (two disulphide bridges, $t_R$=26.6 min.). In addition about 9% of reduced VAC-β ($t_R$=27.4 min.) and some smaller peaks of residual impurities can be detected.

Figure 42:
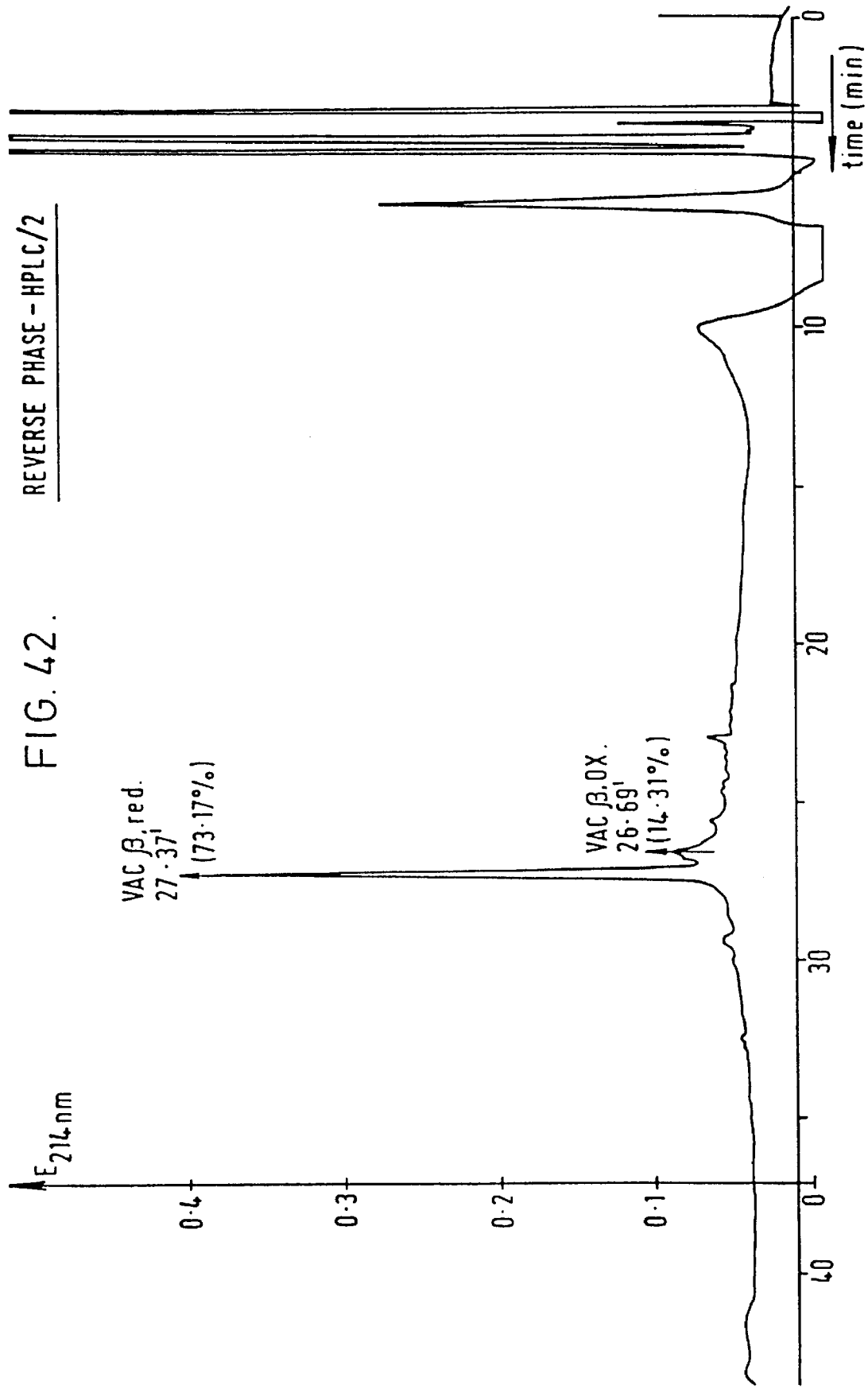

The chromatogram (FIG. 42) shows the same VAC-β sample after 2 hours' incubation in 3M urea, 0.05M dithiothreitol. The protein occurs mainly in the reduced form ($t_R$=27.4 min.).

c) Amino acid analysis
Purified VAC-β was desalinated by reverse phase HPLC (for method see paragraph b). The main peak of VAC-β was collected in a hydrolysis tube and dried.

Hydrolysis was carried out with 6N hydrochloric acid (with 1% phenol) in the gaseous phase (110° C., 22 hours).

The amino acids were measured with an amino acid analyser (type 6300, made by Beckman) by a post-column derivatisation with ninhydrin.

The amino acid analysis (FIG. 43) of a VAC-β sample shows a total deviation from the theoretical composition of 6.56%.

d) N terminal sequencing
Purified VAC-β was desalinated by reverse phase HPLC (for method see paragraph b). The main peak of VAC-β was collected and dried.

The residue was dissolved in 75 µl of 0.1% trifluoroacetic acid and used directly for sequencing.

Sequencing was carried out with a gas phase sequenator made by Applied Biosystems (Model 470 A 9) with the program 39 apth.

It was possible to sequence up to the 39th amino acid with an initial quantity of about 1 nM. 100% agreement with the expected sequence was found. Obviously, N-terminal methionine was split off 100%. (FIG. 44).

e) SDS gel electrophoresis

The SDS gel electrophoresis was carried out largely in accordance with the original method prescribed by U. K. Lammli. For in-process checks, VAC-β samples were combined with dithiothreitol before application and decocted. The final checks were carried out both under reducing conditions and also under non-reducing conditions.

The gels were stained with Coomassie Blue.

Figure 45:
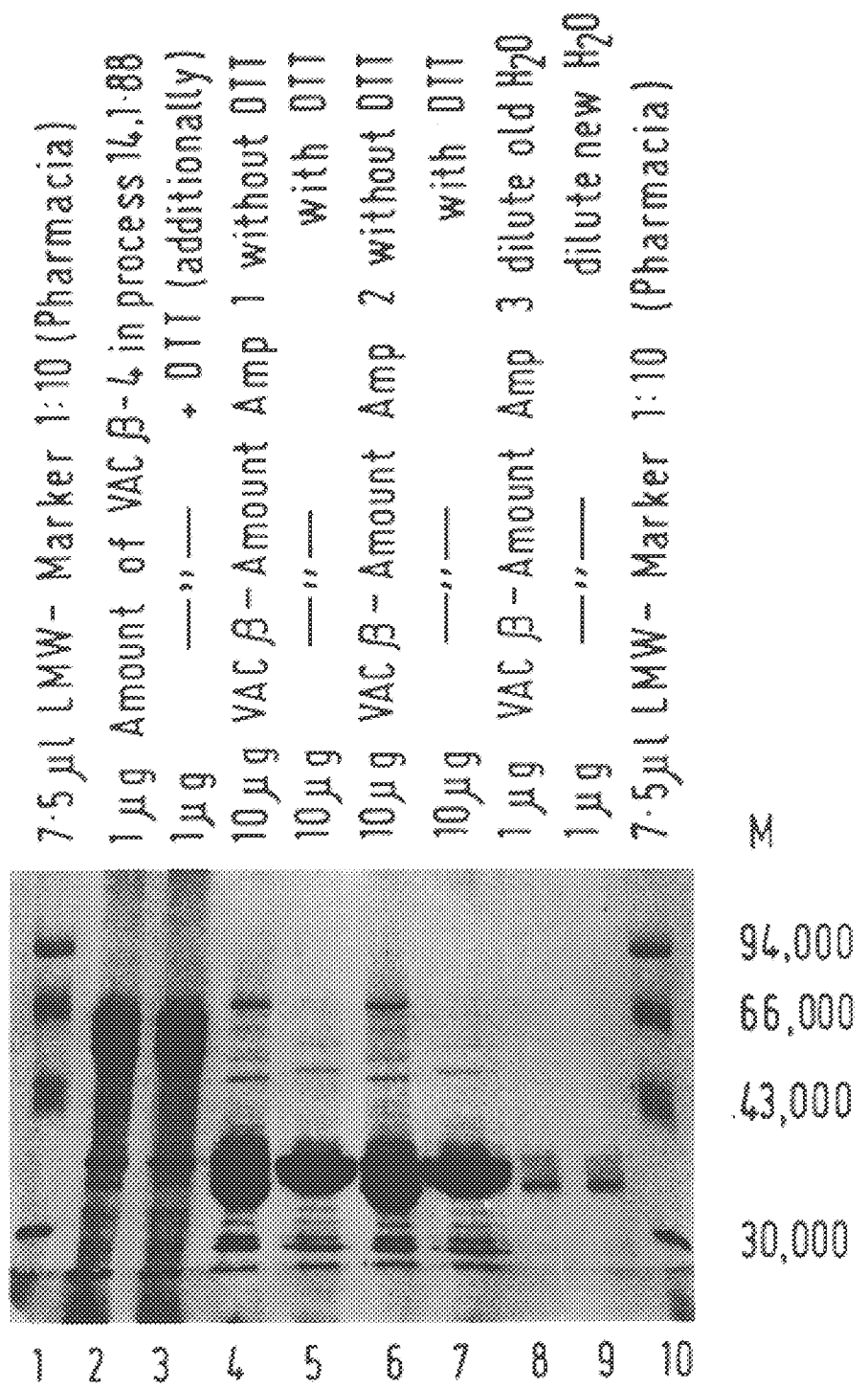

FIG. 45 shows an SDS gel of VAC-β samples.

Trace 1 and 10: molecular weight marker

Trace 2 and 3: in-process sample of VAC-β with and without DTT (dithiothreitol)

Trace 4 and 6: 10 µg of VAC-β, not reduced

Trace 5 and 7: 10 µg of VAC-β reduced with DTT.

Trace 8 and 9: 1 µg of VAC-β, not reduced.

VAC-β without reducing agents is detectable as a double band. The more intensive lower band at M approximately 36,000 is the oxidized form, whilst the upper band at M approximately 38,000 is the reduced form of VAC-β. The quantity distribution of the two forms is easier to see from traces 8 and 9.

After the addition of DTT as reducing agent, therefore, only the upper band is still visible (see traces 3, 5 and 7). Since traces 4 to 7 are greatly overloaded, some bands of residual impurities are also visible in addition to the VAC-β bands.

f) Isoelectric focussing

Figure 46A:
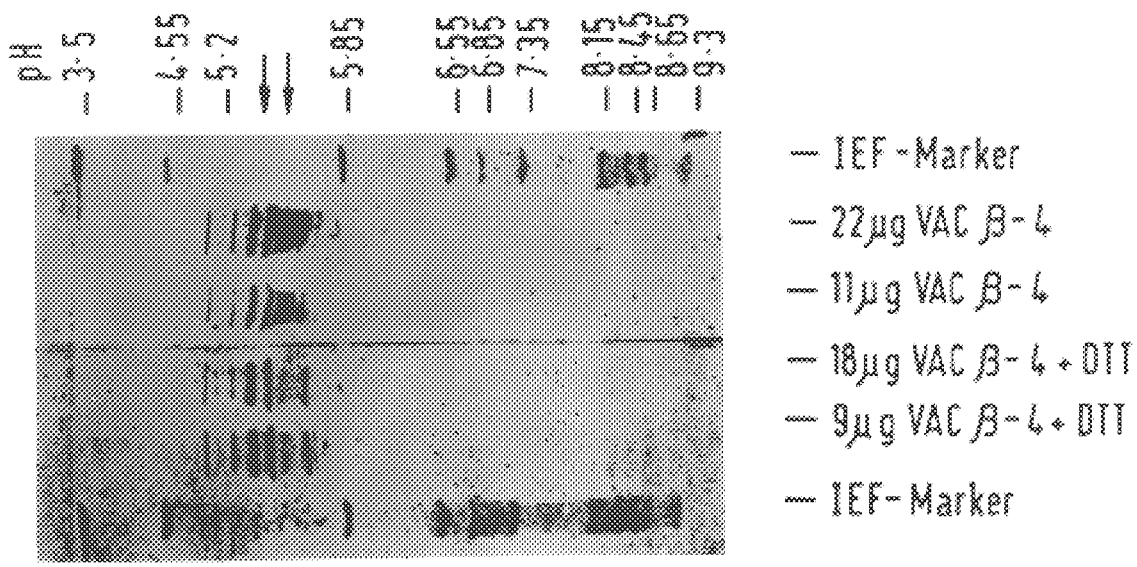

Staining is carried out with Coomassie Blue. The isoelectric focussing, FIG. 46 (3.3.1988/51) of largely purified VAC-β shows that VAC-β yields two main bands at pH 5.35 and 5.45, directly from the last purification stage (traces 2 and 3). The isoelectric point (pI) of VAC-β is hence significantly more basic than that of VAC-α (pI=4.9), which corresponds to expectations, since VAC-β contains less acidic amino acids.

After reduction with dithiothreitol (traces 4 and 5) the main band at pH 5.45 is greatly concentrated. This is obviously the reduced form of VAC-β.

EXAMPLE 14

Biological activities of VACα and VACβ

The prothrombinase complex was reconstituted from purified bovine coagulation factors and phospholipids. It consisted of 0.3 nM factor Xa, 0.6 nM factor Va, 1 µM prothrombin, 2 µM phospholipid vesicles (25% dioleoyl-phosphatidylserine, 75% dioleoyl-phosphatidylcholine) and 3 mM $CaCl_2$.

Figure 47:
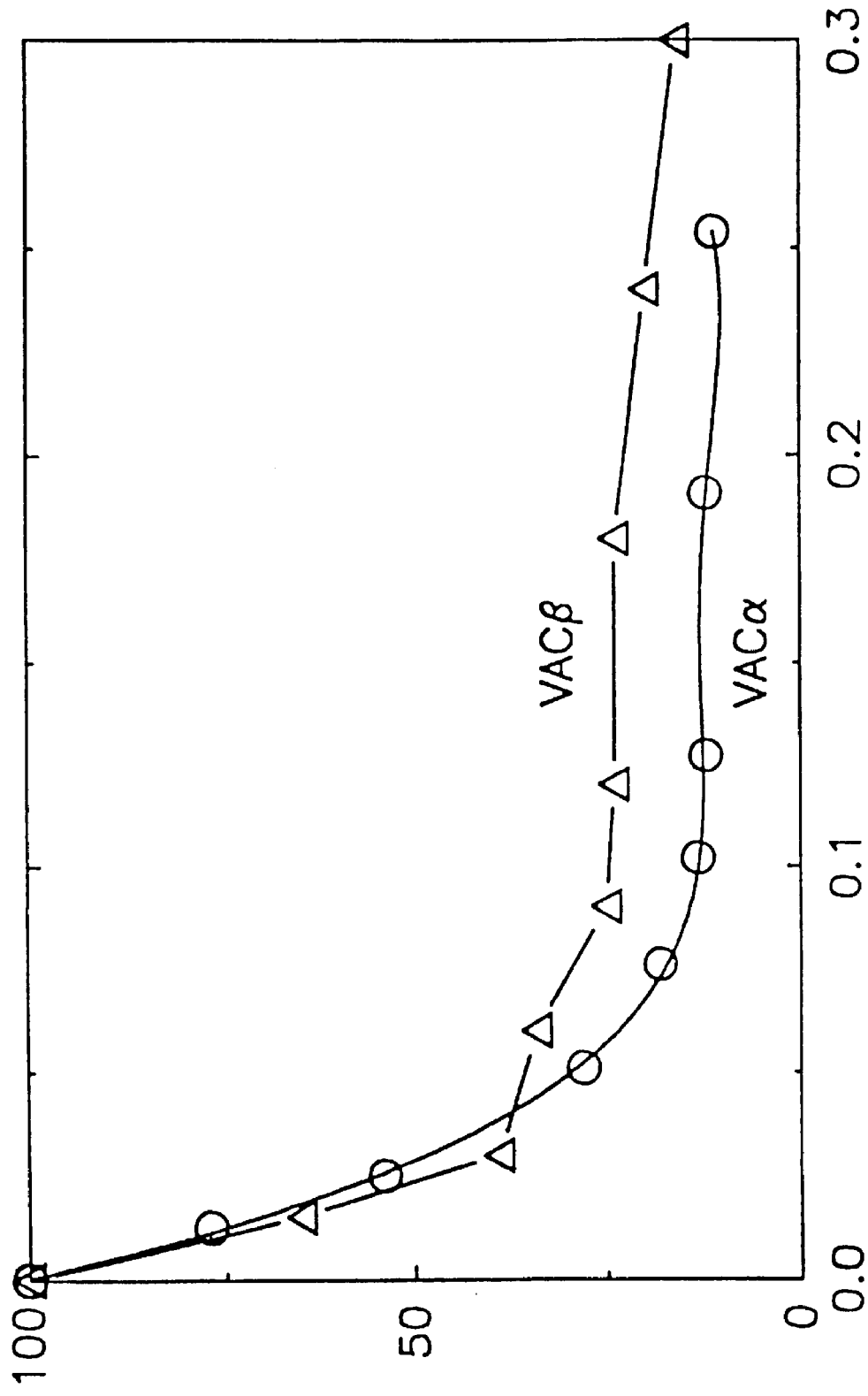

Prothrombin activation was measured as follows: Factor Xa, Va phospholipids, $Ca^{++}$ and varying amounts of VAC were incubated for two min at 37° C. The activation of prothrombin was started by its addition. At several time points aliquots were sampled from the mixture into the following buffer 50 mM Tris/HCl, 175 mM NaCl, 0.5 mg/ml BSA, 20 mM EDTA and 0.23 mM S2238. Amidolytic activity was followed at 405 nm. From a reference curve, constructed with known amounts of thrombin, the amount of activated prothrombin was determined subsequently. FIG. 47 shows the result.

E.coli were metabolically labeled with $^3$H-oleic acid and further processed as described elsewhere (Davidson, F. F., Dennis, E. A., Powell, M., & Glenney, J. R., Jr (1987), J. Biol. Chem. 262, 1698–1705). The E.coli membrane preparation contained 198 µM phospholipids with a specific activity of $1.2 \times 10^4$ cpm/nmol phospholipid. This membrane preparation functioned as phospholipase substrates in our assay. This assay was carried out as follows: 130 µl 0.1M Tris/HCl, pH 8.0, containing varying amounts of VAC and $Ca^{++}$, and 10 µl E.coli membranes were incubated at room temperature. At time point zero 10 µl 0.1M Tris/HCl 8.0, containing 2 ng bovine pancreas phospholipase $A_2$ was added. At time point two min, the reaction was stopped by the addition of 50 µl 2N HCl and 50 µl 0.1M Tris/HCl 8.0 containing 100 mg/ml BSA. The mixture was centrifuged for five min at 14,000 rpm. The amount of liberated $^3$H-oleic acid was determined in the supernatant by scintillation counting. Percent inhibition of phospholipase $A_2$ activity was calculated as follows:

$$100\% - [(\text{cpm}_{pla+vac} - \text{cpm}_{blank})/(\text{cpm}_{pla} - \text{cpm}_{blanc})] * 100\%$$

where $\text{cpm}_{pla+vac}$, $\text{cpm}_{pla}$ and $\text{cpm}_{blank}$ represent cpm measured in the supernatant of the mixtures containing respectively phospholipase $A_2$ and VAC, phospholipase $A_2$, and VAC. The results are given in FIGS. 48, 49, 50 and 51.

EXAMPLE 15

Development of monoclonal antibodies to VAC-α

1. Preparation of VAC-α coupled to keyhole limpet hemocyanin

VAC-α was covalently coupled to keyhole limpet hemocyanin (KLH; SIGMA chemical company, St. Louis, USA; catalogue number H-2133) as follows:

1.1 VAC-α/KLH preparation 1: 0.51 mg VAC-α dissolved in 1.5 ml phosphate-buffered saline pH 7.2 was mixed with 0.12 ml of a solution of keyhole limpet hemocyanin (8 mg/ml in phosphate-buffered saline pH 7.2). 0.017 ml of a 25% solution of glutardialdehyde was added and the solution was incubated for 45 minutes at room temperature, followed by overnight dialysis against 1 l of phosphate-buffered saline. Aliquots of this solution were stored at −20° C.

1.2 VAC-α/KLH preparation 2:

2.54 mg VAC-α dissolved in 2 ml 0.1M potassium phosphate—buffer pH 7.0 was mixed with 0.3 ml of a solution of keyhole limpet hemocyanin (see 1.1). 0.023 ml of a 25% solution of glutardialdehyde was added and the solution was incubated for 45 minutes at room temperature, followed by dialysis against 1 l of phosphate-buffered saline pH 7.2. Aliquots were stored at −20° C.

2. Immunization

A 10-week-old female Balb/c mouse was immunized as follows:

| Immunization | Day | VAC-α/KLH preparation | adjuvans |
|---|---|---|---|
| 1 | 1 | 1 (0.15 ml) | complete |
| 2 | 24 | 1 (0.15 ml) | incomplete |
| 3 | 49 | 1 (0.15 ml) | incomplete |
| 4 | 188 | 2 (0.1 ml) | incomplete |
| 5 | 225 | 2 (0.1 ml) | incomplete |
| 6 | 258 | 2 (0.1 ml) | incomplete |
| 7 | 265 | 2 (0.1 ml) | incomplete |
| 8 | 271 | 2 (0.1 ml) | incomplete |
| 9 | 272 | 2 (0.1 ml) | incomplete |
| 10 | 273 | 2 (0.1 ml) | none |

All immunizations (except the last one) employed a solution of the immunogen emulsified with an equal volume of Freund's adjuvant and were given by intraperitoneal injection.

3. Cell fusion and hybridoma selection

Peritoneal cells were obtained from Balb/c mice by lavage with sucrose solution (110 g/l in deionized water). The cells were collected by centrifugation and resuspended in Roswell Park Memorial Institute (RPMI) 1640 medium containing sodium penicillin G (100 units/ml) and streptomycin (50 units/ml) (subsequently termed "culture medium)" with 10% fetal calf serum to a concentration of approximately $3.5 \times 10^4$ cells/ml.0.1 ml—aliquots were dispensed into the wells of microtiter tissue culture plates (96 wells per plate); the plates were incubated overnight.

One day after the last immunization, the mouse was anesthesized in ether and killed by cervical dislocation. The spleen was removed aseptically and spleen cells were obtained by gentle scraping on a stainless steel net. The cells were suspended in 10 ml culture medium and collected by centrifugation. P3x63Ag8.653 murine myeloma cells (Kerney et al., J. Immunol. 123:1548; 1979) were propagated in stationary suspension culture in culture medium supplemented with 10% fetal calf serum. Approximately $10^8$ cells were collected by centrifugation, washed once in culture medium, and resuspended in 10 ml culture medium. The myeloma cells were added to the spleen cells; the mixed cell population was again collected by centrifugation and the medium supernatant was discarded. The cells were suspended in 3 ml of a sterile solution of 40% polyethylene glycol 4000 (Merck, Darmstadt, FRG, catalogue number 9727) in culture medium and incubated for 1.5 minutes at room temperature under gentle swirling, followed by further incubation without swirling for 1 minute. 3 ml of culture medium were added dropwise over a period of 1.5 minutes under gentle swirling. After 1 minute of incubation without swirling another 6 ml of culture medium were added dropwise over a period of 1.5 minutes under gentle swirling. Again the cells were incubated without swirling for 1 minute. The cell suspension was further diluted with 12 ml of culture medium containing 10% fetal calf serum added over a period of 3 minutes and left to stand for 15 minutes at room temperature. Subsequently, the cells were collected by centrifugation and resuspended in 150 ml of culture medium containing 20% fetal calf serum, thymidine ($1.6 \times 10^{-5}$ M), hypoxanthine ($10^{-1}$M) and aminopterin ($4 \times 10^{-7}$M) (subsequently termed "HAT medium"). 0.1 ml of this suspension were added to each of the wells seeded on the previous day with murine peritoneal cells. The plates were further incubated for 3 days. 0.075 ml of fresh HAT-medium were then added and incubation was continued for 8 days.

All cell cultures were kept at 37° C. in a water-saturated atmosphere containing 5% $CO_2$ in air.

3. Screening for cultures containing antibodies to VAC-α

An enzyme immunoassay technique was employed to screen for antibodies to VAC-α. The wells of 96-well polystyrene microtiter plates were coated with VAC-A (0.005 mg/ml in 0.1M sodium carbonate buffer pH 9.6) either overnight at 2°–8° C. or for one hour at 37° C. The solution was removed and the wells were washed once with deionized water. Remaining protein binding sites were blocked by incubation with a solution of bovine serum albumin (5 mg/ml in phosphate-buffered saline pH 7.2) for one hour at room temperature. The wells were washed once with water; 0.1 ml of hybridoma supernatants was added and incubated for 2–3 hours at room temperature. The solution was removed, the wells were washed threetimes with water. 0.05 ml of a solution of peroxidase-conjugated rabbit-immunoglobulins to mouse-immunoglobulins (Dakopatts, Copenhagen, Denmark; catalogue number P161; diluted 1:2000 in phosphate-buffered saline pH 7.2 containing 5 mg bovine serum albumin/ml) were added and incubated for another 2–3 hours at room temperature. Again the wells were washed threetimes with water and 0.1 ml of a freshly prepared mixture of equal volumes of o-phenylene diamine (8.65 mg/ml in 0.1 M potassium citrate pH 5), sodium perborate (3.75 mg/ml in 0.1M potassium citrate pH 5)) and water were added. After incubation for 30 minutes at room temperature 0.1 ml of 4N $H_2SO_4$ was added. The optical density of the solutions was determined in a multichannel photometer at a wavelength of 492 nm. Cell culture medium with 20% fetal calf serum was used as a negative control, and serum of the immunized mouse, diluted in phospate-buffered saline (pH 7.2) supplemented with 5 mg bovine serum albumin/ ml was employed as a positive control.

Supernatants of all hybridoma cultures were tested on two occasions, 11 and 13 days after cell fusion, respectively. Cultures giving a positive signal in both primary screening experiments were tested in a secondary screening experiment, in which uncoated assay plates were also used in addition to VAC-α-coated plates. Two of the cultures consistently gave positive reactions with coated, but not uncoated plates. The results are shown in the following table:

|  | Optical density at 492 nm | | | |
|---|---|---|---|---|
|  | Experiment 1 | | Experiment 2 | |
| Sample | coated | uncoated | coated | uncoated |
| mouse serum 1: 100 | 0.291 | 0.152 | 1.735 | 0.475 |
| Hybridoma VAA-8 | 1.061 | 0.102 | 1.169 | 0.108 |
| Hybridoma VAA-9 | 0.552 | 0.187 | 0.387 | 0.109 |
| negative control | 0.032 | 0.031 | 0.071 | 0.055 |

The positive cultures were cloned and frozen in liquid nitrogen following standard procedures.

EXAMPLE 16

Construction of expression vectors pRH281/n and pRH281/nT (n=5,6,7,8,9)

The expression vector pRH100 described in the E.P.A. Nr.[186,098] has several drawbacks:

a) the distance between the ribosomal binding site (rbs) and the translational start ATG is constant.

b) The region between rbs and ATG contains some C's and G's.

c) The −35 region of the trp promoter of Serratia marcescens is not optimal compared with the E.coli sequence (TTGACT versus TTGACA).

d) There is an unnecessary EcoRI site in front of the promoter.

A set of oligonucleotides was synthesized with the following sequences:

:Trp-1->   : :Trp-3->

AATTGACGCTGATGGCTAAAACATTGTGCAAAAAGAGGGTTGACATTGCC

-continued
```
CTGCGACTACCGATTTTGTAACACGTTTTTCTCCCAACTGTAACGG
     <-Trp-::
                              : - - >transcriptional start
                              :: Trp-5->
TTCGCGAACCAGTTAACTAGTACACAAGTTCACGGCTCGAGACGGTAAGG
AAGCGCTTGGTCAATTGATCATGTGTTCAAGTGCCGAGCTCTGCCATTCC
                      <-Trp4::                      -----
                                                     RBS
       SstI      ClaI
       ------EcoRI----
              -------:
AGGTTTAATATGAGCTCGAATTCAT
TCCAAATTATACTCGAGCTTAAGTAGC
-----        ----      <-Trp-6:
RBS          translational start-ATG
    : n=5 :
```

100 pmol of the oligonucleotides Trp-2, Trp-3, Trp-4 and Trp-5 were phosphorylated in 10 μl. After completion of the reaction equimolar amounts (100 pMol) of Trp-1 and Trp-2, Trp-3 and Trp-4 as well as Trp-5 and Trp-6 were combined, heated to 100° C. and slowly cooled to allow for annealing. The oligonucleotide pairs were combined and ligated in a total volume of 55 μl. pAT153 was doubly digested with EcoRI and ClaI and large vector fragment isolated. 50 ng pAT153 fragment and 20 pmol synthetic promoter DNA were ligated in 20 μl solution. Competent *E.coli* HB101 were transformed with the resulting plasmid. The plasmid DNA from some of the resulting clones was isolated and the region of the inserted DNA checked by sequencing. One plasmid was selected and named pRE281/5, 5 representing the number of nucleotides between the rbs and the translation start ATG.

Starting from this expression vector the XhoI-SstI insert was replaced by the following oligonucleotide pairs:

a)  TCGAGACGGTAAGGAGGTTTAAATATGAGCT    Trp-9
        CTGCCATTCCTCCAAATTTATAC         Trp-10 b)  TCGAGACGGTAAGGAGGTTTAAATAATGAGCT   Trp-11
        CTGCCATTCCTCCAAATTTATTAC        Trp-12 c)  TCGAGACGGTAAGGAGGTTTAAAATAATGAGCT  Trp-13
        CTGCCATTCCTCCAAATTTTATTAC       Trp-14

-continued
d)  TCGAGACGGTAAGGAGGTTTAAAAATAATGAGCT Trp-15
        CTGCCATTCCTCCAAATTTTTATTAC      Trp-16

The resulting expression vectors were named pRH281/6, pRH281/7, pRH281/8 and pRH281/9.

These new expression vectors show the following features:

a) the original EcoRI site of pAT153 is destroyed.

b) the −35 region of the Serratia marcescens promoter is identical to the one of the *E.coli* trp-promoter.

c) there is a singular XhoI site in front of the rbs allowing the substitution of this rbs against another one.

d) the G of the translation start ATG is the first base of an SstI (=SacI) site. Cutting with SstI followed by removal of the 3' overhang creates a blunt end which can be ligated to any cDNA or gene. If this DNA starts with the first base of a translated region, correct transcription and translation occurs in *E.coli*.

e) the SstI site is followed by a singular EcoRI, ClaI and HindIII site which can be used for a directed cloning of any DNA which should be expressed. In-addition, it is also possible to use the singular restriction enzyme sites contained in the tetracycline resistance gene.

f) the variation /5 to /9 makes it possible to find the optimal spacing between the rbs and the ATG for any gene to be expressed.

Sometimes it is advantageous to have a transcription termination signal on the 3' site of the expressed gene (R. Gentz et al., Proc.Natl.Acad.Sci.USA 78 (1981), 4936–4940). The HindIII-SalI fragment of PRH281/5 was removed and replaced by an oligonucleotide pair containing the phoA transcription terminator (H. Shuttleworth et al., Nucl.Acids Res. 14 (1986), 8689; C. N. Chang et al., Gene 44 (1986), 121–125);

```
                              :EBI-456->
        AGCTTGGATCCGTCGACCGCGCCCGGCAGTGAATTTTCGCTGCCGGGTGG
             ACCTAGGCAGCTGGCGCGGGCCGTCACTTAAAAGCGACGGCCCACC
                   :-------
             ----- BamHI ------
        HindIII      SalI
                       :
        TTTTTTTGCTGC
        AAAAAAACGACGAGCT
                  <-EBI-469:
```

10 pMol of the annealed oligonucleotides and 100 ng of the HindIII-SalI cut vector fragment of pRH281/5 were ligated in a volume of 20 μl. After transformation of *E.coli* HB101, isolation of plasmid DNA from some of the colonies and check by sequencing one plasmid was selected and designated as pRH281/5T.

Starting with this plasmid the whole set of expression vectors PRE281/6T, pRH281/7T, pRH281/8T und pRH281/9T was produced using the procedure described above.

EXAMPLES 17

Mutants of VAC-alpha

The following mutations were introduced in the VAC-alpha DNA (the numbering of amino acids and nucleotides is the same as in FIG. 4):

a) reduction of the size of the VAC molecule: VAC-alpha has a fourfold repetition of a 67/68 amino acid long sequence with a singular N-terminal extension (FIG. 6). Three mutants were produced;

i) deletion of amino acids 2 to 18: elimination of the singular N-terminal extension, Met-1 is joined to Ala-19.

ii) Deletion of the third and fourth repeat: the Arg-161 codon was mutated into a stop codon.

iii) Deletion of the N-terminal singular extension together with the first and the second repeat. Met-1 is joined to Ala-165.

b) Arg-161 is a possible site for a proteolytic attack. Therefore this amino acid was mutated:

i) Arg-161 to Glu-161 ii) Arg-161 to Gln-161.

c) The introduction of a factor Xa cut site between the second and the third repeat could possibly lead to a molecule which binds factor Xa escaping the inhibition of the coagulation cascade by VAC. In addition this mutant could be possibly cut by factor Xa into two functional half-molecules thereby enhancing the inhibitory effect of VAC. The following mutation was performed: Asp-168 to Glu-168, Glu-169 to Gly-169 and Ala-170 to Arg-170. This introduces the factor Xa recognition sequence Ile-Glu-Gly-Arg.

d) In order to get some information about the biological significance of the cysteine-316 and its possible role in the dimer formation the following mutations were performed:

i) Cys-316 to Ser-316 and ii) Cys-316 to Val-316.

In order to study the influence of the N-terminal extension this region (Ala-2 to Ala-19) was replaced by the N-terminal extensions of lipocortin I, calpactin I and VAC-beta.

The first step was the construction of the expression vector PGN10 starting from pRE291. This expression vector uses the phage lambda cII rbs instead of the STII rbs used in pRH291. pRH291 was doubly cut with XhoI and KpnI. The large fragment was isolated. 40 pMol of the oligonucleotide pair EBI-725/EBI-727 with the sequence:

EBI-725 TCGAGTTATCTAAGGAAATACTTA-CATATGGCACAGGTTCTCAGAGGTAC

EBI-727 CAATAGATTCCTTTATGAATGTATAC-CGTGTCCAAGAGTCTC XhoI RBS ATG KpnI was annealed in 6 μl solution and ligated with appr. 200 ng pRH291/large fragment in a total of 20 μl. Competent *E.coli* HB101 were transformed. Plasmids of some of the resulting colonies were isolated and the sequence of the newly inserted DNA checked by sequencing. One clone was selected and named pGN10.

As a preliminary the PvuII-SphI fragment of pGN10 was isolated. PvuII cuts in the phoA promoter region and SphI cuts in the 3' nontranslated region of the VAC-alpha cDNA. The cDNA containing fragment was isolated and ligated into M13mp18 double stranded DNA doubly cut with SmaI and SphI. After transformation of competent *E.coli* JM101 one resulting plaque was selected and the single stranded DNA prepared at a larger scale.

The oligonucleotide directed mutagenesis was performed with the "oligonucleotide directed in vitro mutagenesis system" (Amersham, code RPN.2322) following the instruction of the supplier.

After sequencing of the resulting mutants the corresponding double stranded form of the recombinant M13mp18/VAC-alpha phage DNA was isolated using the miniprep procedure. Except with the mutation with the oligonucleotide EBI-977 (ClaI site at nt.105–110) the DNAs were cut with XhoI and SphI and the VAC-cDNA containing fragment isolated. Appr. 50 ng of each fragment were ligated with 50 ng XhoI-SphI doubly cut pRH281/5 vector in 10 μl solution and the resulting plasmid used to transform competent *E.coli* HB101. The plasmids of some of the resulting colonies were isolated and the construction checked by restriction enzyme analysis. The finally selected colony was fermented at a lab scale and the proteins of the bacteria subjected to a Western blot analysis.

The following table summarizes the mutants:

| Mutation-oligo | resulting expressions vector | properties of the new clone |
|---|---|---|
| EBI-1051 | pGN42 | deletion from Ala-2 to Arg-18 |
| EBI-964 | pGN29 | translation stop at 161 (deletion from Arg-161 to Asp-320) |
| EBI-11O5 | pGN43 | deletion from Ala-2 to Asp-164 |
| EBI-1103 | pGN44 | Arg-161 to Gln-161 |
| EBI-1104 | pGN45 | Arg-161 to Glu-161 |
| EBI-960 | pGN30 | factor Xa recognition sequence from 167 to 170 |
| EBI-961 | pGN41 | Cys-316 to Ser-316 |
| EBI-959 | pGN46 | Cys-316 to Val-316 |
| EBI-977 | pGN31 | C1aI site from nt.105 to 110 |

The sequences of the mutation oligonucleotides are (5'→3'):

EBI-1051: CCGAAGAGTTTCTGCATCAGCCATATG-TAAGTATTTCCTTAG

EBI-964: AATTCCAGCATCAGGGTCTTAGTTAGC-CTGAAGGAGAAC

EBI-1105; AGCTTCATCAATTCCAGCCATATGTAAG-TATTTCC

EBI-1103: AATTCCAGCATCAGGGTCCTGGTTAGC-CTGAAGGAGAAC

EBI-1104: AATTCCAGCATCAGGGTCTTCGTTAGC-CTGAAGGAGAAC

EBI-960; GCCTGAGCATCTTGTTCAACTTGACGAC-CTTCAATTCCAGCATCAGGGTCTCTG

EBI-961: CGTTAGTCATCTTCTCCTGAGAGCAGCA-GAAGAGC

EBI-959: CGTTAGTCATCTTCTCCCACGAGCAGCA-GAAGAGC

EBI-977: CAACAGAGTCAGGATCGATTCCTCATCT-GTGCCC

The indicated sequences are complementary to the DNA sequence shown in FIG. 4, which is due to the cloning of the VAC-alpha cDNA in M13mp18 as described above.

The mutant with the ClaI site at nt.105 to 110 was isolated by cutting with EcoRI and HindIII and cloned into EcoRI-HindIII doubly digested Bluescribe M13+ DNA (Stratagene, La Jolla, Calif., USA). The resulting plasmid was named pGN31. pGN31 was doubly digested with ClaI and XhoI and the large fragment isolated. Using the following oligonucleotide pairs the DNAs coding for the N-termini specific for Lipocortin I (K.-S. Huang et al. Cell 46 (1986), 191–199), Calpactin I (=Lipocortin II, K.-S. Huang et al. Cell 46 (1986), 191–199) und VAC-beta were introduced:

a) Lipocortin I specific N-terminus

:EBI-972->                    : start Lipocortin
TGAGAGGTTGAGGTGATTTTATGGCAATGGTATCAGAATTCCTCAAGCA
        CTCAACTCCACTAAAATACCGTTACCATAGTCTTAAGGAGT TCGT
            :
GGCTGGTTTATTGAAAATGAAGAGCAGGAATATGTTCAAACTGTGAAGT
CCGGACCAAATAACTTTACTTCTCGTCCTTATACAAGTTTGACACTTCA
        : : EBI-977->
CATCCAAAGGTGGTCCCGGATCAGCGGTGAGCCCCTATCCTACCTTCAAT
GGTGGTTTCCACCAGGGCCTAGTCGCCACTCGGGGATAGGATGGAAGTTA
<EBI-988: :
:VAC-alpha coding region
CATCCTCGGATGCAGAAACTCTTCGGAAGGCTATGAAAGGCTTGGGCAC
GGTAGGAGCCTACGTCTTTGAGAAGCCTTCCGATACTTTCCGAACCCGTG
AGATGAGGAAT
TCTACTCCTTAGC
<-EBI-982:

1 pMol of EBI-978 and 1 pMol EBI-988 were combined and phosphorylated in 6 µl solution. The reaction was teminated by heating to 100° C., 1 pmol of each EBI-972 and EBI-982 were added, the solution heated-again and slowly cooled. The two oligonucleotide pairs were ligated using ligase. About 1 µg PGN31/ClaI-XhoI large fragment was added, the volume size increased to 40 µl and ligated. After transformation of competent E.coli HB101 several colonies were selected and their plasmids isolated as single strands according to the Bluscribe protocol. After the sequencing check one of the plasmids was selected and named pGN32. PGN32 was doubly cut with XhoI and HindIII (HindIII cuts on the 3' side of the SphI site and is located in the multicloning site of the Bluescribe M13+ vector) and the insert was purified. pRH281/5 was also doubly digested with XhoI and HindIII and the vector part isolated. 200 ng pGN32 insert and appr. 50 ng pRH281/5 vector DNA were ligated in 20 µl solution. E.coli HB101 was transformed with this DNA. Plasmid DNA from several resulting ampicillin resistant clones was isolated and checked by restriction enzyme analysis. The selected colony was fermented at a lab scale, and the proteins of the bacteria subjected to a Western blot analysis using rabbit-anti-VAC-antiserum. The resulting expression plasmid for the Lipocortin I/VAC-alpha hybrid was named pGN35.

b) Calpactin I specific N-terminus
:EBI-990->
TCGAGAGGTTGAGGTGATTTTATGTCTACTGTTCACGAAATCCTGTGCAA
        CTCCAACTCCACTAAAATACAGATGACAAGTGCTTTAGGACACGTT
            :
GCTCAGCTTGGAGGGTGATCACTCTACACCCCCAAGTGCATATGGGTCTG
CGAGTCGAACCTCCCACTAGTGAGATGTGGGGGTTCACGTATACCCAGAC
                                                  <-
: :EBI-1--1->                :VAC-alpha coding region
TCAAAGCCTATACTAACTTTGATGCTGAGCGGGATGCAGAAACTCTTCGG
AGTTTCGGATATGATTGAAACTACGACTCGCCCTACGTCTTTGAGAAGCC
EBI-985: :
AAGGCTATGAAAGGCTTGGGCACAGATGAGGAAT
TTCCGATACTTTCCGAACCCGTGTCTACTCCTTAGC
                <-EBI-994:

The construction of the recombinant Bluescribe M13+ plasmid pGN33, the sequencing check thereof and the recloning using the expression vector pRH281/5 was performed according to the procedure outlined for the Lipocortin I hybrid. The resulting expression plasmid (Calpactin I/VAC-alpha hybrid) was named pGN36.

c) VAC-beta specific N-terminus:

:EBI-987->
TCGAGAGGTTGAGGTGATTTTATGTCTACTGTTCACGAAATCCTGTGCAA
        CTCCAACTCCACTAAAATACAGATGACAAGTGCTTTAGGACACGTT
            :
                                                  :VAC-
GGAGGGTGTCACAGTGAAGAGCAGCTCCCACTTCAACCCAGACCCTGATG
CCTCCCACAGTGTCACTTCTCGTCGAGGGTGAAGTTGGGTCTGGGACTTAC
alpha coding region
CAGAAACTCTTCGGAAGGCTATGAAAGGCTTGGGCACAGATGAGGAAT
GTCTTTGAGAAGCCTTCCGATACTTTCCGAACCCGTGTCTACTCCTTAGC
                                        <-EBI-989:

1 pMol of each oligonucleotide was annealed by heating and slowly cooling in 6 µl solution. This DNA was ligated into XhoI-ClaI doubly cut PGN31 vector as described above. The construction of the expression vector pGN37 (VAC-beta/VAC-alpha hybrid in pRH281/5) was performed as described above.

We claim:

1. An isolated DNA molecule which contains a nucleic acid sequence encoding a polypeptide having the amino acid sequence according to FIG. 7.

2. An isolated DNA molecule comprising a nucleotide sequence of VAC-beta, wherein said nucleotide sequence comprises the sequence set forth in FIG. 7.

3. An isolated DNA molecule which contains a nucleic acid sequence encoding a polypeptide which demonstrates immunoreactivity with anti-VAC-β antibodies and which has at least one biological activity of VAC-β, said activity being selected from the group consisting of: the inhibition of prothrombinase activity, the inhibition of fibrin formation, the inhibition of thrombin formation, the inhibition of tissue-factor induced factor X activation, and the inhibition of phospholipase A2 activity, said DNA molecule being capable of hybridizing to the DNA molecule of claim 1 under stringent conditions which select for more than 85% sequence identity with the proviso that said DNA is not the sequence shown in FIG. 4.

4. An isolated DNA molecule which contains a nucleic acid sequence encoding a polypeptide which demonstrates immunoreactivity with anti-VAC-β antibodies and which has at least one biological activity of VAC-β said activity being selected from the group consisting of: the inhibition of prothrombinase activity, the inhibition of fibrin formation, the inhibition of thrombin formation, the inhibition of tissue-factor induced factor X activation, and the inhibition of phospholipase A2 activity, said DNA molecule being capable of hybridizing to the DNA molecule of claim 1 under stringent conditions which select for more than 90% sequence identity with the proviso that said DNA is not the sequence shown in FIG. 4.

* * * * *